United States Patent
Berger et al.

(10) Patent No.: US 11,596,636 B2
(45) Date of Patent: Mar. 7, 2023

(54) TAILORED COMBINATORIAL EPIGENETIC THERAPIES FOR P53 GAIN-OF-FUNCTION TUMORS

(71) Applicant: The Trustees of the University of Pennsylvania, Philadelphia, PA (US)

(72) Inventors: Shelley L. Berger, Wayne, PA (US); Xianxin Hua, Wynnewood, PA (US); Morgan Sammons, Philadelphia, PA (US); Jiajun Zhu, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 15/110,967

(22) PCT Filed: Jan. 14, 2015

(86) PCT No.: PCT/US2015/011355
§ 371 (c)(1),
(2) Date: Jul. 12, 2016

(87) PCT Pub. No.: WO2015/108940
PCT Pub. Date: Jul. 23, 2015

(65) Prior Publication Data
US 2016/0339035 A1  Nov. 24, 2016

Related U.S. Application Data
(60) Provisional application No. 62/010,239, filed on Jun. 10, 2014, provisional application No. 61/931,271, (Continued)

(51) Int. Cl.
*A61K 31/5377* (2006.01)
*A61K 31/136* (2006.01)
(Continued)

(52) U.S. Cl.
CPC ........ *A61K 31/5377* (2013.01); *A61K 31/136* (2013.01); *A61K 31/519* (2013.01); *A61K 31/713* (2013.01)

(58) Field of Classification Search
CPC .............. A61K 31/5377; A61K 31/136; A61K 31/519; A61K 31/713
See application file for complete search history.

(56) References Cited

U.S. PATENT DOCUMENTS
2013/0210918 A1   8/2013 Gottesfeld et al.

OTHER PUBLICATIONS

Nishioka, Simultaneous inhibition of DNA methyltransferase and histone deacetylase induces p53-independent apoptosis via down-regulation of Mcl-1 in acute myelogenous leukemia cells, Leukemia Research, 2011, 35, pp. 932-939.*

(Continued)

*Primary Examiner* — Jared Barsky
*Assistant Examiner* — Andrew P Lee
(74) *Attorney, Agent, or Firm* — Riverside Law LLP

(57) ABSTRACT

The present invention provides compositions and methods for treating and preventing cancer. The invention comprises an inhibitor of epigenetic regulators, including MLL1, MLL2, MOZ, menin, WDR5, or a combination thereof. In one embodiment, the invention provides a personalized method of treating a cancer as dependent upon its epigenetic signature.

14 Claims, 33 Drawing Sheets
Specification includes a Sequence Listing.

Related U.S. Application Data filed on Jan. 24, 2014, provisional application No. 61/927,311, filed on Jan. 14, 2014.

(51) Int. Cl.
*A61K 31/519* (2006.01)
*A61K 31/713* (2006.01)

(56) References Cited

OTHER PUBLICATIONS

Danziger et al., Automated Site-directed Drug Design: A General Algorithm for Knowledge Acquisition about Hydrogen-Bonding Regions at Protein Surfaces, Mar. 22, 1989, The Royal Society, Proceedings of the Royal Society of London.Series B, Biological Sciences, vol. 236, No. 1283, p. 101-113.*
Simone, Oncology: Introduction, Cecil Textbook of Medicine, 20th Edition, 1996 vol. 1, pp. 1004-1010.*
Yokoyama, Menin Critically Links MLL Proteins with LEDGF on Cancer-Associated Target Genes, Cancer Cell, 2008, 13, pp. 36-46.*
Casiano, Tumor-associated Antigen Arrays for the Serological Diagnosis of Cancer, Molecular and Cellular Proteomics, 5(10), pp. 1745-1759.*
Potter, The failure of cancer chemoprevention, 2014, Carcinogenesis, 35(5), pp. 974-982. (Year: 2014).*
Nishioka, Chie et al., "Simultaneous inhibition of DNA methyltransferase and histone deacetylase induces p53-independent apoptosis via down-regulation of Mcl-1 in acute myelogenous leukemia cells", Leukemia Research, vol. 35:932-993 (2011).
Dou, Yali et al., "Physical Association and Coordinate Function of the H3 K4 Methyltransferase MLL1 and the H4 K16 Acetyltransferase MOF", Cell, vol. 121:273-885 (2005).
Shi, Albin et al., "Structural insights into inhibition of the bivalent menin-MLL itneraction by small molecules in leukemia", Blood, vol. 120:4461-4469 (2012).
Kiss, Róbert et al., "Discovery of Novel Human Histamine H4 Receptor Ligands by Large-Scale Structure-Based Virtual Screening", J Med Chem, vol. 51:3145-3453 (2008).
PubChem compound CID 91623360 "GTPL8231". Mar. 19, 2015.
Karatas et al., "High-Affinity, Small-Molecule Peptidomimetic Inhibitors of MLL1/WDR5 Protein-Protein Interaction", 2013, J. Am. Chem. Soc., 135, 669-682.
Cao et al., "Targeting MLL1 H3 K4 methyltransferase activity in MLL leukemia", 2014, Molecular Cell, 53(2): 247-251.
Grembecka et al., "Menin-MLL Inhibitors Reverse Oncogenic Activity of MLL Fusion Proteins in Leukemia", 2012, Nat Chem Biol, 8: 277-284.
Senisterra et al., "Small-molecule inhibition of MLL activity by disruption of its interaction with WDR5", 2013, The Biochemical Journal, 449:151-159.
Karatas et al., "Analysis of the Binding of Mixed Lineage Leukemia 1 (MLL1) and Histone 3 Peptides to WD Repeat Domain 5 (WDR5) for the Design of Inhibitors of the MLL1-WDR5 Interaction", 2010, Med. Chem., 53(14): 5179-5185.
Lawrence MS et al., "Discovery and saturation analysis of cancer genes across 21 tumor types", 2014, Nature, 495-501.
Brosh et al., "When mutants gain new powers: news from the mutant p53 field", 2009, Nat Rev Cancer, 9: 701-713.
Freed-Pastor et al., "Mutant p53: one name, many proteins", 2012, Genes Dev, 26:1268-1286.
Muller et al., "p53 mutations in nature", 2013, Nat Cell Biol: 15, 2-8.
Lang et al., "Gain of Function of a p53 Hot Spot Mutation in a Mouse Model of Li-Fraumeni Syndrome", 2004, Cell, 119: 861-872.
Olive et al., "Mutant p53 Gain of Function in Two Mouse Models of Li-Fraumeni Syndrome", 2004, Cell, 119: 847-860.
Zhang et al., "Tumor-Associated Mutant p53 Drives the Warburg Effect", 2013, Nat Commun. 4:2935 (pp. 1-33).
Subramanian et al., "A mutant p53/let-7i-axis-regulated gene network drives cell migration, invasion and metastasis", Oncogene 34(9):1094-1104 (Feb. 26, 2015). (doi:10.1038/onc.2014.46).
Weissmueller et al., "Mutant p53 drives pancreatic cancer metastasis through cell-autonomous PDGF receptor beta signaling", 2014, Cell, 157: 382-394.
Do et al., "Mutant p53 cooperates with ETS2 to promote etoposide resistance", 2012, Genes Dev, 26: 830-845.
Scian et al., "Modulation of Gene Expression by Tumor-Derived p53 Mutants", 2004, Cancer Res, 64: 7447-7454.
Garritano et al., "More targets, more pathways and more clues for mutant p53", 2013, Oncogenesis, 2: e54 (pp. 1-7).
Dawson et al, "Cancer Epigenetics: From Mechanism to Therapy", 2012, Cell, 150: 12-27.
Tam et al., "The epigenetics of epithelial-mesenchymal plasticity in cancer", 2013, Nat Med, 19(11):1438-49.
Kouzarides, T., "Chromatin Modifications and Their Function", 2007, Cell, 128: 693-705.
Li et al., "The Role of Chromatin during Transcription", 2007, Cell, 128: 707-719.
Bernstein et al., "An Integrated Encyclopedia of DNA Elements in the Human Genome", 2012, Nature, 489: 57-74.
Gertz et al., "Distinct properties of cell type-specific and shared transcription factor binding sites", 2013, Mol Cell, 52: 25-36.
Voss et al., "MOZ Regulates the Tbx1 Locus, and Mox mutation Partially Phenocopies DiGeorge Syndrome", 2009, Dev Cell, 17: 674-686.
Shilalifard, Ali. "The COMPASS Family of Histone H3K4 Methylases: Mechanisms of Regulation in Development and Disease Pathogenesis", 2012, Annu Rev Biochem, 81: 65-95.
Wang et al., "Global Analysis of H3K4 Methylation Defines MLL Family Member Targets and Points to a Role for MLL1-Mediated H3K4 Methylation in the Regulation of Transcriptional Initiation by RNA Polymerase II", 2009, Mol Cell Biol, 29: 6074-6085.
Milne et al., "MLL Targets SET Domain Methyltransferase Activity to Hox Gene Promoters", 2002, Mol Cell, 10: 1107-1117.
Nakamura et al., "ALL-1 is a Histone Methyltransferase that Assembles a Supercomplex of Proteins Involved in Transcriptional Regulation", 2002, Mol Cell, 10: 1119-1128.
White, Eileen. "Exploiting the bad eating habits of Ras-driven cancers", 2013 Genes Dev 27, 2065-2071.
Karlsson et al., "Rho GTPase function in tumorigenesis", 2009 Biochim Biophys Acta 1796, 91-98.
Lim et al., "Mutant p53 mediates survival of breast cancer cells", 2009, Br J Cancer, 101: 1606-1612.
Zhu et al., "Human Homologue of Yeast Rad23 Protein A Interacts with p300/Cyclic AMP-responsive Element Binding (CREB)-binding Protein to Down-Regulate Transcriptional Activity of p53", 2001, Cancer Res, 61: 64-70.
Dawson et al., "Targeting Epigenetic Readers in Cancer", 2012, N Engl J Med, 367: 647-657.
Huang et al., "The same pocket in menin binds both MLL and JUND but has opposite effects on transcription", 2012, Nature, 482: 542-546.
Matkar et al., "Menin: a scaffold protein that controls gene expression and cell signaling", 2013, Trends Biochem Sci, 38: 394-402.
Yokoyama et al., "Leukemia Proto-Oncoprotein MLL Forms a SET1-Like Histone Methyltransferase Complex with Menin to Regulate Hox Gene Expression", 2004, Mol Cell Biol, 24: 5639-5649.
Caslini et al., "Interaction of MLL AMino Terminal Sequences with Menin is Required for Transformation", 2007, Dancer Res, 67: 7275-7283.
Thiel et al., "Menin as a Hub Controlling Mixed Lineage Leukemia", 2012, Bioessays, 34: 771-780.
Yokoyama et al., "The Menin Tumor Suppressor Protein is an Essential Oncogenic Cofactor for MLL-Associated Leukemogenesis", 2005, Cell, 123: 207-218.
Thiel et al., "MLL-AF9-Induced Leukemogenesis Requires Coexpression of the Wild-Type Mll Allele", 2010, Cancer Cell, 17: 148-159.

(56) References Cited

OTHER PUBLICATIONS

Grebien et. al., "Pharmacological targeting of the Wdr5-MLL interaction in c/EBPα N-terminal leukemia", 2015, Nature Chemical Biology (pp. 571-582).

* cited by examiner

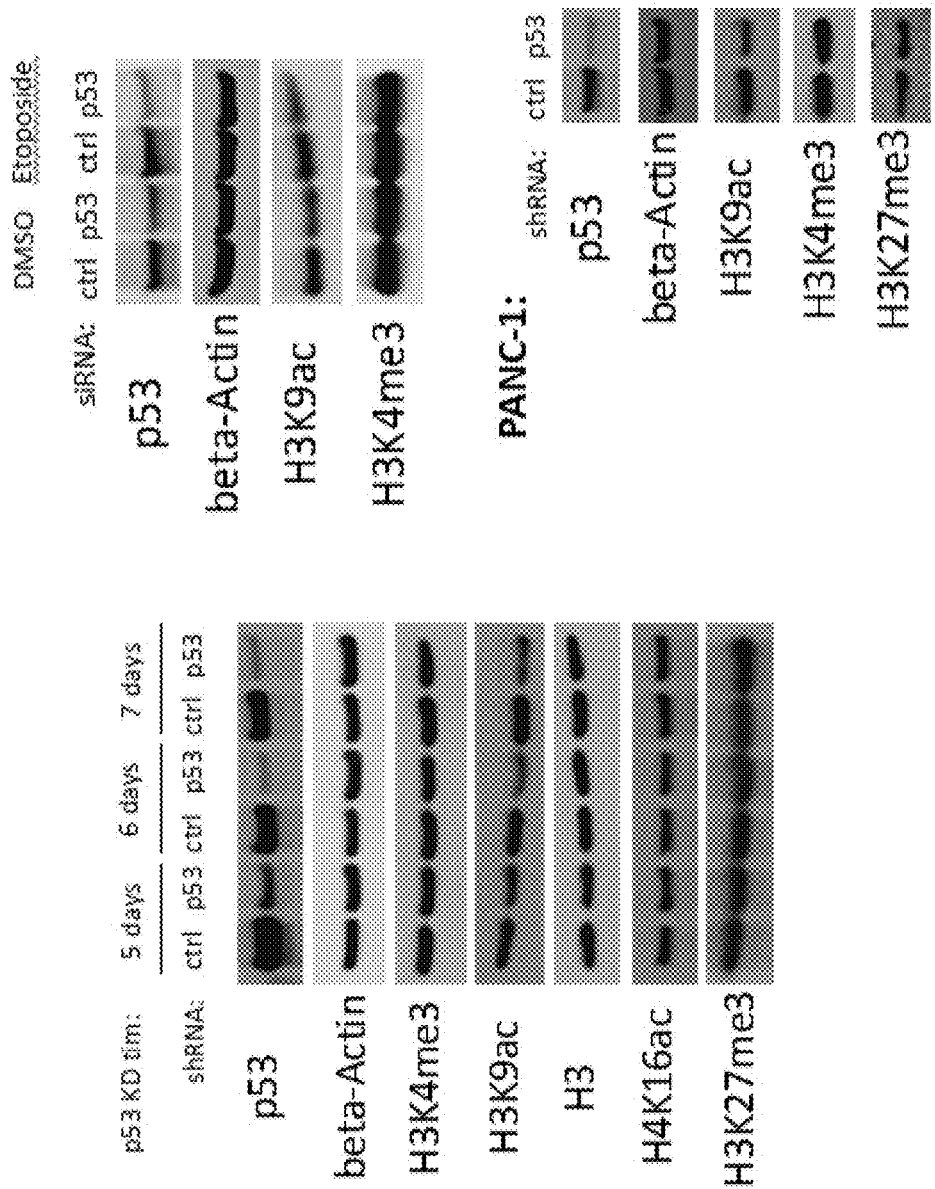

SEQUENCE LISTING

```
<160> NUMBER OF SEQ ID NOS: 3

<210> SEQ ID NO 1
<211> LENGTH: 14
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (1)..(1)
<223> OTHER INFORMATION: fluoroscein attached to Arg
<220> FEATURE:
<221> NAME/KEY: MISC_FEATURE
<222> LOCATION: (14)..(14)
<223> OTHER INFORMATION: amide attached to Gly

<400> SEQUENCE: 1

Arg Trp Arg Phe Pro Ala Arg Pro Gly Thr Gly Arg Arg Gly
1               5                   10

<210> SEQ ID NO 2
<211> LENGTH: 14
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (1)..(1)
<223> OTHER INFORMATION: biotin attached to Arg
<220> FEATURE:
<221> NAME/KEY: MISC_FEATURE
<222> LOCATION: (14)..(14)
<223> OTHER INFORMATION: amide attached to Gly

<400> SEQUENCE: 2

Arg Trp Arg Phe Pro Ala Arg Pro Gly Thr Gly Arg Arg Gly
1               5                   10

<210> SEQ ID NO 3
<211> LENGTH: 20
<212> TYPE: PRT
<213> ORGANISM: Artificial Sequence
```

```
<220> FEATURE:
<223> OTHER INFORMATION: Chemically synthesized
<220> FEATURE:
<221> NAME/KEY: MISC_FEATURE
<222> LOCATION: (1)..(1)
<223> OTHER INFORMATION: biotin attached to Met
<220> FEATURE:
<221> NAME/KEY: MISC_FEATURE
<222> LOCATION: (20)..(20)
<223> OTHER INFORMATION: amide attached to Pro

<400> SEQUENCE: 3

Met Ala His Ser Cys Ala Trp Ala Phe Pro Gly Ser Gly Ser Cys Ala
1               5                   10                  15

Trp Ala Phe Pro
            20
```

TAILORED COMBINATORIAL EPIGENETIC THERAPIES FOR P53 GAIN-OF-FUNCTION TUMORS

CROSS-REFERENCE TO RELATED APPLICATIONS

This application is the U.S. national phase application filed under 35 U.S.C. § 371 claiming benefit to International Patent Application No. PCT/US15/11355, filed Jan. 14, 2015, which is entitled to priority under 35 U.S.C. § 119(e) to U.S. provisional application No. 61/927,311, filed Jan. 14, 2014; 61/931,271, filed Jan. 24, 2014 and 62/010,239, filed Jun. 10, 2014, the disclosures of which are incorporated herein by reference in their entirety.

STATEMENT REGARDING FEDERALLY SPONSORED RESEARCH OR DEVELOPMENT

This invention was made with government support under 5RO1CA078831-15, awarded by the National Institutes of Health (NIH). The government has certain rights in the invention.

BACKGROUND OF THE INVENTION

Mutations in p53 occur in more than 50% of all human tumors. The majority of p53 mutations are missense point mutations, where single codons are mutated. The result of the majority of the missense mutations is the expression of full-length, but mutated, p53 protein. Many missense mutations fall within the so-called "hot spot" regions; regions within the p53 genomic sequence that are commonly mutated. Most hot spot mutations fall within the DNA binding domain of p53 protein. p53 is often thought to play a role in tumor suppression, however there has recently been accumulating evidence that some hot spot p53 mutations not only abolishes wild-type p53 tumor suppressive function, but also induces "gain-of-function." This gain of function is thought to promote tumor development or progression, suggesting that certain p53 mutations (p53 GOF mutations) may result in the formation or growth of tumors. However, the mechanism of how p53 GOF mutations induce tumor growth at the level of gene expression is not understood. One potential mechanism involves p53 GOF mutant directly binding to inappropriate DNA sequences and spuriously activating gene expression. Another mechanism involves p53 GOF mutants that completely lose the ability to bind DNA. Instead, p53 GOF can interact with other DNA binding factors and promote spurious activation of transcription, leading to tumorigenesis.

Thus, there is a need in the art for compositions and methods for treating tumors harboring p53 GOF mutations. The present invention satisfies this unmet need.

SUMMARY OF THE INVENTION

In one aspect, the present invention provides a composition for treating cancer associated with a p53 gain of function (GOF) mutation in a subject, where the composition comprises at least one inhibitor of an epigenetic regulator. In one embodiment, the epigenetic regulator is at least one of the group consisting of MLL1, MLL2, MOZ, menin, and WDR5. In one embodiment, the inhibitor is selected from the group consisting of a nucleic acid, a siRNA, an antisense nucleic acid, a ribozyme, a peptide, a small molecule, an antagonist, an aptamer, and a peptidomimetic. In one embodiment, the p53 GOF mutation is at least one selected from the group consisting of R248Q, R248W, R249S, and R273H.

In one embodiment, the inhibitor inhibits the interaction between an MLL and menin. In one embodiment, the inhibitor is MI-2-2 or a derivative or analogue thereof. In one embodiment, the inhibitor is at least one compound of formula I:

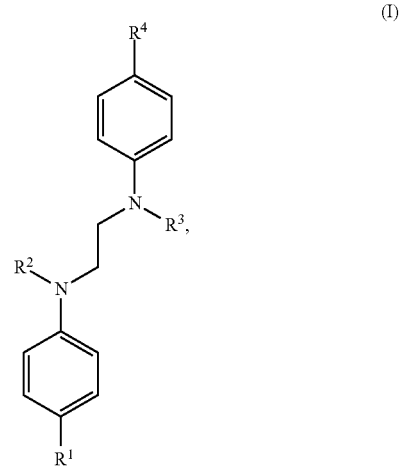

wherein in formula (I):

$R^1$ and $R^4$ are each independently selected from the group consisting of hydrogen, halogen, $NR^aR^b$, hydroxyl, linear or branched $C_1$-$C_6$ alkyl, linear or branched $C_2$-$C_6$ alkenyl, linear or branched $C_2$-$C_6$ alkynyl, $C_3$-$C_8$ cycloalkyl, $C_3$-$C_8$ cycloalkenyl, and $C_1$-$C_6$ alkoxy, wherein said alkyls, alkenyls, alkynyls, cycloalkyls, cycloalkenyls and alkoxys of $R^1$ and $R^4$ are unsubstituted or substituted with at least one halogen;

$R^a$ and $R^b$ are each independently selected from the group consisting of hydrogen, linear or branched $C_1$-$C_4$ alkyl, linear or branched $C_2$-$C_4$ alkenyl, $C_2$-$C_4$ alkynyl, $C_3$-$C_6$ cycloalkyl, and $C_3$-$C_6$ cycloalkenyl, wherein said alkyls, alkenyls, alkynyls, cycloalkyls, cycloalkenyls of $R^a$ and $R^b$ are unsubstituted or substituted with at least one halogen; and $R^2$ and $R^3$ are each independently selected from group consisting of hydrogen, linear or branched $C_1$-$C_6$ alkyl, linear or branched $C_2$-$C_6$ alkenyl, linear or branched $C_2$-$C_6$ alkynyl, $C_3$-$C_8$ cycloalkyl, and $C_3$-$C_8$ cycloalkenyl, wherein said alkyls, alkenyls, alkynyls, cycloalkyls, cycloalkenyls of $R^2$ and $R^3$ are unsubstituted or substituted with at least one halogen, a salt, solvate, or N-oxide thereof, and any combinations thereof.

In one embodiment, the inhibitor is N,N'-bis(4-aminophenyl)-N,N'-dimethylethylenediamine (ISC-30)

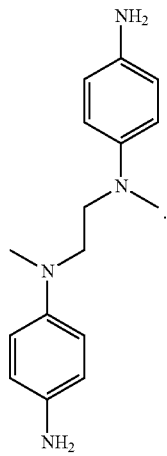 [SMILES: CN(CCN(C)c1ccc(N)cc1)c1ccc(N)cc1]

In one embodiment, the inhibitor inhibits the interaction between an MLL and WDR5. In one embodiment, the inhibitor is OICR-9429, or a derivative or analogue thereof.

In certain embodiments, the cancer is selected from the group consisting of carcinomas, sarcomas, lymphomas, leukemia, blastomas, germ cell cancers, breast cancer, lung cancer, pancreatic cancer, stomach cancer, bone cancer, ovarian cancer, prostate cancer, bladder cancer, cervical cancer, colon cancer, skin cancer, gliomas, esophageal cancer, oral cancer, gallbladder cancer, liver cancer, testicular cancer, uterine cancer, thyroid cancer, throat cancer, Li-Fraumeni Syndrome and a combination thereof.

In one aspect, the present invention provides a method of treating or preventing cancer associated with a p53 gain of function (GOF) mutation in a subject. The method comprises administering to the subject an effective amount of a composition comprising at least one inhibitor of an epigenetic regulator. In one embodiment, the epigenetic regulator is at least one of the group consisting of MLL1, MLL2, MOZ, menin, and WDR5. In one embodiment, the inhibitor is selected from the group consisting of a nucleic acid, a siRNA, an antisense nucleic acid, a ribozyme, a peptide, a small molecule, an antagonist, an aptamer, and a peptidomimetic. In one embodiment, the p53 GOF mutation is at least one selected from the group consisting of R248Q, R248W, R249S, and R273H.

In one embodiment, the inhibitor inhibits the interaction between an MLL and menin. In one embodiment, the inhibitor is MI-2-2 or a derivative or analogue thereof. In one embodiment, the inhibitor is at least one compound of formula I. In one embodiment, the inhibitor is N,N'-bis(4-aminophenyl)-N,N'-dimethylethylenediamine (ISC-30). In one embodiment, the inhibitor inhibits the interaction between an MLL and WDR5. In one embodiment, the inhibitor is OICR-9429, or a derivative or analogue thereof.

In certain embodiments, the cancer is selected from the group consisting of carcinomas, sarcomas, lymphomas, leukemia, blastomas, germ cell cancers, breast cancer, lung cancer, pancreatic cancer, stomach cancer, bone cancer, ovarian cancer, prostate cancer, bladder cancer, cervical cancer, colon cancer, skin cancer, gliomas, esophageal cancer, oral cancer, gallbladder cancer, liver cancer, testicular cancer, uterine cancer, thyroid cancer, throat cancer, Li-Fraumeni Syndrome and a combination thereof.

In one aspect, the present invention provides a personalized method of treating or preventing cancer in a subject. The method comprises detecting a p53 gain of function (GOF) mutation in a tumor cell of the subject, and administering to the subject an effective amount of a composition comprising at least one inhibitor of an epigenetic regulator, wherein the at least one inhibitor is dependent upon the detected p53 GOF mutation. In one embodiment, the epigenetic regulator is at least one of the group consisting of MLL1, MLL2, MOZ, menin, and WDR5. In one embodiment, the inhibitor is selected from the group consisting of a nucleic acid, a siRNA, an antisense nucleic acid, a ribozyme, a peptide, a small molecule, an antagonist, an aptamer, and a peptidomimetic. In one embodiment, the p53 GOF mutation is at least one selected from the group consisting of R248Q, R248W, R249S, and R273H.

In one embodiment, the inhibitor inhibits the interaction between an MLL and menin. In one embodiment, the inhibitor is MI-2-2 or a derivative or analogue thereof. In one embodiment, the inhibitor is at least one compound of formula I. In one embodiment, the inhibitor is N,N'-bis(4-aminophenyl)-N,N'-dimethylethylenediamine (ISC-30). In one embodiment, the inhibitor inhibits the interaction between an MLL and WDR5. In one embodiment, the inhibitor is OICR-9429, or a derivative or analogue thereof.

In certain embodiments, the cancer is selected from the group consisting of carcinomas, sarcomas, lymphomas, leukemia, blastomas, germ cell cancers, breast cancer, lung cancer, pancreatic cancer, stomach cancer, bone cancer, ovarian cancer, prostate cancer, bladder cancer, cervical cancer, colon cancer, skin cancer, gliomas, esophageal cancer, oral cancer, gallbladder cancer, liver cancer, testicular cancer, uterine cancer, thyroid cancer, throat cancer, Li-Fraumeni Syndrome and a combination thereof.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1, comprising FIG. 1A depicts the results of ChIP-seq experiments demonstrating that histone modifying enzymes are regulated by p53 GOF mutants. FIG. 1B depicts tracks of wildtype and mutant p53 ChIP-seq experiments for 3 genomic locations (p21, mll1 and moz). FIG. 1C depicts the results of an experiment using qPCR to validate p53 targets in MDA468 cells. FIG. 1D depicts the results of an experiment using qPCR to demonstrate that p53 GOF (R273H) in a pancreatic cell cancer line (Panc1) also targets epigenetic regulators. FIG. 1E depicts the results of an experiment using qPCR to demonstrate that wildtype p53 does not bind to the epigenetic targets.

FIG. 2, comprising FIG. 2A depicts the general comparison between wildtype and mutant p53 binding to different genomic regions. FIG. 2B depicts the results of motif analysis of mutant (TSS proximal) peaks.

FIG. 4, comprising FIG. 4A through FIG. 4C, depicts the results of experiments demonstrating the functional outcomes of the p53 GOF mutant-induced regulation of epigenetic pathways. FIG. 4A depicts western blots depicting changes in histone modification (H3K4me3 and H3K9ac) in MDA468 cell line in response to control or p53 knockdown. FIG. 4B depicts the change in the abundance of H3K4me3 and H3K9ac following p53 GOF mutant knockdown, as well as the functional implication that the Rho and Ras pathways are most affected by p53 GOF mutant knockdown. FIG. 4C depicts a set of growth curves demonstrating that knockdown of p53 GOF mutant, MLL1, and MLL2 reduces cell growth.

FIG. 5, comprising

FIG. 6, comprising (FIG. 6A) Area under the curve, meta-peak analysis showing the p53 ChIP-seq signal enrichment in all five cell lines over p53 promoter peak regions (10kb upstream of nearest TSS) in MCF7 (left) and MDA-MB-175VII (right). Mann-Whitney tests were performed to compute significance of p53/input enrichment for combined WT vs. combined GOF p53 peaks: MCF7 ($p=2.78\times10^{-6}$), MDA-MB-175VII ($p=2.15\times10^{-4}$). (FIG. 6B) Same analysis as in (FIG. 6A), showing the ChIP-seq signal enrichment in all five cell lines over MDA-MB-468 (left), HCC70 (middle) and BT-549 (right) TSS proximal peaks. Statistical tests were performed as in (FIG. 6A): MDA-MB-468 ($p<2.2\times10^{-16}$), HCC70 ($p=1.09\times10^{-3}$), BT-549 ($p=3.7\times10^{-5}$). (FIG. 6C) Western blot analysis, co-immunoprecipitation of HEK293T cell expressed Flag-ETS2 with in vitro expressed GFP (negative control), HA tagged WT or GOF p53. (FIG. 6D) & (FIG. 6E) Gene Ontology analysis of WT p53 in MDA-MB-175VII (FIG. 6D) and p53 R273H in MDA-MB-468 (FIG. 6E) TSS proximal peaks (statistical significance at p-value <0.05 and FDR=1%).

FIG. 7, comprising (FIG. 7E) ChIP-qPCR validation of GOF p53 binding in MDA-MB-468 cells. Results shown as input normalized p53 (DO-1 mono-clonal antibody, black bars) or IgG (grey bars) ChIP values. Primers were designed to target peak regions and approximately 1kb upstream or 1kb downstream from peak regions of mll1, mll2 and moz genes. WT p53 binding site (BS) at p21 gene was used as a negative control. A schematic of primer locations can be found in FIG. 12E. (FIG. 7F) Similar analysis as in (FIG. 7E), with a p53, poly-clonal antibody FL393 and rabbit IgG control. (FIG. 7G) & (FIG. 7H) ChIP-qPCR analysis of WT p53 binding pattern at epigenetic regulator genes in MDA-MB-175VII cells, as shown with either DO-1 antibody (FIG. 7G) or FL393 antibody (FIG. 7H). (FIG. 7I) Similar ChIP-qPCR analysis as in (FIG. 7E), GOF p53 binding at epigenetic regulators in pancreatic cancer line PANC-1. (FIG. 7J) ChIP-qPCR analysis of GOF p53 occupancy changes at epigenetic regulators under shRNA-mediated p53 knockdown condition. (FIG. 7K) ChIP-qPCR analysis of GOF p53 occupancy changes at epigenetic regulators under shRNA-mediated ETS2 knockdown condition. #21 and #20 denote two different short hairpins targeting ETS2. (FIG. 7L) ChIP-qPCR analysis of p53 binding in MEFs with p53 WT or p53 R172H. (All error bars represent standard deviation from the mean of three biological replicates. Two sample t-tests were used to compute the significance: *, p-value<0.05; , p-value<0.01; *, p-value<0.001)

FIG. 8, comprising (FIG. 8A) & (FIG. 8B) mRNA expression level changes upon shRNA-mediated p53 knockdown, measured by qPCR following reverse transcription (RT-qPCR) in (FIG. 8A) MDA-MB-468 or (FIG. 8B) MDA-MB-175VII cells. (FIG. 8C) Western blot analysis of MLL1 protein level changes upon shRNA-mediated p53 knockdown, in MDA-MB-468 (left) and MDA-MB-175VII (right) cells. (FIG. 8D) RT-qPCR analysis measuring mRNA expression level changes upon shRNA-mediated ETS2 knockdown in MDA-MB-468 cells. (FIG. 8E) RT-qPCR analysis measuring mRNA expression levels in MEFs with p53 WT or p53 R172H. (FIG. 8F) Western blot analysis of MLL1 protein levels in p53 WT MEFs and p53 R172H MEFs. (FIG. 8G) RT-qPCR analysis measuring mRNA expression level changes upon p53 knockdown in MEFs with GOF p53 R172H. (FIG. 8H) Western blot analysis of MLL1 protein level changes upon shRNA-mediated p53 knockdown in MEFs with GOF p53 R172H. #54549 and #12359 denote two different hairpins targeting mouse p53. (FIG. 8I) Western blot analysis of MLL1 protein level change upon retroviral overexpression of GOF p53 R172H in MEFs with p53 knockout. (FIG. 8J) Western blot analysis of H3K4me3 and H3K9ac level differences between MEFs with WT p53 or GOF p53 R172H. (FIG. 8K) Box plot analysis of RNA levels (left) and H3 normalized H3K4me3 levels (right) at previously discovered MLL1 target genes compared with all genes, from RNA-seq and H3K4me3 ChIP-seq of MEFs with WT p53 or GOF p53 R172H. Plot is presented as ratios of GOF p53 R172H values over WT p53 values. Wilcoxon tests were used to compute the significance: , p-value<0.01; *, p-value<0.001. (FIG. 8L) Track views of H3K4me3 enrichment (up) and RNA levels (down) across Hoxa gene cluster, from H3K4me3 ChIP-seq and RNA-seq of MEFs with WT p53 or GOF p53 R172H. Tracks are presented as overlay of WT p53 and GOF p53 signals. Blue denotes more enriched in WT p53, red denotes more enriched in GOF p53 R172H, black denotes overlap. (FIG. 8M) Box plot analysis of RNA levels (left) and H3 normalized H3K4me3 levels (right) at Hoxa cluster genes compared with all genes, from RNA-seq and H3K4me3 ChIP-seq of MEFs with WT p53 or GOF p53 R172H. Plot is presented as ratios of GOF p53 R172H values over WT p53 values. Wilcoxon tests were used to compute the significance: *, p-value<0.05; **, p-value<0.01. (All error bars represent standard deviation from the mean of three biological replicates. Two sample t-tests were used to compute the significance unless specified: *, p-value<0.05; , p-value<0.01; *, p-value<0.001)

FIG. 9, comprising

(FIG. 9A) & (FIG. 9B) Growth curve analysis of (FIG. 9A) MDA-MB-468 and (FIG. 9B) MDA-Mb-175VII cells with either non-targeting control shRNA or p53 shRNA knockdown. (FIG. 9C) & (FIG. 9D) Growth curve analysis of (FIG. 9C) MDA-MB-468 and (FIG. 9D) MDA-Mb-175VII cells with non-targeting control shRNA, mll1 shRNA, or mll2 shRNA knockdown. (FIG. 9E) Colony-formation assay of MDA-MB-468 cells with either non-targeting control shRNA (left up) or mll1 shRNA (left down) knockdown, and quantification by crystal violet staining (right). (FIG. 9F) Anchorage-independent soft agar assay of MDA-MB-468 cells with either non-targeting control shRNA (left up) or mll1 shRNA (left down) knockdown. Dashed boxes (middle) denote enlarged images of the selected areas. Arrows indicate visible colonies. Quantifications (right) are shown as number of visible colonies. (FIG. 9G) Colony-formation assay of MCF7 cells with either non-targeting control shRNA (left up) or mll1 shRNA (left down) knockdown, and quantification by crystal violet staining (right). (FIG. 9H) Anchorage-independent soft agar assay of MCF7 cells with either non-targeting control shRNA (left up) or mll1 shRNA (left down) knockdown. Dashed boxes (middle) denote enlarged images of the selected areas. Quantifications (right) are shown as number of visible colonies. (FIG. 9I) Xenograft tumor growth in immune-deficient mice, shown as tumor volumes three weeks after mice were injected with either MCF7 or MDA-MB-468 cells, with short hairpins of either non-targeting control or MLL1. In this calculation, palpable tumors smaller than 4 mm$^3$ were recorded as 4 mm$^3$ due to difficulties in measurement. Zeros indicate that the mouse did not have palpable tumor. Red lines are shown as average tumor volume of all eight mice in each group. (FIG. 9J) & (FIG. 9K) Growth curve analysis of (FIG. 9J) MDAH087 and (FIG. 9K) MDAH041 cells with either non-targeting control shRNA or mll1 shRNA knockdown. (FIG. 9L) Growth curve analysis of IMR90 cells with either non-targeting control shRNA or mll1 shRNA knockdown. (All error bars represent standard deviation from the mean of three biological replicates. Two sample t-tests were used to compute the significance: *, p-value<0.05; , p-value<0.01; *, p-value<0.001)

FIG. 10, comprising (FIG. 10A) Endogenous co-IP of Menin and MLL1 in LFS MDAH087 cells upon treatment of DMSO or different concentrations of ISC-30. (FIG. 10B) & (FIG. 10C) Growth curve analysis of LFS (FIG. 10B) MDAH087 and (FIG. 10C) MDAH041 cells treated with DMSO, 2.504 or 7.504 ISC-30 Menin inhibitor. (FIG. 10D) & (FIG. 10E) Growth curve analysis of LFS (FIG. 10D) MDAH087 and (FIG. 10E) MDAH041 cells treated with DMSO, 1004, or 20 µM MI-2-2 Menin inhibitor. (FIG. 10F) and (FIG. 10G) Growth curve analysis of LFS (FIG. 10F) MDAH087 and (FIG. 10G) MDAH041 cells treated with DMSO, 2 µM, or 4 µM OICR-9429 WDR5 inhibitor. (All error bars represent standard deviation of three biological replicates.)

FIG. 11, comprising (FIG. 11A) Heatmap analysis showing the enrichment of p53 peaks (+/−2500 bp around peak center) identified from each cell line (rows) in all five cell lines (columns) examined by ChIP-seq. (FIG. 11B-FIG. 11E) Area under the curve, meta-peak analysis showing GOF p53 and IgG ChIP-seq (Scian et al. 2004, Cancer Res, 65: 7447-7454) signal enrichment in MDAH087 cells over TSS proximal peaks of (FIG. 11B) MCF7, (FIG. 11C) MDA-MB-175VII, (FIG. 11D) MDA-MB-468, and (FIG. 11E) HCC70. (FIG. 11F) & (FIG. 11G) Endogenous co-IP of ETS2 and (FIG. 11E) GOF p53 or (FIG. 11F) WT p53 in (FIG. 11E) MDA-MB-468 or (FIG. 11F) MCF7 cells. (FIG. 11H) Motif analysis of all TSS proximal peaks in MDA-MB-468 predicted by MEME/TomTom (middle), and SeqPos (down), and compared with canonical ETS motif (up). (FIG. 11D MEME/TomTom discovered WT p53 motif from MDA-MB-175VII TSS proximal peaks. (FIG. 11J) MDA-MB-468, (FIG. 11K) HCC70, (FIG. 11L) MCF7, and (FIG. 11M) MDA-MB-175VII, showing overlap of TSS proximal or TSS distal (more than 10kb away from gene TSS) peaks with known ETS peaks from multiple cell lines as indicated; or overlap with "at least one" cell line.

FIG. 12, comprising (FIG. 12H) ChIP-qPCR validation of GOF p53 binding at rbbp5 in MDA-MB-468 cells. (FIG. 12I) Schematic of amplicon locations for ChIP-qPCR validation in FIG. 7E. (FIG. 12J-FIG. 12M) Re-aligned GOF p53 and IgG ChIP-seq data in MDAH087 cells (Do et al., 2012, Genes Dev., 26(8):830-45), showing enrichment of GOF p53 at promoter regions of (FIG. 12J) mll1, (FIG. 12K) mll2, and (FIG. 12L) moz, as well as (FIG. 12M) tdp2 gene as a positive control (Do et al., 2012, Genes Dev., 26(8):830-45). (All error bars represent standard deviation from the mean of three biological replicates. Two sample t-tests were used to compute the significance: *, p-value<0.05; , pvalue<0.01; *, p-value<0.001)

FIG. 13, comprising (FIG. 13A) RT-qPCR analysis of mRNA expression level changes upon siRNA-mediated GOF p53 knockdown in MDA-MB-468 cells. (FIG. 13B) RT-qPCR analysis of mRNA expression level changes upon DMSO or Nutlin treatment in MCF7 cells. (FIG. 13C) Western blot analysis of MLL1 protein levels upon DMSO or Nutlin treatment in MCF7 cells. (FIG. 13D) Western blot analysis of MOZ protein level change upon shRNA-mediated GOF p53 knockdown in MDA-MB-468 cells. (FIG. 13E) Western blot analysis of MLL1 protein level change upon shRNA-mediated ETS2 FIG. 13 knockdown in MDA-MB-468 cells. (FIG. 13F) Western blot analysis of H3K9ac and H3K4me3 levels in MDA-MB-468 cells upon non-targeting siRNA or p53 siRNA knockdown. (FIG. 13G) Western blot analysis of histone methylation and acetylation level changes upon shRNA-mediated knockdown of GOF p53 in MDA-MB-468 cells. (FIG. 13H) Western blot analysis of methylation and acetylation levels at indicated histone H3 residues, upon non-targeting control shRNA or p53 shRNA knockdown in MDA-MB-468 cells. (FIG. 13I) Western blot analysis of H3K9ac change upon shRNA-mediated moz knockdown in MDA-MB-468 cells. (FIG. 13J) Western blot analysis of H3K9ac and H3K4me3 levels in PANC-1 cells upon shRNA-mediated GOF p53 knockdown. (FIG. 13K) RT-qPCR analysis of mRNA expression levels upon retroviral expression of GOF p53 R172H in MEFs with p53 knockout. (FIG. 13L) Track views of H3K4me3 enrichment (up) and RNA levels (down) across p21, from H3K4me3 ChIP-seq and RNA-seq of MEFs with WT p53 or GOF p53 R172H. Tracks are presented as overlay of WT p53 and GOF p53 signals. Blue denotes more enriched in WT p53, red denotes more enriched in GOF p53 R172H, black denotes overlap. (FIG. 13M) Box plot analysis of H3 normalized H3K4me3 levels, from H3K4me3 ChIP-seq of MEFs with WT p53 or GOF p53 R172H. Wilcoxon test was used to compute the significance: ***, p-value<0.001. (All error bars represent standard deviation from the mean of three biological replicates. Two sample t-tests were used to compute the significance unless specified: *, p-value<0.05; , p-value<0.01; *, p-value<0.001)

FIG. 14, comprising (FIG. 14A) Growth curve analysis of MCF7 cells with non-targeting control shRNA, mll1 shRNA, or mll2 shRNA knockdown. (FIG. 14B) Colony-formation assay of MDA-MB-468 cells with either non-targeting control shRNA (up) or mll1 shRNA (down) knockdown, the other two replicates of the experiment in FIG. 9E. (FIG. 14C) Colony-formation assay of MCF cells with either non-targeting control shRNA (up) or mll1 shRNA (down) knockdown, the other two replicates of the experiment in FIG. 9G. (FIG. 14D) Anchorage-independent soft agar assay of MDA-MB-468 cells with either non-targeting control shRNA (up) or mll1 shRNA (down) knockdown, the other two replicates of the experiment in FIG. 9F. (FIG. 14E) Anchorage-independent soft agar assay of MCF7 cells with either non-targeting control shRNA (up) or mll1 shRNA (down) knockdown, the other two replicates of the experiment in FIG. 9H. (FIG. 14F) Western blot analysis of p53 protein levels in LFS MDAH087 and MDAH041 cells. (FIG. 14G) Western blot analysis of MLL1 levels upon shRNA-mediated knockdown in LFS MDAH087 and MDAH041 cells. (FIG. 14H) & (FIG. 14I) Growth curve analysis of (FIG. 14H) MDAH087 and (FIG. 14I) MDAH041 cells with either non-targeting control shRNA or mll1 shRNA knockdown. The short hairpin used here is different from the one used in FIG. 9I and FIG. 9J. (FIG. 14J) & (FIG. 14K) Growth curve analysis of (FIG. 14J) MDAH087 and (FIG. 14K) MDAH041 cells with either non-targeting control shRNA or mll2 shRNA knockdown. (FIG. 14L) Western blot analysis of MLL1 levels upon two different shRNA-mediated knockdown in IMR90 cells. (FIG. 14M) Tumor incidence as measured by number of mice (out of 8 mice in each group) with visible tumors 3 weeks after subcutaneous injection.

FIG. 15, comprising (FIG. 15A) Chemical structure of ISC-30 compound [N,N'-bis(4-aminophenyl)-N,N'-dimethylethylenediamine]. (CID: 193110, NCI: 129674, Chemical formula: C16H22N4 Molecular weight: 270.37) (FIG. 15B) His-SUMO-MeninΔ460-519 (Menin) was titrated into wells containing fluorescence polarization buffer and FITC-MLL peptide (1.5 nM) to allow fluorescence polarization monitoring and calculation of the binding affinity. (FIG. 15C) Wild-type (WT) or Mutant (Mut) competitor MLL peptides were titrated into wells containing fluorescence polarization butter, His-SUMO-MeninΔ460-519 (5 nM), and FITC-MLL peptide (1.5 nM) and the inhibition of fluorescence polarization was monitored and utilized to normalize the ISC30 inhibition. All measurements were blanked by subtracting the background signal taken from wells containing only buffer. mP=millipolarization. (FIG. 15D) Peptide displacement assay measuring ISC-30 inhibition of menin-MLL1 interaction by the decrease in fluorescence polarization (FP) signal of a FITC labeled MLL1 peptide upon ISC-30 induced dissociation from menin. (FIG. 15E) HoxA5 and HoxA9 mRNA levels after 2 days of ISC-30 or DMSO (vehicle control) treatment in AT-1 cells (mouse MLL-AF9 leukemia cell line). (FIG. 15F) Growth analysis of AT-1 cells treated with DMSO or 10 μM ISC-30. (FIG. 15G) Endogenous co-IP of Menin and MLL1 in LFS MDAH041 cells upon treatment of DMSO or different concentrations of ISC-30.

FIG. 16, FIG. 16A through FIG. 16D, depicts the results of experiments. (FIG. 16A) Histogram plot, number of genes against H3K4me3 signal changes upon GOF p53 knockdown. H3K4me3 signal represents 1kb region around gene TSS, after total histone H3 normalization. (FIG. 16B) GO analysis of genes with top 5% changes in H3K4me3 signal upon GOF p53 knockdown. (FIG. 16C) Track view representations of H3K4me3 signal at genes from the rho/ras signaling GO category, arhgef2, syde2 and smap2. (All error bars represent standard deviation from the mean of three biological replicates.) (FIG. 16D) H3K4me3 ChIP-seq signal changes upon GOF p53 knockdown at TSS region of rho/ras pathway genes.

DETAILED DESCRIPTION

Figure 1A:
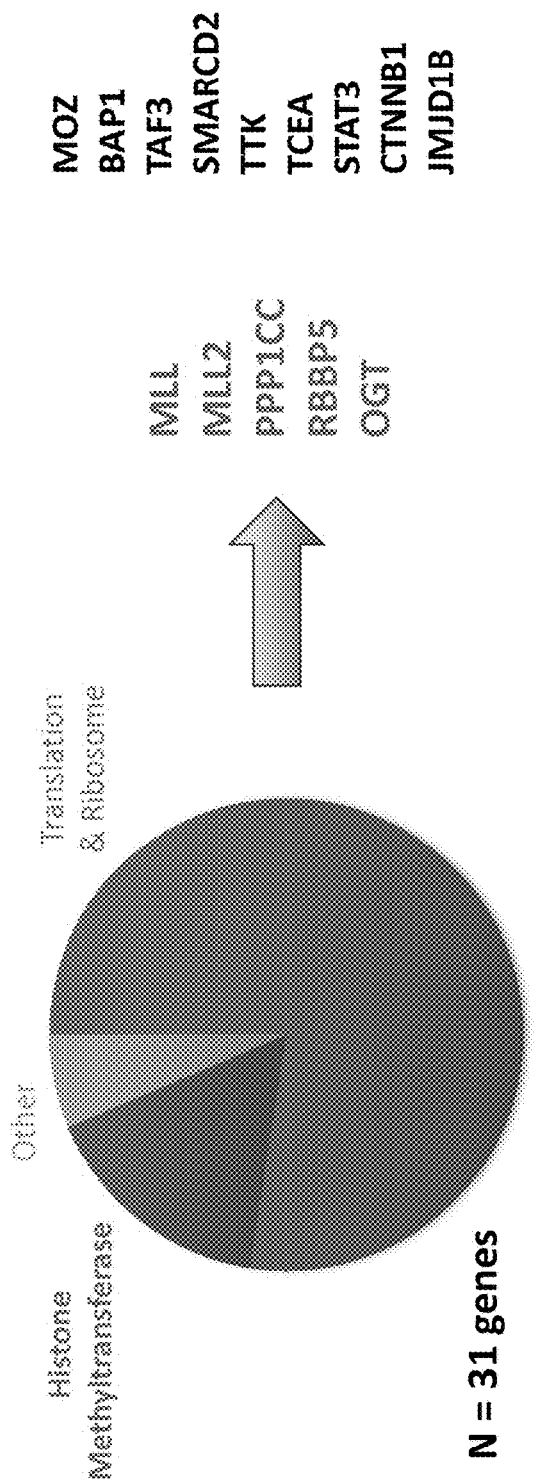
FIG. 1A through FIG. 1E, depicts the results of experiments demonstrating that epigenetic targets stand out as mutant p53 targets.
Figure 1A:
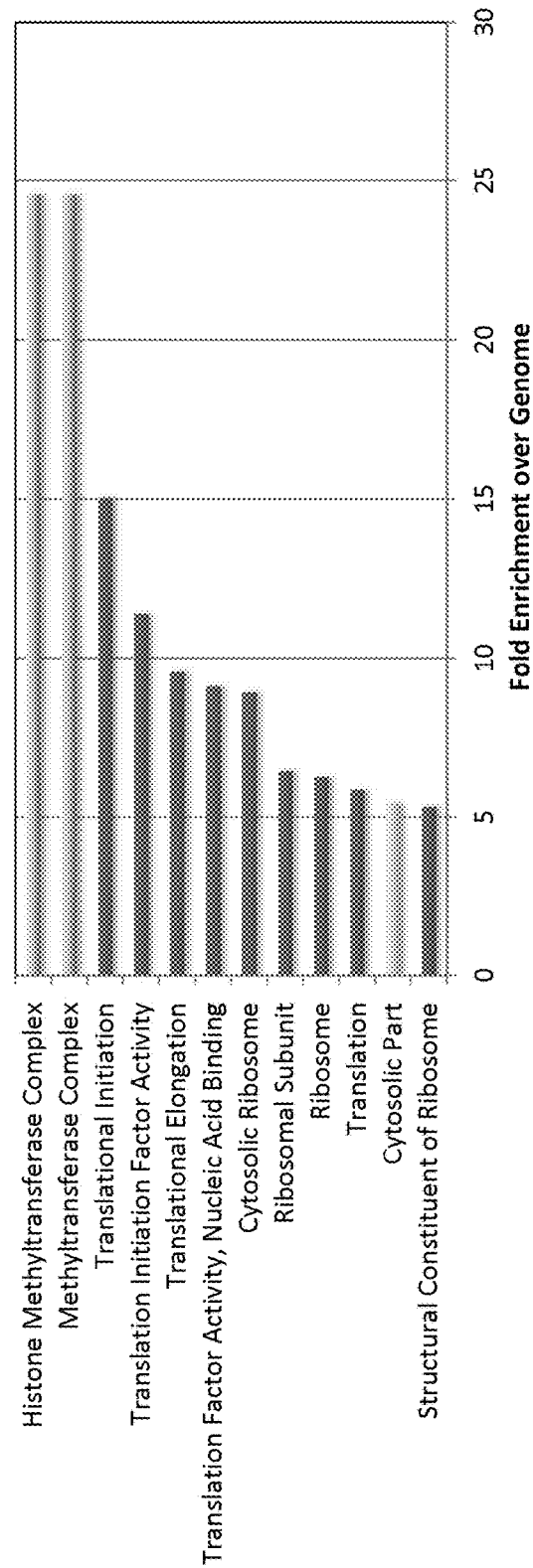

The present invention relates generally to compositions and methods for treating cancer. The invention is useful, for example, for reducing tumor growth and tumor cell proliferation. In certain embodiments, the invention provides for a personalized treatment of a cancer dependent upon the epigenetic signature of the cancer. In certain embodiments, the present invention treats or prevents any cancer or tumor associated with p53 gain of function (GOF) mutations. In one embodiment, the invention relates to the targeting of one or more epigenetic pathways that are regulated by p53 GOF mutation harboring tumors.

In one embodiment, the present invention provides a composition for treating cancer in a subject. In one embodiment, the composition comprises an inhibitor of an epigenetic regulator, for example a histone modifying enzyme. For example, in certain embodiments, the composition comprises an inhibitor of MLL1 (also known as lysine (K)-specific methyltransferase 2A (KMT2A)), MLL2 (also known as lysine (K)-specific methyltransferase 2D (KMT2D)), MOZ (also known as lysine (K) acetyltranferase 6A (KAT6A)), or a combination thereof.

In one embodiment, the present invention provides a method for treating or preventing cancer. In one embodiment, the method comprises administering to a subject an effective amount of a composition comprising an inhibitor of MLL1, an inhibitor of MLL2, an inhibitor of MOZ, or a combination thereof. In certain embodiments, the method comprises administering to a subject an effective amount of a composition comprising an inhibitor of MLL1, an effective amount of a composition comprising an inhibitor of MLL2, and an effective amount of a composition comprising an inhibitor of MOZ. In some instances, the method is specifically tailored or targeted to the signature of the tumor. For example, in certain instances the method is targeted to a particular p53 GOF mutation, thereby providing a personalized therapy.

In certain instances, the MLL enzymes are components of several multi-subunit protein complexes. In one embodiment, the composition of the invention comprises an inhibitor of at least one member of a complex comprising MLL1, MLL2, or MOZ. In one embodiment, the composition comprises an inhibitor of MLL1, MLL2, MOZ, menin, WD repeat-containing protein 5 (WDR5), or a combination thereof.

In one embodiment, the composition comprises an inhibitor of an interaction in a complex comprising MLL1, MLL2, or MOZ. For example, in one embodiment, the composition comprises an inhibitor of the interaction between an MLL and menin. In one embodiment, the composition comprises an inhibitor of the interaction between an MLL and WDR5.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

Generally, the nomenclature used herein and the laboratory procedures in cell culture, molecular genetics, organic chemistry, and nucleic acid chemistry and hybridization are those well-known and commonly employed in the art.

Standard techniques are used for nucleic acid and peptide synthesis. The techniques and procedures are generally performed according to conventional methods in the art and various general references (e.g., Sambrook and Russell, 2012, Molecular Cloning, A Laboratory Approach, Cold Spring Harbor Press, Cold Spring Harbor, N.Y., and Ausubel et al., 2002, Current Protocols in Molecular Biology, John Wiley & Sons, NY), which are provided throughout this document.

The nomenclature used herein and the laboratory procedures used in analytical chemistry and organic syntheses described below are those well known and commonly employed in the art. Standard techniques or modifications thereof, are used for chemical syntheses and chemical analyses.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

"Antisense" refers particularly to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences.

As used herein, "aptamer" refers to a small molecule that can bind specifically to another molecule. Aptamers are typically either polynucleotide- or peptide-based molecules. A polynucleotide aptamer is a DNA or RNA molecule that adopts a highly specific three-dimensional conformation designed to have appropriate binding affinities and specificities towards specific target molecules, such as peptides, proteins, drugs, vitamins, among other organic and inorganic molecules. Such polynucleotide aptamers can be selected from a vast population of random sequences through the use of systematic evolution of ligands by exponential enrichment. A peptide aptamer is typically a loop of about 10 to about 20 amino acids attached to a protein scaffold that binds to specific ligands. Peptide aptamers may be identified and isolated from combinatorial libraries, using methods such as the yeast two-hybrid system.

The phrase "bodily sample" as used herein, means any sample comprising a cell, a tissue, or a bodily fluid in which expression of a gene or gene product (e.g. p53) can be detected. Samples that are liquid in nature are referred to herein as "bodily fluids." Bodily samples may be obtained from a patient by a variety of techniques including, for example, by scraping or swabbing an area or by using a needle to aspirate bodily fluids. Methods for collecting various bodily samples are well known in the art.

The term "cancer" as used herein is defined as disease characterized by the rapid and uncontrolled growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like.

"Complementary" as used herein refers to the broad concept of subunit sequence complementarity between two nucleic acids, e.g., two DNA molecules. When a nucleotide position in both of the molecules is occupied by nucleotides normally capable of base pairing with each other, then the nucleic acids are considered to be complementary to each other at this position. Thus, two nucleic acids are substantially complementary to each other when at least about 50%, preferably at least about 60% and more preferably at least about 80% of corresponding positions in each of the molecules are occupied by nucleotides which normally base pair with each other (e.g., A:T and G:C nucleotide pairs).

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity or frequency of at least one sign or symptom of the disease or disorder experienced by a patient is reduced.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

The terms "effective amount" and "pharmaceutically effective amount" refer to a nontoxic but sufficient amount of an agent to provide the desired biological result. That result can be reduction and/or alleviation of the signs, symptoms, or causes of a disease or disorder, or any other desired alteration of a biological system. An appropriate effective amount in any individual case may be determined by one of ordinary skill in the art using routine experimentation.

As used herein "endogenous" refers to any material from or produced inside an organism, cell, tissue or system.

As used herein, the term "exogenous" refers to any material introduced from or produced outside an organism, cell, tissue or system.

The term "expression" as used herein is defined as the transcription and/or translation of a particular nucleotide sequence driven by its promoter.

The term "expression vector" as used herein refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules, siRNA, ribozymes, and the like. Expression vectors can contain a variety of control sequences, which refer to nucleic acid sequences necessary for the transcription and possibly translation of an operatively linked coding sequence in a particular host organism. In addition to control sequences that govern transcription and translation, vectors and expression vectors may contain nucleic acid sequences that serve other functions as well.

The term "fusion polypeptide" refers to a chimeric protein containing a protein of interest (e.g., luciferase) joined to a heterologous sequence (e.g., a non-luciferase amino acid or protein).

The term "homology" refers to a degree of complementarity. There may be partial homology or complete homology (i.e., identity). Homology is often measured using sequence analysis software (e.g., Sequence Analysis Software Package of the Genetics Computer Group. University of Wisconsin Biotechnology Center. 1710 University Avenue. Madison, Wis. 53705). Such software matches similar sequences by assigning degrees of homology to various substitutions, deletions, insertions, and other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

The term "isolated" when used in relation to a nucleic acid, as in "isolated oligonucleotide" or "isolated polynucleotide" refers to a nucleic acid sequence that is identified and separated from at least one contaminant with which it is ordinarily associated in its source. Thus, an isolated nucleic acid is present in a form or setting that is different from that in which it is found in nature. In contrast, non-isolated nucleic acids (e.g., DNA and RNA) are found in the state they exist in nature. For example, a given DNA sequence (e.g., a gene) is found on the host cell chromosome in proximity to neighboring genes; RNA sequences (e.g., a specific mRNA sequence encoding a specific protein), are found in the cell as a mixture with numerous other mRNAs that encode a multitude of proteins. However, isolated nucleic acid includes, by way of example, such nucleic acid in cells ordinarily expressing that nucleic acid where the nucleic acid is in a chromosomal location different from that of natural cells, or is otherwise flanked by a different nucleic acid sequence than that found in nature. The isolated nucleic acid or oligonucleotide may be present in single-stranded or double-stranded form. When an isolated nucleic acid or oligonucleotide is to be utilized to express a protein, the oligonucleotide contains at a minimum, the sense or coding strand (i.e., the oligonucleotide may be single-stranded), but may contain both the sense and anti-sense strands (i.e., the oligonucleotide may be double-stranded).

The term "isolated" when used in relation to a polypeptide, as in "isolated protein" or "isolated polypeptide" refers to a polypeptide that is identified and separated from at least one contaminant with which it is ordinarily associated in its source. Thus, an isolated polypeptide is present in a form or setting that is different from that in which it is found in nature. In contrast, non-isolated polypeptides (e.g., proteins and enzymes) are found in the state they exist in nature.

"Naturally-occurring" as applied to an object refers to the fact that the object can be found in nature. For example, a polypeptide or polynucleotide sequence that is present in an organism (including viruses) that can be isolated from a source in nature and which has not been intentionally modified by man is a naturally-occurring sequence.

By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil). The term "nucleic acid" typically refers to large polynucleotides.

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

By "expression cassette" is meant a nucleic acid molecule comprising a coding sequence operably linked to promoter/regulatory sequences necessary for transcription and, optionally, translation of the coding sequence.

The term "operably linked" as used herein refer to the linkage of nucleic acid sequences in such a manner that a nucleic acid molecule capable of directing the transcription of a given gene and/or the synthesis of a desired protein molecule is produced. The term also refers to the linkage of sequences encoding amino acids in such a manner that a functional (e.g., enzymatically active, capable of binding to a binding partner, capable of inhibiting, etc.) protein or polypeptide is produced.

As used herein, the term "promoter/regulatory sequence" means a nucleic acid sequence which is required for expression of a gene product operably linked to the promoter/regulator sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in an inducible manner.

An "inducible" promoter is a nucleotide sequence which, when operably linked with a polynucleotide which encodes or specifies a gene product, causes the gene product to be produced substantially only when an inducer which corresponds to the promoter is present.

A "constitutive" promoter is a nucleotide sequence which, when operably linked with a polynucleotide which encodes or specifies a gene product, causes the gene product to be produced in a cell under most or all physiological conditions of the cell.

"Polypeptide" refers to a polymer composed of amino acid residues, related naturally occurring structural variants, and synthetic non-naturally occurring analogs thereof linked via peptide bonds. Synthetic polypeptides can be synthesized, for example, using an automated polypeptide synthesizer.

The term "protein" typically refers to large polypeptides.

The term "peptide" typically refers to short polypeptides.

Conventional notation is used herein to portray polypeptide sequences: the left-hand end of a polypeptide sequence is the amino-terminus; the right-hand end of a polypeptide sequence is the carboxyl-terminus.

As used herein, a "peptidomimetic" is a compound containing non-peptidic structural elements that is capable of mimicking the biological action of a parent peptide. A peptidomimetic may or may not comprise peptide bonds.

A "polynucleotide" means a single strand or parallel and anti-parallel strands of a nucleic acid. Thus, a polynucleotide may be either a single-stranded or a double-stranded nucleic acid. In the context of the present invention, the following abbreviations for the commonly occurring nucleic acid bases are used. "A" refers to adenosine, "C" refers to cytidine, "G" refers to guanosine, "T" refers to thymidine, and "U" refers to uridine.

The term "oligonucleotide" typically refers to short polynucleotides, generally no greater than about 60 nucleotides. It will be understood that when a nucleotide sequence is represented by a DNA sequence (i.e., A, T, G, C), this also includes an RNA sequence (i.e., A, U, G, C) in which "U" replaces "T."

"Recombinant polynucleotide" refers to a polynucleotide having sequences that are not naturally joined together. An amplified or assembled recombinant polynucleotide may be included in a suitable vector, and the vector can be used to transform a suitable host cell.

A recombinant polynucleotide may serve a non-coding function (e.g., promoter, origin of replication, ribosome-binding site, etc.) as well.

The term "recombinant polypeptide" as used herein is defined as a polypeptide produced by using recombinant DNA methods. A host cell that comprises a recombinant polynucleotide is referred to as a "recombinant host cell." A gene which is expressed in a recombinant host cell wherein the gene comprises a recombinant polynucleotide, produces a "recombinant polypeptide."

As used herein, a "recombinant cell" is a host cell that comprises a recombinant polynucleotide.

By the term "specifically binds," as used herein, is meant a molecule, such as an antibody, which recognizes and binds to another molecule or feature, but does not substantially recognize or bind other molecules or features in a sample.

As used herein, the term "transdominant negative mutant gene" refers to a gene encoding a polypeptide or protein product that prevents other copies of the same gene or gene product, which have not been mutated (i.e., which have the wild-type sequence) from functioning properly (e.g., by inhibiting wild type protein function). The product of a transdominant negative mutant gene is referred to herein as "dominant negative" or "DN" (e.g., a dominant negative protein, or a DN protein).

The phrase "inhibit," as used herein, means to reduce a molecule, a reaction, an interaction, a gene, an mRNA, and/or a protein's expression, stability, function or activity by a measurable amount or to prevent entirely. Inhibitors are compounds that, e.g., bind to, partially or totally block stimulation, decrease, prevent, delay activation, inactivate, desensitize, or down regulate a protein, a gene, and an mRNA stability, expression, function and activity, e.g., antagonists.

As used herein, a "marker gene" or "reporter gene" is a gene that imparts a distinct phenotype to cells expressing the gene and thus permits cells having the gene to be distinguished from cells that do not have the gene. Such genes may encode either a selectable or screenable marker, depending on whether the marker confers a trait which one can 'select' for by chemical means, i.e., through the use of a selective agent (e.g., a herbicide, antibiotic, or the like), or whether it is simply a "reporter" trait that one can identify through observation or testing, i.e., by 'screening'. Elements of the present disclosure are exemplified in detail through the use of particular marker genes. Of course, many examples of suitable marker genes or reporter genes are known to the art and can be employed in the practice of the invention. Therefore, it will be understood that the following discussion is exemplary rather than exhaustive. In light of the techniques disclosed herein and the general recombinant techniques which are known in the art, the present invention renders possible the alteration of any gene.

"Therapeutically effective amount" is an amount of a compound of the invention, that when administered to a patient, ameliorates a symptom of the disease. The amount of a compound of the invention which constitutes a "therapeutically effective amount" will vary depending on the compound, the disease state and its severity, the age of the patient to be treated, and the like. The therapeutically effective amount can be determined routinely by one of ordinary skill in the art having regard to his own knowledge and to this disclosure.

The terms "subject" or "patient" for the purposes of the present invention includes humans and other animals, particularly mammals, and other organisms. Thus the methods are applicable to both human therapy and veterinary applications. In a preferred embodiment the patient is a mammal, and in a most preferred embodiment the patient is human.

The terms "treat," "treating," and "treatment," refer to therapeutic or preventative measures described herein. The methods of "treatment" employ administration to a subject, in need of such treatment, a composition of the present invention, for example, a subject afflicted a disease or disorder, or a subject who ultimately may acquire such a disease or disorder, in order to prevent, cure, delay, reduce the severity of, or ameliorate one or more symptoms of the disorder or recurring disorder, or in order to prolong the survival of a subject beyond that expected in the absence of such treatment.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

As used herein, the term "alkyl," by itself or as part of another substituent means, unless otherwise stated, a straight or branched chain hydrocarbon having the number of carbon atoms designated (i.e. $C_{1-6}$ means one to six carbon atoms) and including straight, branched chain, or cyclic substituent groups. Examples include methyl, ethyl, propyl, isopropyl, butyl, isobutyl, tert-butyl, pentyl, neopentyl, hexyl, and cyclopropylmethyl. Most preferred is ($C_1$-$C_6$)alkyl, particularly ethyl, methyl, isopropyl, isobutyl, n-pentyl, n-hexyl and cyclopropylmethyl.

As used herein, the term "substituted alkyl" means alkyl as defined above, substituted by one, two or three substituents selected from the group consisting of halogen, —OH, alkoxy, —NH$_2$, —N(CH$_3$)$_2$, —C(=O)OH, trifluoromethyl, —C(=O)O($C_1$-$C_4$)alkyl, —C(=O)NH$_2$, —SO$_2$NH$_2$, —C(=NH)NH$_2$, and —NO$_2$, preferably containing one or two substituents selected from halogen, —OH, alkoxy, —NH$_2$, trifluoromethyl, —N(CH$_3$)$_2$, and —C(=O)OH, more preferably selected from halogen, alkoxy and —OH. Examples of substituted alkyls include, but are not limited to, 2,2-difluoropropyl, 2-carboxycyclopentyl and 3-chloropropyl.

As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. Preferred are ($C_1$-$C_3$) alkoxy, particularly ethoxy and methoxy.

As used herein, the term "halo" or "halogen" alone or as part of another substituent means, unless otherwise stated, a fluorine, chlorine, bromine, or iodine atom, preferably, fluorine, chlorine, or bromine, more preferably, fluorine or chlorine.

As used herein, the term "cycloalkyl" refers to a mono cyclic or polycyclic non-aromatic radical, wherein each of the atoms forming the ring (i.e. skeletal atoms) is a carbon atom. In one embodiment, the cycloalkyl group is saturated or partially unsaturated. In another embodiment, the cycloalkyl group is fused with an aromatic ring. Cycloalkyl groups include groups having from 3 to 10 ring atoms. Illustrative examples of cycloalkyl groups include, but are not limited to, the following moieties:

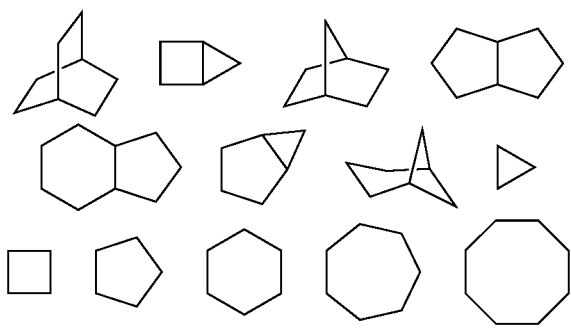

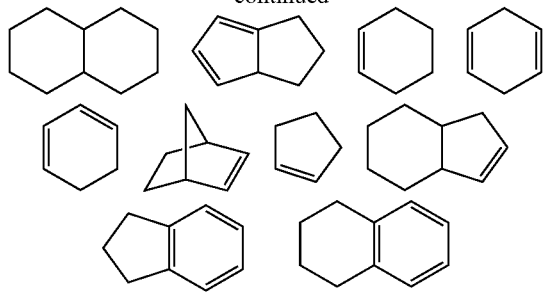

Monocyclic cycloalkyls include, but are not limited to, cyclopropyl, cyclobutyl, cyclopentyl, cyclohexyl, cycloheptyl, and cyclooctyl. Dicyclic cycloalkyls include, but are not limited to, tetrahydronaphthyl, indanyl, and tetrahydropentalene. Polycyclic cycloalkyls include adamantine and norbornane. The term cycloalkyl includes "unsaturated nonaromatic carbocyclyl" or "nonaromatic unsaturated carbocyclyl" groups, both of which refer to a nonaromatic carbocycle as defined herein, which contains at least one carbon carbon double bond or one carbon carbon triple bond.

As used herein, the term "substituted" means that an atom or group of atoms has replaced hydrogen as the substituent attached to another group. The term "substituted" further refers to any level of substitution, namely mono-, di-, tri-, tetra-, or penta-substitution, where such substitution is permitted. The substituents are independently selected, and substitution may be at any chemically accessible position. In one embodiment, the substituents vary in number between one and four. In another embodiment, the substituents vary in number between one and three. In yet another embodiment, the substituents vary in number between one and two.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The present invention relates generally to compositions and methods for treating and preventing cancer. The invention is useful, for example, for reducing tumor growth and tumor cell proliferation. In certain embodiments, the invention treats or prevents any disease or disorder associated with p53 gain of function (GOF) mutation.

In certain instances, mutation of p53 not only abolishes wild-type p53 tumor suppressive function, but also causes for tumor promoting functions. The present invention is partly based upon the unexpected discovery that various p53 GOF mutants regulate one or more epigenetic regulators, including for example various histone modifying enzymes. For example, the data presented herein demonstrates that specific p53 GOF mutations enhance the expression and activity of various epigenetic regulators, including histone methyltransferases MLL1 and MLL2, and the histone aceytltransferase, MOZ. Thus, p53 GOF mutants result in the activation of epigenetic pathways, which, in certain instances, play a role in tumor growth or tumor cell proliferation. Further, it is shown that the p53 GOF-induced activation of epigenetic pathways results in the activation of Ras pathways, which, while not wishing to be bound by any particular theory, may result in the growth of the tumor. For example, knockdown of MLL1 or MLL2 is shown herein to decrease the growth of mutant p53 cells. Further, it is shown herein that inhibition of the interaction between an MLL and menin and the inhibition of the interaction between an MLL and WDR5 reduces tumor growth.

While the present invention is exemplified herein by targeting of MLL1, MLL2, and/or MOZ, the present invention is not limited to the targeting of these particular epigenetic regulators. Rather, it is demonstrated herein that p53 GOF mutations regulate additional epigenetic regulators, including PPP1CC, RBBP5, OGT, BAP1, TAF3, SMARCD2, TTK, TCEA, STAT3, CTNNB1, and JMJD1B. Therefore, the present invention contemplates the targeting of these p53 GOF regulated epigenetic regulators as well.

The present invention is not limited to a particular type of cancer. Exemplary forms of cancer that are treatable or preventable with the compositions and methods of the present invention include, but are not limited to, carcinomas, sarcomas, lymphomas, leukemia, blastomas, and germ cell cancers. Other exemplary forms of cancer that are treatable or preventable with the compositions and methods of the present invention include, but are not limited to, breast cancer, lung cancer, pancreatic cancer, stomach cancer, bone cancer, ovarian cancer, prostate cancer, bladder cancer, cervical cancer, colon cancer, skin cancer, gliomas, esophageal cancer, oral cancer, gallbladder cancer, liver cancer, testicular cancer, uterine cancer, thyroid cancer, throat cancer, Li-Fraumeni Syndrome and the like.

In one embodiment, the present invention provides a composition for treating cancer in a subject, wherein the composition comprises an inhibitor of one or more epigenetic regulators. In one embodiment, the present invention provides a composition for treating cancer in a subject, wherein the composition comprises an inhibitor of MLL1. In one embodiment, the present invention provides a composition for treating cancer in a subject, wherein the composition comprises an inhibitor of MLL2. In one embodiment, the present invention provides a composition for treating cancer in a subject, wherein the composition comprises an inhibitor of MOZ. In one embodiment, the present invention provides a composition for treating cancer in a subject, wherein the composition comprises an inhibitor of MLL1, MLL2, MOZ, or a combination thereof.

In certain instances, the MLL enzymes are components of several multi-subunit protein complexes. In one embodiment, the composition of the invention comprises an inhibitor of at least one member of a complex comprising MLL1, MLL2, or MOZ. In one embodiment, the composition comprises an inhibitor of MLL1, MLL2, MOZ, menin, WDR5, or a combination thereof.

In one embodiment, the composition comprises an inhibitor of an interaction in a complex comprising MLL1, MLL2, MOZ. For example, in one embodiment, the composition comprises an inhibitor of the interaction between an MLL and menin. For example, in one embodiment, the inhibitor which inhibits the interaction between an MLL and menin is ISC-30 [N,N'-bis(4-aminophenyl)-N,N'-dimethylethylenediamine]. in one embodiment, the inhibitor which inhibits the interaction between an MLL and menin is MI-2-2. In one embodiment, the composition comprises an inhibitor of the interaction between an MLL and WDR5. For example, in one embodiment, the inhibitor which inhibits the interaction between an MLL and WDR5 is OICR-9429.

In one embodiment, the composition comprises an inhibitor of the expression of at least one of MLL1, MLL2, MOZ, menin, and WDR5. For example, in one embodiment, the composition comprises an isolated nucleic acid (e.g., siRNA, ribozyme, antisense RNA, etc.) that reduces the nucleic acid or protein expression level in a cell of at least one of MLL1, MLL2, MOZ, menin, and WDR5.

In one embodiment, the composition comprises an inhibitor of the activity of at least one of MLL1, MLL2, MOZ, menin, and WDR5. For example, in one embodiment, the composition comprises a nucleic acid, peptide, antibody, small molecule, antagonist, aptamer, or peptidomimetic that reduces the activity of at least one of MLL1, MLL2, MOZ, menin, and WDR5.

In certain embodiments, the composition comprises a combination of inhibitors described herein. For example, in one embodiment the composition comprises a combination comprising at least two of a MLL1 inhibitor, MLL2 inhibitor, a MOZ inhibitor, a menin inhibitor, and a WDR5 inhibitor. In one embodiment, the present invention provides a composition, wherein the composition comprises a combination comprising at least three of a MLL1 inhibitor, MLL2 inhibitor, a MOZ inhibitor, a menin inhibitor, and a WDR5 inhibitor. In one embodiment, the present invention provides a composition, wherein the composition comprises a combination comprising at least four of a MLL1 inhibitor, MLL2 inhibitor, a MOZ inhibitor, a menin inhibitor, and a WDR5 inhibitor. In one embodiment, the present invention provides a composition, wherein the composition comprises a combination comprising a MLL1 inhibitor, MLL2 inhibitor, a MOZ inhibitor, a menin inhibitor, and a WDR5 inhibitor.

In one embodiment, the present invention provides a method for treating or preventing cancer. In one embodiment, the method comprises administering to a subject an effective amount of a composition comprising an inhibitor of MLL1, an inhibitor of MLL2, an inhibitor of MOZ, an inhibitor of menin, an inhibitor of WDR5, or a combination thereof. In certain embodiments, the method comprises administering to a subject one or more of an effective amount of a composition comprising an inhibitor of MLL1, an effective amount of a composition comprising an inhibitor of MLL2, an effective amount of a composition comprising an inhibitor of MOZ, an effective amount of a composition comprising an inhibitor of menin, and an effective amount of a composition comprising an inhibitor of WDR5.

In one embodiment, the present invention provides a tailored or personalized treatment of cancer. As described herein, in certain embodiments, the particular inhibitor, or combination of inhibitors, administered to the subject is dependent upon the particular epigenetic signature of the tumor cell of the subject. For example, in certain embodiments, the method comprises classifying the cancer of the subject based upon the type of p53 GOF mutation present in a tumor or tumor cell of the subject. In one embodiment, the type of inhibitor, or combination of inhibitors, administered to the subject is dependent upon the type of p53 GOF mutation identified in the tumor or tumor cell.

Inhibitors

In one embodiment, the present invention provides a composition for treating or preventing cancer in a subject, wherein the composition inhibits tumor cell proliferation or reduces tumor growth. In certain embodiments, the composition inhibits the expression, activity, or both of MLL1, MLL2, MOZ, menin, WDR5, or a combination thereof in a tumor cell of the subject.

In one embodiment, the composition of the invention comprises an inhibitor of MLL1, MLL2, MOZ, menin, WDR5, or a combination thereof. An inhibitor of MLL1, MLL2, MOZ, menin, or WDR5 is any compound, molecule, or agent that reduces, inhibits, or prevents the function of MLL1, MLL2, MOZ, menin, or WDR5. For example, an inhibitor of MLL1, MLL2, MOZ, menin, or WDR5 is any compound, molecule, or agent that reduces the expression, activity, or both of MLL1, MLL2, MOZ, menin, or WDR5. In certain embodiments, the inhibitor inhibits the transcription of DNA, inhibits the translation of RNA, or inhibits the protein itself. In one embodiment, an inhibitor of MLL1, MLL2, MOZ, menin, or WDR5 comprises a nucleic acid, a peptide, an antibody, a small molecule, a siRNA, a ribozyme, an antisense nucleic acid, an antagonist, an aptamer, a peptidomimetic, or any combination thereof.

Small Molecule Inhibitors

In various embodiments, the inhibitor is a small molecule. When the inhibitor is a small molecule, a small molecule may be obtained using standard methods known to the skilled artisan. Such methods include chemical organic synthesis or biological means. Biological means include purification from a biological source, recombinant synthesis and in vitro translation systems, using methods well known in the art. In one embodiment, a small molecule inhibitor of the invention comprises an organic molecule, inorganic molecule, biomolecule, synthetic molecule, and the like.

Combinatorial libraries of molecularly diverse chemical compounds potentially useful in treating a variety of diseases and conditions are well known in the art as are method of making the libraries. The method may use a variety of techniques well-known to the skilled artisan including solid phase synthesis, solution methods, parallel synthesis of single compounds, synthesis of chemical mixtures, rigid core structures, flexible linear sequences, deconvolution strategies, tagging techniques, and generating unbiased molecular landscapes for lead discovery vs. biased structures for lead development.

In a general method for small library synthesis, an activated core molecule is condensed with a number of building blocks, resulting in a combinatorial library of covalently linked, core-building block ensembles. The shape and rigidity of the core determines the orientation of the building blocks in shape space. The libraries can be biased by changing the core, linkage, or building blocks to target a characterized biological structure ("focused libraries") or synthesized with less structural bias using flexible cores.

Small molecule inhibitors of MLL1, include for example, the small molecule peptidomimetic inhibitors MM-401 and MM-101, described in Karatas et al., 2013, J. Am. Chem. Soc., 135, 669-682 and Cao et al., 2014, Molecular Cell, 53(2): 247-251, the contents of which are incorporated by reference herein in their entirety. A small molecule inhibitor of menin, includes for example, MI-2-2, which inhibits the interaction between menin and an MLL, as described in Grembecka et al., 2012, Nat Chem Biol, 8: 277-284; Shi et al., 2012, Blood, 120: 4461-4469, the contents of which are incorporated by reference herein in their entirety. A small molecule inhibitor of WDR5, includes, for example, OICR-9429, an antagonist of the interaction between WDR5 with an MLL, as described in Grebien et al., 2015, Nature Chemical Biology, in revision, the contents of which are incorporated by reference herein in their entirety. Other exemplary inhibitors of WDR5 are described in Senisterra et al (Senisterra et al., 2013, The Biochemical journal, 449: 151-159), the contents of which are incorporated by reference herein in their entirety.

In one embodiment, the small molecule inhibitor inhibits the interaction of an MLL enzyme and menin. For example, in one embodiment, the small molecule inhibitor which inhibits the interaction of an MLL and menin is ISC-30. As used herein, the term "ISC-30" refers to N,N'-bis(4-aminophenyl)-N,N'-dimethylethylenediamine.

In one embodiment, the compound of the invention is a compound of formula (I), or a salt, solvate, or N-oxide thereof:

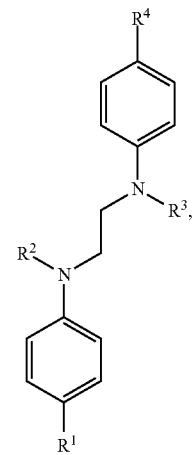

(I)

wherein in formula (I):

$R^1$ and $R^4$ are each independently selected from the group consisting of hydrogen, halogen, $NR^aR^b$, hydroxyl, linear or branched $C_1$-$C_6$ alkyl, linear or branched $C_2$-$C_6$ alkenyl, linear or branched $C_2$-$C_6$ alkynyl, $C_3$-$C_8$ cycloalkyl, $C_3$-$C_8$ cycloalkenyl, and $C_1$-$C_6$ alkoxy, wherein said alkyls, alkenyls, alkynyls, cycloalkyls, cycloalkenyls and alkoxys of $R^1$ and $R^4$ are unsubstituted or substituted with at least one halogen;

$R^a$ and $R^b$ are each independently selected from the group consisting of hydrogen, linear or branched $C_1$-$C_4$ alkyl, linear or branched $C_2$-$C_4$ alkenyl, $C_2$-$C_4$ alkynyl, $C_3$-$C_6$ cycloalkyl, and $C_3$-$C_6$ cycloalkenyl, wherein said alkyls, alkenyls, alkynyls, cycloalkyls, cycloalkenyls of $R^a$ and $R^b$ are unsubstituted or substituted with at least one halogen; and $R^2$ and $R^3$ are each independently selected from group consisting of hydrogen, linear or branched $C_1$-$C_6$ alkyl, linear or branched $C_2$-$C_6$ alkenyl, linear or branched $C_2$-$C_6$ alkynyl, $C_3$-$C_8$ cycloalkyl, and $C_3$-$C_8$ cycloalkenyl, wherein said alkyls, alkenyls, alkynyls, cycloalkyls, cycloalkenyls of $R^2$ and $R^3$ are unsubstituted or substituted with at least one halogen.

In one embodiment, at least one of $R^2$ and $R^3$ is an unsubstituted $C_1$-$C_6$ alkyl or a $C_1$-$C_6$ alkyl substituted with at least one halogen.

In one embodiment, both $R^2$ and $R^3$ are each independently selected from an unsubstituted $C_1$-$C_6$ alkyl or a $C_1$-$C_6$ alkyl substituted with at least one halogen.

In one embodiment, at least one of $R^2$ and $R^3$ is an unsubstituted methyl or ethyl or is a methyl or ethyl substituted with at least one halogen.

In one embodiment, both $R^2$ and $R^3$ are each independently selected from an unsubstituted methyl or ethyl or is a methyl or ethyl substituted with at least one halogen.

In one embodiment, at least one of $R^1$ and $R^4$ is $NR^aR^b$.

In one embodiment, both $R^1$ and $R^4$ are each independently $NR^aR^b$.

In one embodiment, at least one of $R^a$ and $R^b$ is a hydrogen.

In one embodiment, all $R^a$ and $R^b$ are hydrogen.

In one embodiment, at least one of $R^1$ and $R^4$ is a hydroxyl.

In one embodiment, at least one of $R^1$ and $R^4$ is a linear or branched $C_1$-$C_6$ alkyl, linear or branched $C_2$-$C_6$ alkenyl, linear or branched $C_2$-$C_6$ alkynyl, $C_3$-$C_8$ cycloalkyl or $C_3$-$C_8$ cycloalkenyl.

In one embodiment, at least one of $R^1$ and $R^4$ is a $C_1$-$C_6$ alkyl.

In one embodiment, at least one of $R^1$ and $R^4$ is a $C_1$-$C_6$ alkoxy.

In one embodiment, each halogen is selected independently from fluorine, chlorine, bromine, or iodine.

In one embodiment, all halogen substitutions are chlorines.

In one embodiment, the compound of formula (I) is N,N'-bis(4-aminophenyl)-N,N'-dimethylethylenediamine (ISC-30)

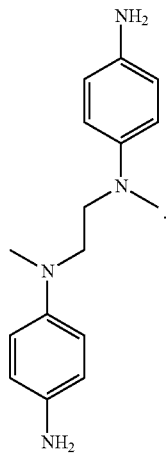 [SMILES: CN(CCN(C)c1ccc(N)cc1)c1ccc(N)cc1]

In one embodiment, the small molecule inhibitor inhibits the interaction between an MLL enzyme and WDR5. For example, in one embodiment, the small molecule inhibitor which inhibits the interaction between an MLL and WDR5 is OICR-9429, or a derivative or analogue thereof.

The small molecule and small molecule compounds described herein may be present as salts even if salts are not depicted and it is understood that the invention embraces all salts and solvates of the inhibitors depicted here, as well as the non-salt and non-solvate form of the inhibitors, as is well understood by the skilled artisan. In some embodiments, the salts of the inhibitors of the invention are pharmaceutically acceptable salts.

Where tautomeric forms may be present for any of the inhibitors described herein, each and every tautomeric form is intended to be included in the present invention, even though only one or some of the tautomeric forms may be explicitly depicted. For example, when a 2-hydroxypyridyl moiety is depicted, the corresponding 2-pyridone tautomer is also intended.

The invention also includes any or all of the stereochemical forms, including any enantiomeric or diasteriomeric forms of the inhibitors described. The recitation of the structure or name herein is intended to embrace all possible stereoisomers of inhibitors depicted. All forms of the inhibitors are also embraced by the invention, such as crystalline or non-crystalline forms of the inhibitors. Compositions comprising an inhibitor of the invention are also intended, such as a composition of substantially pure inhibitor, including a specific stereochemical form thereof, or a composition comprising mixtures of inhibitors of the invention in any ratio, including two or more stereochemical forms, such as in a racemic or non-racemic mixture.

In one embodiment, the small molecule inhibitor of the invention comprises an analog or derivative of an inhibitor described herein.

In one embodiment, the small molecules described herein are candidates for derivatization. As such, in certain instances, the analogs of the small molecules described herein that have modulated potency, selectivity, and solubility are included herein and provide useful leads for drug discovery and drug development. Thus, in certain instances, during optimization new analogs are designed considering issues of drug delivery, metabolism, novelty, and safety.

In some instances, small molecule inhibitors described herein are derivatized/analoged as is well known in the art of combinatorial and medicinal chemistry. The analogs or derivatives can be prepared by adding and/or substituting functional groups at various locations. As such, the small molecules described herein can be converted into derivatives/analogs using well known chemical synthesis procedures. For example, all of the hydrogen atoms or substituents can be selectively modified to generate new analogs. Also, the linking atoms or groups can be modified into longer or shorter linkers with carbon backbones or hetero atoms. Also, the ring groups can be changed so as to have a different number of atoms in the ring and/or to include hetero atoms. Moreover, aromatics can be converted to cyclic rings, and vice versa. For example, the rings may be from 5-7 atoms, and may be homocycles or heterocycles.

As used herein, the term "analog," "analogue," or "derivative" is meant to refer to a chemical compound or molecule made from a parent compound or molecule by one or more chemical reactions. As such, an analog can be a structure having a structure similar to that of the small molecule inhibitors described herein or can be based on a scaffold of a small molecule inhibitor described herein, but differing from it in respect to certain components or structural makeup, which may have a similar or opposite action metabolically. An analog or derivative of any of a small molecule inhibitor in accordance with the present invention can be used to reduce skin pigmentation.

In one embodiment, the small molecule inhibitors described herein can independently be derivatized/analoged by modifying hydrogen groups independently from each other into other substituents. That is, each atom on each molecule can be independently modified with respect to the other atoms on the same molecule. Any traditional modification for producing a derivative/analog can be used. For example, the atoms and substituents can be independently comprised of hydrogen, an alkyl, aliphatic, straight chain aliphatic, aliphatic having a chain hetero atom, branched aliphatic, substituted aliphatic, cyclic aliphatic, heterocyclic aliphatic having one or more hetero atoms, aromatic, heteroaromatic, polyaromatic, polyamino acids, peptides, polypeptides, combinations thereof, halogens, halo-substituted aliphatics, and the like. Additionally, any ring group on a compound can be derivatized to increase and/or decrease ring size as well as change the backbone atoms to carbon atoms or hetero atoms.

Nucleic Acid Inhibitors

In other related aspects, the invention includes an isolated nucleic acid. In some instances the inhibitor is an siRNA or antisense molecule, which inhibits MLL1, MLL2, MOZ, menin, or WDR5. In one embodiment, the nucleic acid comprises a promoter/regulatory sequence such that the nucleic acid is preferably capable of directing expression of the nucleic acid. Thus, the invention encompasses expression vectors and methods for the introduction of exogenous DNA into cells with concomitant expression of the exogenous DNA in the cells such as those described, for example, in Sambrook et al. (2012, Molecular Cloning: A Laboratory Manual, Cold Spring Harbor Laboratory, New York), and in Ausubel et al. (1997, Current Protocols in Molecular Biology, John Wiley & Sons, New York) and as described elsewhere herein.

In another aspect of the invention, MLL1, MLL2, MOZ, menin, or WDR5, can be inhibited by way of inactivating and/or sequestering MLL1, MLL2, MOZ, menin, or WDR5. As such, inhibiting the activity of MLL1, MLL2, MOZ, menin, or WDR5 can be accomplished by using a transdominant negative mutant.

In one embodiment, siRNA is used to decrease the level of MLL1, MLL2, MOZ, menin, or WDR5 protein. RNA interference (RNAi) is a phenomenon in which the introduction of double-stranded RNA (dsRNA) into a diverse range of organisms and cell types causes degradation of the complementary mRNA. In the cell, long dsRNAs are cleaved into short 21-25 nucleotide small interfering RNAs, or siRNAs, by a ribonuclease known as Dicer. The siRNAs subsequently assemble with protein components into an RNA-induced silencing complex (RISC), unwinding in the process. Activated RISC then binds to complementary transcript by base pairing interactions between the siRNA antisense strand and the mRNA. The bound mRNA is cleaved and sequence specific degradation of mRNA results in gene silencing. See, for example, U.S. Pat. No. 6,506,559; Fire et al., 1998, Nature 391(19):306-311; Timmons et al., 1998, Nature 395:854; Montgomery et al., 1998, TIG 14 (7):255-258; David R. Engelke, Ed., RNA Interference (RNAi) Nuts & Bolts of RNAi Technology, DNA Press, Eagleville, P A (2003); and Gregory J. Hannon, Ed., RNAi A Guide to Gene Silencing, Cold Spring Harbor Laboratory Press, Cold Spring Harbor, N.Y. (2003). Soutschek et al. (2004, Nature 432:173-178) describe a chemical modification to siRNAs that aids in intravenous systemic delivery. Optimizing siRNAs involves consideration of overall G/C content, C/T content at the termini, Tm and the nucleotide content of the 3' overhang. See, for instance, Schwartz et al., 2003, Cell, 115:199-208 and Khvorova et al., 2003, Cell 115:209-216. Therefore, the present invention also includes methods of decreasing levels of MLL1, MLL2, or MOZ using RNAi technology.

In another aspect, the invention includes a vector comprising an siRNA or antisense polynucleotide. Preferably, the siRNA or antisense polynucleotide is capable of inhibiting the expression of a target polypeptide, wherein the target polypeptide is selected from the group consisting of MLL1, MLL2, MOZ, menin, and WDR5. The incorporation of a desired polynucleotide into a vector and the choice of vectors is well-known in the art as described in, for example, Sambrook et al. (2012), and in Ausubel et al. (1997), and elsewhere herein.

In certain embodiments, the expression vectors described herein encode a short hairpin RNA (shRNA) inhibitor. shRNA inhibitors are well known in the art and are directed against the mRNA of a target, thereby decreasing the expression of the target. In certain embodiments, the encoded shRNA is expressed by a cell, and is then processed into siRNA. For example, in certain instances, the cell possesses native enzymes (e.g., dicer) that cleaves the shRNA to form siRNA.

The siRNA, shRNA, or antisense polynucleotide can be cloned into a number of types of vectors as described elsewhere herein. For expression of the siRNA or antisense polynucleotide, at least one module in each promoter functions to position the start site for RNA synthesis.

In order to assess the expression of the siRNA, shRNA, or antisense polynucleotide, the expression vector to be introduced into a cell can also contain either a selectable marker gene or a reporter gene or both to facilitate identification and selection of expressing cells from the population of cells sought to be transfected or infected using a viral vector. In other embodiments, the selectable marker may be carried on a separate piece of DNA and used in a co-transfection procedure. Both selectable markers and reporter genes may be flanked with appropriate regulatory sequences to enable expression in the host cells. Useful selectable markers are known in the art and include, for example, antibiotic-resistance genes, such as neomycin resistance and the like.

Therefore, in another aspect, the invention relates to a vector, comprising the nucleotide sequence of the invention or the construct of the invention. The choice of the vector will depend on the host cell in which it is to be subsequently introduced. In a particular embodiment, the vector of the invention is an expression vector. Suitable host cells include a wide variety of prokaryotic and eukaryotic host cells. In specific embodiments, the expression vector is selected from the group consisting of a viral vector, a bacterial vector and a mammalian cell vector. Prokaryote- and/or eukaryote-vector based systems can be employed for use with the present invention to produce polynucleotides, or their cognate polypeptides. Many such systems are commercially and widely available.

Further, the expression vector may be provided to a cell in the form of a viral vector. Viral vector technology is well known in the art and is described, for example, in Sambrook et al. (2012), and in Ausubel et al. (1997), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers. (See, e.g., WO 01/96584; WO 01/29058; and U.S. Pat. No. 6,326,193.

By way of illustration, the vector in which the nucleic acid sequence is introduced can be a plasmid which is or is not integrated in the genome of a host cell when it is introduced in the cell. Illustrative, non-limiting examples of vectors in which the nucleotide sequence of the invention or the gene construct of the invention can be inserted include a tet-on inducible vector for expression in eukaryote cells.

The vector may be obtained by conventional methods known by persons skilled in the art (Sambrook et al., 2012). In a particular embodiment, the vector is a vector useful for transforming animal cells.

In one embodiment, the recombinant expression vectors may also contain nucleic acid molecules which encode a peptide or peptidomimetic inhibitor of invention, described elsewhere herein.

A promoter may be one naturally associated with a gene or polynucleotide sequence, as may be obtained by isolating the 5' non-coding sequences located upstream of the coding segment and/or exon. Such a promoter can be referred to as "endogenous." Similarly, an enhancer may be one naturally associated with a polynucleotide sequence, located either downstream or upstream of that sequence. Alternatively, certain advantages will be gained by positioning the coding polynucleotide segment under the control of a recombinant or heterologous promoter, which refers to a promoter that is not normally associated with a polynucleotide sequence in its natural environment. A recombinant or heterologous enhancer refers also to an enhancer not normally associated with a polynucleotide sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (U.S. Pat. Nos. 4,683,202, 5,928,906). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the cell type, organelle, and organism chosen for expression. Those of skill in the art of molecular biology generally know how to use promoters, enhancers, and cell type combinations for protein expression, for example, see Sambrook et al. (2012). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

The recombinant expression vectors may also contain a selectable marker gene which facilitates the selection of transformed or transfected host cells. Suitable selectable marker genes are genes encoding proteins such as G418 and hygromycin which confer resistance to certain drugs, β-galactosidase, chloramphenicol acetyltransferase, firefly luciferase, or an immunoglobulin or portion thereof such as the Fc portion of an immunoglobulin preferably IgG. The selectable markers may be introduced on a separate vector from the nucleic acid of interest.

Following the generation of the siRNA polynucleotide, a skilled artisan will understand that the siRNA polynucleotide will have certain characteristics that can be modified to improve the siRNA as a therapeutic compound. Therefore, the siRNA polynucleotide may be further designed to resist degradation by modifying it to include phosphorothioate, or other linkages, methylphosphonate, sulfone, sulfate, ketyl, phosphorodithioate, phosphoramidate, phosphate esters, and the like (see, e.g., Agrwal et al., 1987, Tetrahedron Lett. 28:3539-3542; Stec et al., 1985 Tetrahedron Lett. 26:2191-2194; Moody et al., 1989 Nucleic Acids Res. 12:4769-4782; Eckstein, 1989 Trends Biol. Sci. 14:97-100; Stein, In: Oligodeoxynucleotides. Antisense Inhibitors of Gene Expression, Cohen, ed., Macmillan Press, London, pp. 97-117 (1989)).

Any polynucleotide may be further modified to increase its stability in vivo. Possible modifications include, but are not limited to, the addition of flanking sequences at the 5' and/or 3' ends; the use of phosphorothioate or 2' O-methyl rather than phosphodiester linkages in the backbone; and/or the inclusion of nontraditional bases such as inosine, queosine, and wybutosine and the like, as well as acetyl-methyl-, thio- and other modified forms of adenine, cytidine, guanine, thymine, and uridine.

In one embodiment of the invention, an antisense nucleic acid sequence which is expressed by a plasmid vector is used to inhibit MLL1, MLL2, MOZ, menin, or WDR5 protein expression. The antisense expressing vector is used to transfect a mammalian cell or the mammal itself, thereby causing reduced endogenous expression of MLL1, MLL2, MOZ, menin, or WDR5.

Antisense molecules and their use for inhibiting gene expression are well known in the art (see, e.g., Cohen, 1989, In: Oligodeoxyribonucleotides, Antisense Inhibitors of Gene Expression, CRC Press). Antisense nucleic acids are DNA or RNA molecules that are complementary, as that term is defined elsewhere herein, to at least a portion of a specific mRNA molecule (Weintraub, 1990, Scientific American 262:40). In the cell, antisense nucleic acids hybridize to the corresponding mRNA, forming a double-stranded molecule thereby inhibiting the translation of genes.

The use of antisense methods to inhibit the translation of genes is known in the art, and is described, for example, in Marcus-Sakura (1988, Anal. Biochem. 172:289). Such antisense molecules may be provided to the cell via genetic expression using DNA encoding the antisense molecule as taught by Inoue, 1993, U.S. Pat. No. 5,190,931.

Alternatively, antisense molecules of the invention may be made synthetically and then provided to the cell. Antisense oligomers of between about 10 to about 30, and more preferably about 15 nucleotides, are preferred, since they are easily synthesized and introduced into a target cell. Synthetic antisense molecules contemplated by the invention include oligonucleotide derivatives known in the art which have improved biological activity compared to unmodified oligonucleotides (see U.S. Pat. No. 5,023,243).

In one embodiment of the invention, a ribozyme is used to inhibit MLL1, MLL2, MOZ, menin, or WDR5 protein expression. Ribozymes useful for inhibiting the expression of a target molecule may be designed by incorporating target sequences into the basic ribozyme structure which are complementary, for example, to the mRNA sequence encoding MLL1, MLL2, MOZ, menin, or WDR5. Ribozymes targeting MLL1, MLL2, MOZ, menin, or WDR5, may be synthesized using commercially available reagents (Applied Biosystems, Inc., Foster City, Calif.) or they may be genetically expressed from DNA encoding them.

In one embodiment, the nucleic acid inhibitor of the invention is an antagonist of MLL1, MLL2, MOZ, menin, or WDR5. For example, in certain embodiments, the isolated nucleic acid specifically binds to MLL1, MLL2, MOZ, menin, WDR5, or a target of MLL1, MLL2, MOZ, menin, or WDR5, to inhibit the functional activity of MLL1, MLL2, MOZ, menin, or WDR5.

Aptamers

In one embodiment, the composition comprises an aptamer, including for example a protein aptamer or a polynucleotidal aptamer. In one embodiment, the aptamer inhibits the expression, activity, or both of MLL1, MLL2, MOZ, menin, or WDR5.

In one embodiment, an apatmer is a nucleic acid or oligonucleotide molecule that binds to a specific molecular target, such as MLL1, MLL2, MOZ, menin, or WDR5. In one embodiment, aptamers are obtained from an in vitro evolutionary process known as SELEX (Systematic Evolution of Ligands by EXponential Enrichment), which selects target-specific aptamer sequences from combinatorial libraries of single stranded oligonucleotide templates comprising randomized sequences. In some embodiments, aptamer compositions are double-stranded or single-stranded, and in various embodiments include deoxyribonucleotides, ribonucleotides, nucleotide derivatives, or other nucleotide-like molecules. In some embodiments, the nucleotide components of an aptamer include modified or non-natural nucleotides, for example nucleotides that have modified sugar groups (e.g., the 2'-OH group of a ribonucleotide is replaced by 2'-F or 2'-NH$_2$), which in some instances, improves a desired property, e.g., resistance to nucleases or longer lifetime in blood.

In some instances, individual aptamers having the same nucleotide sequence differ in their secondary structure. In some embodiments, the aptamers of the invention are conjugated to other molecules, e.g., a high molecular weight carrier to slow clearance of the aptamer from the circulatory system. In some instances, aptamers are specifically cross-linked to their cognate ligands, e.g., by photo-activation of a cross-linker. (Brody, E. N. and L. Gold (2000) J. Biotechnol. 74:5-13).

A method for the in vitro evolution of nucleic acid molecules with high affinity binding to target molecules is known to those of skill in the art and is described in U.S. Pat. No. 5,270,163. The method, known as SELEX (Selective Evolution of Ligands by EXponential Enrichment) involves selection from a mixture of candidate oligonucleotides from a library comprising a large sequence variations (e.g. about $10^{15}$) and step-wise iterations of binding, partitioning and amplification, using the same general selection theme, to achieve virtually any desired criterion of binding affinity and selectivity.

Starting from a mixture of nucleic acids, preferably comprising a segment of randomized sequence, the SELEX method includes the steps of contacting the mixture with the desired target, partitioning unbound nucleic acids from those nucleic acids which have bound to the target molecule, dissociating the nucleic acid-target complexes, amplifying the nucleic acids dissociated from the nucleic acid-target complexes to yield a ligand-enriched mixture of nucleic acids, then reiterating the steps of binding, partitioning, dissociating and amplifying through as many cycles as desired to yield high affinity nucleic acid ligands to the target molecule.

Peptide Inhibitors

In other related aspects, the invention includes an isolated peptide inhibitor that inhibits MLL1, MLL2, MOZ, menin, or WDR5. For example, in one embodiment, the peptide inhibitor of the invention inhibits MLL1, MLL2, MOZ, menin, or WDR5 directly by binding to MLL1, MLL2, MOZ, menin, or WDR5 thereby preventing the normal functional activity of MLL1, MLL2, MOZ, menin, or WDR5. In another embodiment, the peptide inhibitor of the invention inhibits MLL1, MLL2, MOZ, menin, or WDR5 by competing with endogenous MLL1, MLL2, MOZ, menin, or WDR5. In yet another embodiment, the peptide inhibitor of the invention inhibits the activity of MLL1, MLL2, MOZ, menin, or WDR5 by acting as a transdominant negative mutant.

Exemplary peptide inhibitors of MLL1 activity is disclosed, for example, in Karatas et al., 2010, Med. Chem., 53, 5179.

The variants of the polypeptides according to the present invention may be (i) one in which one or more of the amino acid residues are substituted with a conserved or non-conserved amino acid residue (preferably a conserved amino acid residue) and such substituted amino acid residue may or may not be one encoded by the genetic code, (ii) one in which there are one or more modified amino acid residues, e.g., residues that are modified by the attachment of substituent groups, (iii) one in which the polypeptide is an alternative splice variant of the polypeptide of the present invention, (iv) fragments of the polypeptides and/or (v) one in which the polypeptide is fused with another polypeptide, such as a leader or secretory sequence or a sequence which is employed for purification (for example, His-tag) or for detection (for example, Sv5 epitope tag). The fragments include polypeptides generated via proteolytic cleavage (including multi-site proteolysis) of an original sequence. Variants may be post-translationally, or chemically modified. Such variants are deemed to be within the scope of those skilled in the art from the teaching herein.

As known in the art the "similarity" between two polypeptides is determined by comparing the amino acid sequence and its conserved amino acid substitutes of one polypeptide to a sequence of a second polypeptide. Variants are defined to include polypeptide sequences different from the original sequence, preferably different from the original sequence in less than 40% of residues per segment of interest, more preferably different from the original sequence in less than 25% of residues per segment of interest, more preferably different by less than 10% of residues per segment of interest, most preferably different from the original protein sequence in just a few residues per segment of interest and at the same time sufficiently homologous to the original sequence to preserve the functionality of the original sequence and/or the ability to bind to ubiquitin or to a ubiquitylated protein. The present invention includes amino acid sequences that are at least 60%, 65%, 70%, 72%, 74%, 76%, 78%, 80%, 90%, or 95% similar or identical to the original amino acid sequence. The degree of identity between two polypeptides is determined using computer algorithms and methods that are widely known for the persons skilled in the art. The identity between two amino acid sequences is preferably determined by using the BLASTP algorithm [BLAST Manual, Altschul, S., et al., NCBI NLM NIH Bethesda, Md. 20894, Altschul, S., et al., J. Mol. Biol. 215: 403-410 (1990)].

The polypeptides of the invention can be post-translationally modified. For example, post-translational modifications that fall within the scope of the present invention include signal peptide cleavage, glycosylation, acetylation, isoprenylation, proteolysis, myristoylation, protein folding and proteolytic processing, etc. Some modifications or processing events require introduction of additional biological machinery. For example, processing events, such as signal peptide cleavage and core glycosylation, are examined by adding canine microsomal membranes or *Xenopus* egg extracts (U.S. Pat. No. 6,103,489) to a standard translation reaction.

The polypeptides of the invention may include unnatural amino acids formed by post-translational modification or by introducing unnatural amino acids during translation. A variety of approaches are available for introducing unnatural amino acids during protein translation. By way of example, special tRNAs, such as tRNAs which have suppressor properties, suppressor tRNAs, have been used in the process of site-directed non-native amino acid replacement (SNAAR). In SNAAR, a unique codon is required on the mRNA and the suppressor tRNA, acting to target a non-native amino acid to a unique site during the protein synthesis (described in WO90/05785). However, the suppressor tRNA must not be recognizable by the aminoacyl tRNA synthetases present in the protein translation system. In certain cases, a non-native amino acid can be formed after the tRNA molecule is aminoacylated using chemical reactions which specifically modify the native amino acid and do not significantly alter the functional activity of the amino-acylated tRNA. These reactions are referred to as post-aminoacylation modifications. For example, the epsilon-amino group of the lysine linked to its cognate tRNA ($tRNA_{LYS}$), could be modified with an amine specific photoaffinity label.

A peptide inhibitor of the invention may be conjugated with other molecules, such as proteins, to prepare fusion proteins. This may be accomplished, for example, by the synthesis of N-terminal or C-terminal fusion proteins provided that the resulting fusion protein retains the functionality of the peptide inhibitor. Cyclic derivatives of the peptides or chimeric proteins of the invention are also part of the present invention. Cyclization may allow the peptide or chimeric protein to assume a more favorable conformation for association with other molecules. Cyclization may be achieved using techniques known in the art. For example, disulfide bonds may be formed between two appropriately spaced components having free sulfhydryl groups, or an amide bond may be formed between an amino group of one component and a carboxyl group of another component. Cyclization may also be achieved using an azobenzene-containing amino acid as described by Ulysse, L., et al., J. Am. Chem. Soc. 1995, 117, 8466-8467. The components that form the bonds may be side chains of amino acids, non-amino acid components or a combination of the two. In an embodiment of the invention, cyclic peptides may comprise a beta-turn in the right position. Beta-turns may be introduced into the peptides of the invention by adding the amino acids Pro-Gly at the right position.

It may be desirable to produce a cyclic peptide which is more flexible than the cyclic peptides containing peptide bond linkages as described above. A more flexible peptide may be prepared by introducing cysteines at the right and left position of the peptide and forming a disulphide bridge between the two cysteines. The two cysteines are arranged so as not to deform the beta-sheet and turn. The peptide is more flexible as a result of the length of the disulfide linkage and the smaller number of hydrogen bonds in the beta-sheet portion. The relative flexibility of a cyclic peptide can be determined by molecular dynamics simulations.

(a) Tags

In a particular embodiment of the invention, the polypeptide of the invention further comprises the amino acid sequence of a tag. The tag includes but is not limited to: polyhistidine tags (His-tags) (for example H6 and H10, etc.) or other tags for use in IMAC systems, for example, $Ni^{2+}$ affinity columns, etc., GST fusions, MBP fusions, streptavidine-tags, the BSP biotinylation target sequence of the bacterial enzyme BIRA and tag epitopes that are directed by antibodies (for example c-myc tags, FLAG-tags, among others). As will be observed by a person skilled in the art, the tag peptide can be used for purification, inspection, selection and/or visualization of the fusion protein of the invention. In a particular embodiment of the invention, the tag is a detection tag and/or a purification tag. It will be appreciated that the tag sequence will not interfere in the function of the protein of the invention.

(b) Leader and Secretory Sequences

Accordingly, the polypeptides of the invention can be fused to another polypeptide or tag, such as a leader or secretory sequence or a sequence which is employed for purification or for detection. In a particular embodiment, the polypeptide of the invention comprises the glutathione-S-transferase protein tag which provides the basis for rapid high-affinity purification of the polypeptide of the invention. Indeed, this GST-fusion protein can then be purified from cells via its high affinity for glutathione. Agarose beads can be coupled to glutathione, and such glutathione-agarose beads bind GST-proteins. Thus, in a particular embodiment of the invention, the polypeptide of the invention is bound to a solid support. In a preferred embodiment, if the polypeptide of the invention comprises a GST moiety, the polypeptide is coupled to a glutathione-modified support. In a particular case, the glutathione modified support is a glutathione-agarose bead. Additionally, a sequence encoding a protease cleavage site can be included between the affinity tag and the polypeptide sequence, thus permitting the removal of the binding tag after incubation with this specific enzyme and thus facilitating the purification of the corresponding protein of interest.

(c) Targeting Sequences

The invention also relates to a chimeric peptide comprising a peptide inhibitor described herein, fused to a targeting domain capable of directing the chimeric peptide to a desired cellular component or cell type or tissue. The chimeric peptide may also contain additional amino acid sequences or domains. The chimeric peptide are recombinant in the sense that the various components are from different sources, and as such are not found together in nature (i.e., are heterologous).

The targeting domain can be a membrane spanning domain, a membrane binding domain, or a sequence directing the peptide to associate with for example vesicles or with the nucleus. The targeting domain can target a peptide inhibitor to a particular cell type or tissue. For example, the targeting domain can be a cell surface ligand or an antibody against cell surface antigens of a target tissue (e.g., skin or melanocyte). A targeting domain may target a peptide inhibitor to a cellular component.

(d) Intracellular Targeting

Combined with certain formulations, such peptides can be effective intracellular agents. However, in order to increase the efficacy of such peptides, the peptide inhibitor can be provided as a fusion or chimeric peptide comprising a second peptide which promotes "transcytosis", e.g., uptake of the peptide by cells. To illustrate, the peptide inhibitor of the present invention can be provided as part of a fusion polypeptide with all or a fragment of the N-terminal domain of the HIV protein Tat, e.g., residues 1-72 of Tat or a smaller fragment thereof which can promote transcytosis. In other embodiments, the peptide inhibitor can be provided a fusion polypeptide with all or a portion of the antenopedia III protein.

To further illustrate, the peptide inhibitor can be provided as a chimeric peptide which includes a heterologous peptide sequence ("internalizing peptide") which drives the translocation of an extracellular form of a peptide inhibitor across a cell membrane in order to facilitate intracellular localization of the peptide inhibitor. In this regard, the therapeutic peptide inhibitor is one which is active intracellularly. The internalizing peptide, by itself, is capable of crossing a cellular membrane by, e.g., transcytosis, at a relatively high rate. The internalizing peptide is conjugated, e.g., as a fusion protein, to the peptide inhibitor. The resulting chimeric peptide is transported into cells at a higher rate relative to the activator polypeptide alone to thereby provide a means for enhancing its introduction into cells to which it is applied.

In one embodiment, the composition comprises a peptidomimetic inhibitor of at least one of MLL1, MLL2, MOZ, menin, or WDR5. Peptidomimetics are compounds based on, or derived from, peptides and proteins. The peptidomimetics of the present invention typically can be obtained by structural modification of known MLL1, MLL2, MOZ, menin, or WDR5 sequences or sequences that interact with MLL1, MLL2, MOZ, menin, or WDR5, using unnatural amino acids, conformational restraints, isosteric replacement, and the like. The peptidomimetics constitute the continuum of structural space between peptides and non-peptide synthetic structures. Exemplary peptidomimetic inhibitors of MLL1 is disclosed, for example, in Karatas et al., 2013, J. Am. Chem. Soc., 135, 669-682 and Cao et al., 2014, Molecular Cell, 53(2): 247-251, the contents of which are incorporated by reference herein in their entirety.

Such peptidomimetics can have such attributes as being non-hydrolyzable (e.g., increased stability against proteases or other physiological conditions which degrade the corresponding peptide), increased specificity and/or potency, and increased cell permeability for intracellular localization of the peptidomimetic. For illustrative purposes, peptide analogs of the present invention can be generated using, for example, benzodiazepines (e.g., see Freidinger et al. in Peptides: Chemistry and Biology, G. R. Marshall ed., ESCOM Publisher: Leiden, Netherlands, 1988), substituted gamma lactam rings (Garvey et al. in Peptides: Chemistry and Biology, G. R. Marshall ed., ESCOM Publisher: Leiden, Netherlands, 1988, p123), C-7 mimics (Huffman et al. in Peptides: Chemistry and Biology, G. R. Marshall ed., ESCOM Publisher: Leiden, Netherlands, 1988, p. 105), keto-methylene pseudopeptides (Ewenson et al. (1986) J Med Chem 29:295; and Ewenson et al. in Peptides: Structure and Function (Proceedings of the 9th American Peptide Symposium) Pierce Chemical Co. Rockland, Ill., 1985), β-turn dipeptide cores (Nagai et al. (1985) Tetrahedron Lett 26:647; and Sato et al. (1986) J Chem Soc Perkin Trans 1:1231), β-aminoalcohols (Gordon et al. (1985) Biochem Biophys Res Commun 126:419; and Dann et al. (1986) Biochem Biophys Res Commun 134:71), diaminoketones (Natarajan et al. (1984) Biochem Biophys Res Commun 124:141), and methyleneamino-modifed (Roark et al. in Peptides: Chemistry and Biology, G. R. Marshall ed., ESCOM Publisher: Leiden, Netherlands, 1988, p134). Also, see generally, Session III: Analytic and synthetic methods, in Peptides: Chemistry and Biology, G. R. Marshall ed., ESCOM Publisher: Leiden, Netherlands, 1988)

In addition to a variety of side chain replacements which can be carried out to generate peptidomimetics, the present invention contemplates the use of conformationally restrained mimics of peptide secondary structure. Numerous surrogates have been developed for the amide bond of peptides. Frequently exploited surrogates for the amide bond include the following groups (i) trans-olefins, (ii) fluoroalkene, (iii) methyleneamino, (iv) phosphonamides, and (v) sulfonamides.

In one embodiment, the inhibitor of the invention comprises a mimetope. Examples of mimetopes include, but are not limited to, protein-based compounds, carbohydrate-based compounds, lipid-based compounds, nucleic acid-based compounds, natural organic compounds, synthetically derived organic compounds, anti-idiotypic antibodies and/or catalytic antibodies, or fragments thereof. A mimetope can be obtained by, for example, screening libraries of natural and synthetic compounds for compounds capable of binding to MLL1, MLL2, MOZ, menin, or WDR5. A mimetope can also be obtained, for example, from libraries of natural and synthetic compounds, in particular, chemical or combinatorial libraries (i.e., libraries of compounds that differ in sequence or size but that have the same building blocks). A mimetope can also be obtained by, for example, rational drug design. In a rational drug design procedure, the three-dimensional structure of a compound of the present invention can be analyzed by, for example, nuclear magnetic resonance (NMR) or x-ray crystallography. The three-dimensional structure can then be used to predict structures of potential mimetopes by, for example, computer modelling, the predicted mimetope structures can then be produced by, for example, chemical synthesis, recombinant DNA technology, or by isolating a mimetope from a natural source (e.g., plants, animals, bacteria and fungi).

A peptide or peptidomimetic inhibitor of the invention may be synthesized by conventional techniques. For example, the peptide or peptidomimetic inhibitor may be synthesized by chemical synthesis using solid phase peptide synthesis. These methods employ either solid or solution phase synthesis methods (see for example, J. M. Stewart, and J. D. Young, Solid Phase Peptide Synthesis, $2^{nd}$ Ed., Pierce Chemical Co., Rockford Ill. (1984) and G. Barany and R. B. Merrifield, The Peptides: Analysis Synthesis, Biology editors E. Gross and J. Meienhofer Vol. 2 Academic Press, New York, 1980, pp. 3-254 for solid phase synthesis techniques; and M Bodansky, Principles of Peptide Synthesis, Springer-Verlag, Berlin 1984, and E. Gross and J. Meienhofer, Eds., The Peptides: Analysis, Synthesis, Biology, suprs, Vol 1, for classical solution synthesis.)

N-terminal or C-terminal fusion proteins comprising a peptide or peptidomimetic inhibitor of the invention conjugated with other molecules may be prepared by fusing, through recombinant techniques, the N-terminal or C-terminal of the peptide or peptidomimetic inhibitor, and the sequence of a selected protein or selectable marker with a desired biological function. The resultant fusion proteins contain the peptide inhibitor, or chimeric protein fused to the selected protein or marker protein as described herein. Examples of proteins which may be used to prepare fusion proteins include immunoglobulins, glutathione-S-transferase (GST), hemagglutinin (HA), and truncated myc.

Peptides of the invention may be developed using a biological expression system. The use of these systems allows the production of large libraries of random peptide sequences and the screening of these libraries for peptide sequences that bind to particular proteins. Libraries may be produced by cloning synthetic DNA that encodes random peptide sequences into appropriate expression vectors. (see Christian et al 1992, J. Mol. Biol. 227:711; Devlin et al, 1990 Science 249:404; Cwirla et al 1990, Proc. Natl. Acad, Sci. USA, 87:6378). Libraries may also be constructed by concurrent synthesis of overlapping peptides (see U.S. Pat. No. 4,708,871).

The peptide or peptidomimetic inhibitor of the invention may be converted into pharmaceutical salts by reacting with inorganic acids such as hydrochloric acid, sulfuric acid, hydrobromic acid, phosphoric acid, etc., or organic acids such as formic acid, acetic acid, propionic acid, glycolic acid, lactic acid, pyruvic acid, oxalic acid, succinic acid, malic acid, tartaric acid, citric acid, benzoic acid, salicylic acid, benezenesulfonic acid, and toluenesulfonic acids.

Prior to its use as an inhibitor, a peptide is purified to remove contaminants. In this regard, it will be appreciated that the peptide will be purified so as to meet the standards set out by the appropriate regulatory agencies. Any one of a number of a conventional purification procedures may be used to attain the required level of purity including, for example, reversed-phase high-pressure liquid chromatography (HPLC) using an alkylated silica column such as $C_4$- or $C_{18}$-silica. A gradient mobile phase of increasing organic content is generally used to achieve purification, for example, acetonitrile in an aqueous buffer, usually containing a small amount of trifluoroacetic acid. Ion-exchange chromatography can be also used to separate polypeptides based on their charge. Affinity chromatography is also useful in purification procedures.

Antibodies and peptides may be modified using ordinary molecular biological techniques to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring synthetic amino acids. The polypeptides useful in the invention may further be conjugated to non-amino acid moieties that are useful in their application. In particular, moieties that improve the stability, biological half-life, water solubility, and immunologic characteristics of the peptide are useful. A non-limiting example of such a moiety is polyethylene glycol (PEG).

Antibody Inhibitors

The invention also contemplates an inhibitor of MLL1, MLL2, MOZ, menin, or WDR5 comprising an antibody, or antibody fragment, specific for MLL1, MLL2, MOZ, menin, or WDR5. That is, the antibody can inhibit MLL1, MLL2, MOZ, menin, or WDR5 to provide a beneficial effect.

The antibodies may be intact monoclonal or polyclonal antibodies, and immunologically active fragments (e.g., a Fab or (Fab)$_2$ fragment), an antibody heavy chain, an antibody light chain, humanized antibodies, a genetically engineered single chain $F_\nu$ molecule (Ladner et al, U.S. Pat. No. 4,946,778), or a chimeric antibody, for example, an antibody which contains the binding specificity of a murine antibody, but in which the remaining portions are of human origin. Antibodies including monoclonal and polyclonal antibodies, fragments and chimeras, may be prepared using methods known to those skilled in the art.

Antibodies can be prepared using intact polypeptides or fragments containing an immunizing antigen of interest. The polypeptide or oligopeptide used to immunize an animal may be obtained from the translation of RNA or synthesized chemically and can be conjugated to a carrier protein, if desired. Suitable carriers that may be chemically coupled to peptides include bovine serum albumin and thyroglobulin, keyhole limpet hemocyanin. The coupled polypeptide may then be used to immunize the animal (e.g., a mouse, a rat, or a rabbit).

Polyclonal antibodies useful in the present invention are generated by immunizing rabbits according to standard immunological techniques well-known in the art (see, e.g., Harlow et al., 1988, In: Antibodies, A Laboratory Manual, Cold Spring Harbor, N.Y.). Such techniques include immunizing an animal with a chimeric protein comprising a portion of another protein such as a maltose binding protein or glutathione (GSH) tag polypeptide portion, and/or a moiety such that the antigenic protein of interest is rendered immunogenic (e.g., an antigen of interest conjugated with keyhole limpet hemocyanin, KLH) and a portion comprising the respective antigenic protein amino acid residues. The chimeric proteins are produced by cloning the appropriate nucleic acids encoding the marker protein into a plasmid vector suitable for this purpose, such as but not limited to, pMAL-2 or pCMX.

However, the invention should not be construed as being limited solely to methods and compositions including these antibodies or to these portions of the antigens. Rather, the invention should be construed to include other antibodies, as that term is defined elsewhere herein, to antigens, or portions thereof. Further, the present invention should be construed to encompass antibodies, inter alia, bind to the specific antigens of interest, and they are able to bind the antigen present on Western blots, in solution in enzyme linked immunoassays, in fluorescence activated cells sorting (FACS) assays, in magenetic-actived cell sorting (MACS) assays, and in immunofluorescence microscopy of a cell transiently transfected with a nucleic acid encoding at least a portion of the antigenic protein, for example.

One skilled in the art would appreciate, based upon the disclosure provided herein, that the antibody can specifically bind with any portion of the antigen and the full-length protein can be used to generate antibodies specific therefor. However, the present invention is not limited to using the full-length protein as an immunogen. Rather, the present invention includes using an immunogenic portion of the protein to produce an antibody that specifically binds with a specific antigen. That is, the invention includes immunizing an animal using an immunogenic portion, or antigenic determinant, of the antigen.

Once armed with the sequence of a specific antigen of interest and the detailed analysis localizing the various conserved and non-conserved domains of the protein, the skilled artisan would understand, based upon the disclosure provided herein, how to obtain antibodies specific for the various portions of the antigen using methods well-known in the art or to be developed.

The skilled artisan would appreciate, based upon the disclosure provided herein, that that present invention includes use of a single antibody recognizing a single antigenic epitope but that the invention is not limited to use of a single antibody. Instead, the invention encompasses use of at least one antibody where the antibodies can be directed to the same or different antigenic protein epitopes.

The generation of polyclonal antibodies is accomplished by inoculating the desired animal with the antigen and isolating antibodies which specifically bind the antigen therefrom using standard antibody production methods such as those described in, for example, Harlow et al. (1988, In: Antibodies, A Laboratory Manual, Cold Spring Harbor, N.Y.).

Monoclonal antibodies directed against full length or peptide fragments of a protein or peptide may be prepared using any well known monoclonal antibody preparation procedures, such as those described, for example, in Harlow et al. (1988, In: Antibodies, A Laboratory Manual, Cold Spring Harbor, N.Y.) and in Tuszynski et al. (1988, Blood, 72:109-115). Quantities of the desired peptide may also be synthesized using chemical synthesis technology. Alternatively, DNA encoding the desired peptide may be cloned and expressed from an appropriate promoter sequence in cells suitable for the generation of large quantities of peptide. Monoclonal antibodies directed against the peptide are generated from mice immunized with the peptide using standard procedures as referenced herein.

Nucleic acid encoding the monoclonal antibody obtained using the procedures described herein may be cloned and sequenced using technology which is available in the art, and is described, for example, in Wright et al. (1992, Critical Rev. Immunol. 12:125-168), and the references cited therein. Further, the antibody of the invention may be "humanized" using the technology described in, for example, Wright et al., and in the references cited therein, and in Gu et al. (1997, Thrombosis and Hematocyst 77:755-759), and other methods of humanizing antibodies well-known in the art or to be developed.

The present invention also includes the use of humanized antibodies specifically reactive with epitopes of an antigen of interest. The humanized antibodies of the invention have a human framework and have one or more complementarity determining regions (CDRs) from an antibody, typically a mouse antibody, specifically reactive with an antigen of interest. When the antibody used in the invention is humanized, the antibody may be generated as described in Queen, et al. (U.S. Pat. No. 6,180,370), Wright et al., (supra) and in the references cited therein, or in Gu et al. (1997, Thrombosis and Hematocyst 77(4):755-759). The method disclosed in Queen et al. is directed in part toward designing humanized immunoglobulins that are produced by expressing recombinant DNA segments encoding the heavy and light chain complementarity determining regions (CDRs) from a donor immunoglobulin capable of binding to a desired antigen, such as an epitope on an antigen of interest, attached to DNA segments encoding acceptor human framework regions. Generally speaking, the invention in the Queen patent has applicability toward the design of substantially any humanized immunoglobulin. Queen explains that the DNA segments will typically include an expression control DNA sequence operably linked to the humanized immunoglobulin coding sequences, including naturally-associated or heterologous promoter regions. The expression control sequences can be eukaryotic promoter systems in vectors capable of transforming or transfecting eukaryotic host cells or the expression control sequences can be prokaryotic promoter systems in vectors capable of transforming or transfecting prokaryotic host cells. Once the vector has been incorporated into the appropriate host, the host is maintained under conditions suitable for high level expression of the introduced nucleotide sequences and as desired the collection and purification of the humanized light chains, heavy chains, light/heavy chain dimers or intact antibodies, binding fragments or other immunoglobulin forms may follow (Beychok, Cells of Immunoglobulin Synthesis, Academic Press, New York, (1979), which is incorporated herein by reference).

The invention also includes functional equivalents of the antibodies described herein. Functional equivalents have binding characteristics comparable to those of the antibodies, and include, for example, hybridized and single chain antibodies, as well as fragments thereof. Methods of producing such functional equivalents are disclosed in PCT Application WO 93/21319 and PCT Application WO 89/09622.

Functional equivalents include polypeptides with amino acid sequences substantially the same as the amino acid sequence of the variable or hypervariable regions of the antibodies. "Substantially the same" amino acid sequence is defined herein as a sequence with at least 70%, preferably at least about 80%, more preferably at least about 90%, even more preferably at least about 95%, and most preferably at least 99% homology to another amino acid sequence (or any integer in between 70 and 99), as determined by the FASTA search method in accordance with Pearson and Lipman, 1988 Proc. Nat'l. Acad. Sci. USA 85: 2444-2448. Chimeric or other hybrid antibodies have constant regions derived substantially or exclusively from human antibody constant regions and variable regions derived substantially or exclusively from the sequence of the variable region of a monoclonal antibody from each stable hybridoma.

Single chain antibodies (scFv) or Fv fragments are polypeptides that consist of the variable region of the heavy chain of the antibody linked to the variable region of the light chain, with or without an interconnecting linker. Thus, the Fv comprises an antibody combining site.

Functional equivalents of the antibodies of the invention further include fragments of antibodies that have the same, or substantially the same, binding characteristics to those of the whole antibody. Such fragments may contain one or both Fab fragments or the F(ab')$_2$ fragment. The antibody fragments contain all six complement determining regions of the whole antibody, although fragments containing fewer than all of such regions, such as three, four or five complement determining regions, are also functional. The functional equivalents are members of the IgG immunoglobulin class and subclasses thereof, but may be or may combine with any one of the following immunoglobulin classes: IgM, IgA, IgD, or IgE, and subclasses thereof. Heavy chains of various subclasses, such as the IgG subclasses, are responsible for different effector functions and thus, by choosing the desired heavy chain constant region, hybrid antibodies with desired effector function are produced. Exemplary constant regions are gamma 1 (IgG1), gamma 2 (IgG2), gamma 3 (IgG3), and gamma 4 (IgG4). The light chain constant region can be of the kappa or lambda type.

The immunoglobulins of the present invention can be monovalent, divalent or polyvalent. Monovalent immunoglobulins are dimers (HL) formed of a hybrid heavy chain associated through disulfide bridges with a hybrid light chain. Divalent immunoglobulins are tetramers ($H_2L_2$) formed of two dimers associated through at least one disulfide bridge.

Combinations

In one embodiment, the composition of the present invention comprises a combination of MLL1, MLL2, MOZ, menin, and WDR5 inhibitors described herein.

For example, in one embodiment the composition comprises a combination comprising at least two of a MLL1 inhibitor, MLL2 inhibitor, a MOZ inhibitor, a menin inhibitor, and a WDR5 inhibitor. In one embodiment, the present invention provides a composition, wherein the composition comprises a combination comprising at least three of a MLL1 inhibitor, MLL2 inhibitor, a MOZ inhibitor, a menin inhibitor, and a WDR5 inhibitor. In one embodiment, the present invention provides a composition, wherein the composition comprises a combination comprising at least four of a MLL1 inhibitor, MLL2 inhibitor, a MOZ inhibitor, a menin inhibitor, and a WDR5 inhibitor. In one embodiment, the present invention provides a composition, wherein the composition comprises a combination comprising a MLL1 inhibitor, MLL2 inhibitor, a MOZ inhibitor, a menin inhibitor, and a WDR5 inhibitor.

In certain embodiments, a composition comprising a combination of inhibitors described herein has an additive effect, wherein the overall effect of the combination is approximately equal to the sum of the effects of each individual inhibitor. In other embodiments, a composition comprising a combination of inhibitors described herein has a synergistic effect, wherein the overall effect of the combination is greater than the sum of the effects of each individual inhibitor.

A composition comprising a combination of inhibitors comprise individual inhibitors in any suitable ratio. For example, in one embodiment, the composition comprises a 1:1 ratio of two individual inhibitors. In one embodiment, the composition comprises a 1:1:1 ratio of three individual inhibitors. However, the combination is not limited to any particular ratio. Rather any ratio that is shown to be effective is encompassed.

Treatment Methods

The present invention provides methods of treating or preventing cancer administering an effective amount of a composition which inhibits tumor cell proliferation or reduces tumor growth.

In certain embodiments, the method of the invention comprises administering to a subject an effective amount of a composition that inhibits the expression, activity, or both of at least one of MLL1, MLL2, MOZ, menin, and WDR5 in a tumor cell of the subject. In one embodiment, the method comprises administering to a subject an effective amount of a composition that inhibits the expression, activity, or both of at least two of MLL1, MLL2, MOZ, menin, and WDR5 in a tumor cell of the subject. In one embodiment, the method comprises administering to a subject an effective amount of a composition that inhibits the expression, activity, or both of at least three of MLL1, MLL2, MOZ, menin, and WDR5 in a tumor cell of the subject. In one embodiment, the method comprises administering to a subject an effective amount of a composition that inhibits the expression, activity, or both of at least four of MLL1, MLL2, MOZ, menin, and WDR5 in a tumor cell of the subject. In one embodiment, the method comprises administering to a subject an effective amount of a composition that inhibits the expression, activity, or both of MLL1, MLL2, MOZ, menin, and WDR5 in a tumor cell of the subject.

In one embodiment, the method of the invention comprises administering to a subject an effective amount of a first composition that inhibits the expression, activity, or both of at least one of MLL1, MLL2, MOZ, menin, and WDR5 in a tumor cell of the subject and an effective amount of a second composition that inhibits the expression, activity, or both of at least one of MLL1, MLL2, MOZ, menin, and WDR5 in a tumor cell of the subject. In one embodiment, the method of the invention comprises administering to a subject an effective amount of a first composition that inhibits the expression, activity, or both of at least one of MLL1, MLL2, MOZ, menin, and WDR5 in a tumor cell of the subject, an effective amount of a second composition that inhibits the expression, activity, or both of at least one of MLL1, MLL2, MOZ, menin, and WDR5 in a tumor cell of the subject, and an effective amount of a third composition that inhibits the expression activity or both of at least one of MLL1, MLL2, MOZ, menin, and WDR5 in a tumor cell of the subject. In one embodiment, the method of the invention comprises administering to a subject an effective amount of a first composition that inhibits the expression, activity, or both of at least one of MLL1, MLL2, MOZ, menin, and WDR5 in a tumor cell of the subject, an effective amount of a second composition that inhibits the expression, activity, or both of at least one of MLL1, MLL2, MOZ, menin, and WDR5 in a tumor cell of the subject, an effective amount of a third composition that inhibits the expression activity or both of at least one of MLL1, MLL2, MOZ, menin, and WDR5 in a tumor cell of the subject, and an effective amount of a fourth composition that inhibits the expression activity or both of at least one of MLL1, MLL2, MOZ, menin, and WDR5 in a tumor cell of the subject. In one embodiment, the method of the invention comprises administering to a subject an effective amount of a first composition that inhibits the expression, activity, or both of at least one of MLL1, MLL2, MOZ, menin, and WDR5 in a tumor cell of the subject, an effective amount of a second composition that inhibits the expression, activity, or both of at least one of MLL1, MLL2, MOZ, menin, and WDR5 in a tumor cell of the subject, an effective amount of a third composition that inhibits the expression activity or both of at least one of MLL1, MLL2, MOZ, menin, and WDR5 in a tumor cell of the subject, an effective amount of a fourth composition that inhibits the expression activity or both of at least one of MLL1, MLL2, MOZ, menin, and WDR5 in a tumor cell of the subject, and an effective amount of a fifth composition that inhibits the expression activity or both of at least one of MLL1, MLL2, MOZ, menin, and WDR5 in a tumor cell of the subject.

The invention includes methods for the treatment of a p53 related disorder. As used herein, the term "p53 related disorder" refers to any disease, disorder, or condition which is caused or characterized by activity of p53. In certain embodiments, the method of the invention is used to treat any disease, disorder or condition which is caused or characterized by the activity of p53 gain of function (GOF) mutations. In certain instances p53 GOF mutations results in the tumor growth promoting activity of p53 in addition to, or instead of, the inhibition of the normal tumor suppressive activity of p53 that may occur in certain p53 mutations. In one embodiment, the invention includes methods for the treatment of cancer. In another embodiment, the invention includes methods for the prevention of cancer.

As discussed elsewhere herein, a wide variety of cancers are, at least in part associated with p53 GOF tumor promoting activity, which leads to perpetual tumor cell growth and tumor formation. As presented herein certain p53 GOF mutations results in the enhancement of epigenetic pathways, including enhancing the expression and activity of histone modifying enzymes. For example, certain p53 GOF mutations result in the enhanced expression and activity of MLL1 and/or MLL2, which in turn results in the methylation of histone H3 to produce H3K4me3. Further, certain p53 GOF mutations result in the enhanced expression and activity of MOZ, which in turn results in the acetylation of histone H3 to produce H3K9ac.

In certain embodiments, the method of the invention is used to treat any cancer associated with p53 GOF. The method is not limited to a particular type of cancer. Exemplary forms of cancer that is treatable by the method of the present invention include, but is not limited to, carcinomas, sarcomas, lymphomas, leukemia, blastomas, and germ cell cancers. For example, the methods of the invention are useful for treating or preventing breast cancer, lung cancer, pancreatic cancer, stomach cancer, bone cancer, ovarian cancer, prostate cancer, bladder cancer, cervical cancer, colon cancer, skin cancer, gliomas, esophageal cancer, oral cancer, gallbladder cancer, liver cancer, testicular cancer, uterine cancer, thyroid cancer, throat cancer, and the like.

The method of the invention may be used to treat or prevent cancer in any subject. In one embodiment, the subject is a mammal, including, but not limited to, a human, primate, cow, horse, sheep, goat, dog, cat, rodent, and the like.

MLL1, MLL2, MOZ, menin, or WDR5 activity can be inhibited using any method known to the skilled artisan. Examples of methods that inhibit MLL1, MLL2, MOZ, menin, or WDR5 activity, include but are not limited to, inhibiting expression of an endogenous gene encoding MLL1, MLL2, MOZ, menin, or WDR5, decreasing expression of mRNA encoding MLL1, MLL2, MOZ, menin, or WDR5, and inhibiting the function, activity, or stability of MLL1, MLL2, MOZ, menin, or WDR5. A MLL1, MLL2, MOZ, menin, or WDR5 inhibitor may therefore be a compound that decreases expression of a gene encoding MLL1, MLL2, MOZ, menin, or WDR5, decreases RNA half-life, stability, or expression of a mRNA encoding MLL1, MLL2, MOZ, menin, or WDR5 protein, or inhibits MLL1, MLL2, MOZ, menin, or WDR5 function, activity or stability. A MLL1, MLL2, MOZ, menin, or WDR5 inhibitor may be any type of compound, including but not limited to, a peptide, a nucleic acid, an aptamer, a peptidomimetic, and a small molecule, or combinations thereof.

MLL1, MLL2, MOZ, menin, or WDR5 inhibition may be accomplished either directly or indirectly. For example MLL1, MLL2, MOZ, menin, or WDR5 may be directly inhibited by compounds or compositions that directly interact with MLL1, MLL2, MOZ, menin, or WDR5, such as antibodies. Alternatively, MLL1, MLL2, MOZ, menin, or WDR5 may be inhibited indirectly by compounds or compositions that inhibit MLL1, MLL2, MOZ, menin, or WDR5 downstream effectors, or upstream regulators which up-regulate MLL1, MLL2, MOZ, menin, or WDR5 expression.

Decreasing expression of an endogenous gene includes providing a specific inhibitor of gene expression. Decreasing expression of mRNA or protein includes decreasing the half-life or stability of mRNA or decreasing expression of mRNA. Methods of decreasing expression of MLL1, MLL2, MOZ, menin, or WDR5 include, but are not limited to, methods that use an siRNA, a microRNA, an antisense nucleic acid, a ribozyme, an expression vector encoding a transdominant negative mutant, a peptide, a small molecule, and combinations thereof.

In one embodiment, the method comprises an administering an inhibitor that inhibits the interaction of MLL1, MLL2, MOZ, menin, or WDR5 in a protein complex. For example, in one embodiment, the method comprises administering an inhibitor of the interaction of menin and an MLL. In one embodiment, the method comprises administering an inhibitor of the interaction of WDR5 and an MLL.

Administration of a MLL1, MLL2, MOZ, menin, or WDR5 inhibitor in a method of treatment can be achieved in a number of different ways, using methods known in the art.

It will be appreciated that a MLL1, MLL2, MOZ, menin, or WDR5 inhibitor of the invention may be administered to a subject either alone, or in conjunction with another therapeutic agent or therapy, including but not limited to chemotherapy, radiotherapy, surgery, and antibody therapy. For example, in one embodiment, the method provides for using a lower than typical dose of a particular cancer therapy in combination with the one or more inhibitors of the invention, thus mitigating the side effects of using a typical dose on its own.

In one embodiment, MLL1, MLL2, MOZ, menin, or WDR5 inhibitor is administered to a subject. The inhibitor may also be a hybrid or fusion composition to facilitate, for instance, delivery to target cells or efficacy. In one embodiment, a hybrid composition may comprise a tissue-specific targeting sequence. For example, in one embodiment, the inhibitor is targeted to cell expressing a tumor-specific or tumor-associated antigen.

In one embodiment, the invention includes a method comprising administering a combination of inhibitors described herein. In certain embodiments, the method has an additive effect, wherein the overall effect of the administering a combination of inhibitors is approximately equal to the sum of the effects of administering each individual inhibitor. In other embodiments, the method has a synergistic effect, wherein the overall effect of administering a combination of inhibitors is greater than the sum of the effects of administering each individual inhibitor.

The method comprises administering a combination of inhibitors in any suitable ratio. For example, in one embodiment, the method comprises administering three individual inhibitors at a 1:1:1 ratio. In one embodiment, the method comprises administering two individual inhibitors at a 1:1 ratio. However, the method is not limited to any particular ratio. Rather any ratio that is shown to be effective is encompassed.

In some embodiments, the method of the present invention includes developing a personalized treatment regimen for a subject with cancer. Such methods can include, for example, identifying a subject with cancer cells having a particular p53 GOF mutation, and administering a therapeutically effective amount of a composition that inhibits one or more histone modifying enzymes (e.g, MLL1, MLL2, MOZ) to the subject, where the particular composition is dependent upon the p53 GOF mutation present in the cancer cell. For example, the present invention is based in part upon the finding that different p53 GOF mutations regulate different combinations of epigenetic pathways that can lead to tumor growth and proliferation. Therefore, effective treatment of the subject is dependent upon the type of p53 GOF mutation present in the particular subject's cancer, thereby providing personalized treatment.

Exemplary p53 GOF mutations that regulate epigenetic pathways, for example enhancing the activity of histone modifying enzymes, include, but are not limited to p53 R175H (where arginine (R) at position 175 of p53 is replaced by histidine (H)); p53 R248Q (where arginine (R) at position 248 of p53 is replaced by glutamine (Q)); p53 R248W (where arginine (R) at position 248 of p53 is replaced by tryptophan (W)); p53 R249S (where arginine (R) at position 249 of p53 is replaced by serine (S); and p53 R273H (where arginine (R) at position 273 of p53 is replaced by histidine (H)).

Determination of a particular p53 GOF mutation of a tumor or tumor cell of the subject, may be performed using any known methods of mutational analysis, including but not limited to denaturing gradient gel electrophoresis (DGGE), constant denaturing gel electrophoresis (CDGE), temporal temperature gradient gel electrophoresis (TTGE), single-strand conformation polymorphism (SSCP), high resolution melt (HRM) analysis, Fluorescence in situ hybridization (FISH), PCR, DNA sequencing, immunoassays, enzyme linked immunosorbent assays (ELISA), radioimmunoassays (RIA), Western blotting, dot blotting, FACS analysis, use of biosensors, and the like. In certain embodiments the p53 GOF mutation is relative to the wild-type p53 amino acid sequence of the species. The amino acid sequences of wildtype p53 are known in the art. For example, exemplary canonical amino acid sequences of human wildtype p53 can be found at least at NCBI accession no: AAC12971 and NCBI accession no. NP_000537.3.

In one embodiment, the method comprises obtaining a bodily sample from the subject, and analyzing the presence of one or more p53 GOF mutations in the sample. In one embodiment, the sample may be a sample of the tumor of the subject. In certain embodiments, the tumor sample may be obtained via a biopsy or other surgical procedure.

In some embodiments, the methods can include determining the most appropriate treatment for a subject confirmed to have cancer (e.g., by determining the particular p53 GOF mutation present in the cancer cell of the subject), developing a treatment regimen for the subject, and optionally administering to the subject a composition in accordance with the treatment regimen. These methods can include, for example:

(i) selecting a subject having cancer; detecting the presence of the R248Q p53 GOF mutation in the subject's cancer (e.g., in a cancer cell obtained from the subject (e.g., obtained by biopsy); and, if R248Q p53 GOF is detected, providing the subject with a personalized treatment regimen that includes administering an effective amount of an inhibitor of MLL1 and an effective amount of an inhibitor of MLL2 to the subject. For example, it is shown herein that cells having the R248Q p53 GOF mutation demonstrate that p53 GOF is bound to MLL1 and MLL2. In some embodiments, the method includes administering the one or more inhibitors to the subject under conditions and for a period of time sufficient to treat the subject;

(ii) selecting a subject having cancer; detecting the presence of the R248W p53 GOF mutation in the subject's cancer (e.g., in a cancer cell obtained from the subject (e.g., obtained by biopsy); and, if R248W p53 GOF is detected, providing the subject with a personalized treatment regimen that includes administering an effective amount of an inhibitor of MLL1, an effective amount of an inhibitor of MLL2, and an effective amount of an inhibitor of MOZ to the subject. For example, it is shown herein that cells having the R248W p53 GOF mutation demonstrate that p53 GOF is bound mostly to MLL2 and MOZ, with some bound to MLL1. In some embodiments, the method includes administering the one or more inhibitors to the subject under conditions and for a period of time sufficient to treat the subject;

(iii) selecting a subject having cancer; detecting the presence of the R249S p53 GOF mutation in the subject's cancer (e.g., in a cancer cell obtained from the subject (e.g., obtained by biopsy); and, if R249S p53 GOF is detected, providing the subject with a personalized treatment regimen that includes administering an effective amount of an inhibitor of MLL1, an effective amount of an inhibitor of MLL2, and an effective amount of an inhibitor of MOZ to the subject. For example, it is shown herein that cells having the R249S p53 GOF mutation demonstrate that p53 GOF is bound mostly to MOZ and MLL2 and some to MLL1. In some embodiments, the method includes administering the one or more inhibitors to the subject under conditions and for a period of time sufficient to treat the subject;

(iv) selecting a subject having cancer; detecting the presence of the R273H p53 GOF mutation in the subject's cancer (e.g., in a cancer cell obtained from the subject (e.g., obtained by biopsy); and, if R273H p53 GOF is detected, providing the subject with a personalized treatment regimen that includes administering an effective amount of an inhibitor of MLL1, an effective amount of an inhibitor of MLL2, and an effective amount of an inhibitor of MOZ to the subject. For example, it is shown herein that cells having the R273H p53 GOF mutation demonstrate that p53 GOF is bound to mostly to MLL1 and MLL2, with some bound to MOZ. In some embodiments, the method includes administering the one or more inhibitors to the subject under conditions and for a period of time sufficient to treat the subject.

It should be noted that methods (i)-(iv) can be performed independently or together and in any order. Any of methods (i)-(iv) can also include monitoring or evaluating the subject during and after administration of the composition to determine the efficacy of the treatment, and, if necessary, adjusting treatment (e.g., by altering the composition, by increasing the dose of a single administration of the composition, by increasing the number of doses of the composition administered per day, and/or by increasing the number of days the composition is administered) to improve efficacy.

In certain embodiments, the method comprises determining the most appropriate treatment for a subject confirmed to have cancer, developing a treatment regimen for the subject, and optionally administering to the subject a composition in accordance with the treatment regimen, wherein the method comprises evaluating the epigenetic signature of a cell of the subject. For example, in certain embodiments, a cell, for example a tumor cell, may be analyzed for the presence, amount, or location of histone modifications. In one embodiment, the methylation state of histones of the cell may be evaluated, including but not limited to the change in amount or location of H3K4 methylation, such as H3K4 mono-methylation (H3K4me1), H3K4 di-methylation (H3K4me2), or H3K4 tri-methylation (H3K4me3). In one embodiment, the acetylation state of histones of the cell may be evaluated, including but not limited to the change in amount and/or location of H3K9 acetylation (H3K9ac). The epigenetic signature of a cell of the subject may be investigated using known techniques in the art, including, but not limited to, immunoassays, western blotting, chromatin immunoprecipitation sequencing (ChIP-seq), methylated DNA immunoprecipitation (meDIP), DNA methylation quantification, DNA methylation quantification, histone methylation quantification, histone methyltransferase assay, histone acetylation quantification, histone acetyltransferase (HAT) assay, and the like.

Dosage and Formulation (Pharmaceutical Compositions)

The present invention envisions treating a disease, for example, cancer and the like, in a subject by the administration of therapeutic agent, e.g. an inhibitor of MLL1, MLL2, MOZ, menin, WDR5 or a combination thereof.

Administration of the therapeutic agent in accordance with the present invention may be continuous or intermittent, depending, for example, upon the recipient's physiological condition, whether the purpose of the administration is therapeutic or prophylactic, and other factors known to skilled practitioners. The administration of the agents of the invention may be essentially continuous over a preselected period of time or may be in a series of spaced doses. Both local and systemic administration is contemplated. The amount administered will vary depending on various factors including, but not limited to, the composition chosen, the particular disease, the weight, the physical condition, and the age of the subject, and whether prevention or treatment is to be achieved. Such factors can be readily determined by the clinician employing animal models or other test systems which are well known to the art One or more suitable unit dosage forms having the therapeutic agent(s) of the invention, which, as discussed below, may optionally be formulated for sustained release (for example using microencapsulation, see WO 94/07529, and U.S. Pat. No. 4,962,091 the disclosures of which are incorporated by reference herein), can be administered by a variety of routes including parenteral, including by intravenous and intramuscular routes, as well as by direct injection into the diseased tissue. For example, the therapeutic agent or modified cell may be directly injected into the tumor. The formulations may, where appropriate, be conveniently presented in discrete unit dosage forms and may be prepared by any of the methods well known to pharmacy. Such methods may include the step of bringing into association the therapeutic agent with liquid carriers, solid matrices, semi-solid carriers, finely divided solid carriers or combinations thereof, and then, if necessary, introducing or shaping the product into the desired delivery system.

The therapeutic and prophylactic methods of the invention encompass the use of pharmaceutical compositions comprising a MLL1 inhibitor, a MLL2 inhibitor, a MOZ inhibitor, a menin inhibitor, a WDR5 inhibitor, or a combination thereof to practice the methods of the invention. The pharmaceutical compositions useful for practicing the invention may be administered to deliver a dose of from ng/kg/day and 100 mg/kg/day. In one embodiment, the invention envisions administration of a dose which results in a concentration of the composition of the present invention from 1 µM and 10 µM in a mammal.

Typically, dosages which may be administered in a method of the invention to a mammal, preferably a human, range in amount from 0.5 µg to about 50 mg per kilogram of body weight of the mammal, while the precise dosage administered will vary depending upon any number of factors, including but not limited to, the type of mammal and type of disease state being treated, the age of the mammal and the route of administration. Preferably, the dosage of the compound will vary from about 1 µg to about 10 mg per kilogram of body weight of the mammal. More preferably, the dosage will vary from about 3 µg to about 1 mg per kilogram of body weight of the mammal.

The compound may be administered to a mammal as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the mammal, etc.

When the therapeutic agents of the invention are prepared for administration, they are preferably combined with a pharmaceutically acceptable carrier, diluent or excipient to form a pharmaceutical formulation, or unit dosage form. The total active ingredients in such formulations include from 0.1 to 99.9% by weight of the formulation. A "pharmaceutically acceptable" is a carrier, diluent, excipient, and/or salt that is compatible with the other ingredients of the formulation, and not deleterious to the recipient thereof. The active ingredient for administration may be present as a powder or as granules; as a solution, a suspension or an emulsion.

Pharmaceutical formulations containing the therapeutic agents of the invention can be prepared by procedures known in the art using well known and readily available ingredients. The therapeutic agents of the invention can also be formulated as solutions appropriate for parenteral administration, for instance by intramuscular, subcutaneous or intravenous routes.

The pharmaceutical formulations of the therapeutic agents of the invention can also take the form of an aqueous or anhydrous solution or dispersion, or alternatively the form of an emulsion or suspension.

Thus, the therapeutic agent may be formulated for parenteral administration (e.g., by injection, for example, bolus injection or continuous infusion) and may be presented in unit dose form in ampules, pre-filled syringes, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

It will be appreciated that the unit content of active ingredient or ingredients contained in an individual aerosol dose of each dosage form need not in itself constitute an effective amount for treating the particular indication or disease since the necessary effective amount can be reached by administration of a plurality of dosage units. Moreover, the effective amount may be achieved using less than the dose in the dosage form, either individually, or in a series of administrations.

The pharmaceutical formulations of the present invention may include, as optional ingredients, pharmaceutically acceptable carriers, diluents, solubilizing or emulsifying agents, and salts of the type that are well-known in the art. Specific non-limiting examples of the carriers and/or diluents that are useful in the pharmaceutical formulations of the present invention include water and physiologically acceptable buffered saline solutions, such as phosphate buffered saline solutions pH 7.0-8.0.

The expression vectors, transduced cells, polynucleotides and polypeptides (active ingredients) of this invention can be formulated and administered to treat a variety of disease states by any means that produces contact of the active ingredient with the agent's site of action in the body of the organism. They can be administered by any conventional means available for use in conjunction with pharmaceuticals, either as individual therapeutic active ingredients or in a combination of therapeutic active ingredients. They can be administered alone, but are generally administered with a pharmaceutical carrier selected on the basis of the chosen route of administration and standard pharmaceutical practice.

In general, water, suitable oil, saline, aqueous dextrose (glucose), and related sugar solutions and glycols such as propylene glycol or polyethylene glycols are suitable carriers for parenteral solutions. Solutions for parenteral administration contain the active ingredient, suitable stabilizing agents and, if necessary, buffer substances. Antioxidizing agents such as sodium bisulfate, sodium sulfite or ascorbic acid, either alone or combined, are suitable stabilizing agents. Also used are citric acid and its salts and sodium Ethylenediaminetetraacetic acid (EDTA). In addition, parenteral solutions can contain preservatives such as benzalkonium chloride, methyl- or propyl-paraben and chlorobutanol. Suitable pharmaceutical carriers are described in Remington's Pharmaceutical Sciences, a standard reference text in this field.

The active ingredients of the invention may be formulated to be suspended in a pharmaceutically acceptable composition suitable for use in mammals and in particular, in humans. Such formulations include the use of adjuvants such as muramyl dipeptide derivatives (MDP) or analogs that are described in U.S. Pat. Nos. 4,082,735; 4,082,736; 4,101,536; 4,185,089; 4,235,771; and 4,406,890. Other adjuvants, which are useful, include alum (Pierce Chemical Co.), lipid A, trehalose dimycolate and dimethyldioctadecylammonium bromide (DDA), Freund's adjuvant, and IL-12. Other components may include a polyoxypropylene-polyoxyethylene block polymer (Pluronic®), a non-ionic surfactant, and a metabolizable oil such as squalene (U.S. Pat. No. 4,606,918).

Additionally, standard pharmaceutical methods can be employed to control the duration of action. These are well known in the art and include control release preparations and can include appropriate macromolecules, for example polymers, polyesters, polyamino acids, polyvinyl, pyrolidone, ethylenevinylacetate, methyl cellulose, carboxymethyl cellulose or protamine sulfate. The concentration of macromolecules as well as the methods of incorporation can be adjusted in order to control release. Additionally, the agent can be incorporated into particles of polymeric materials such as polyesters, polyamino acids, hydrogels, poly (lactic acid) or ethylenevinylacetate copolymers. In addition to being incorporated, these agents can also be used to trap the compound in microcapsules.

Accordingly, the pharmaceutical composition of the present invention may be delivered via various routes and to various sites in a mammal body to achieve a particular effect (see, e.g., Rosenfeld et al., 1991; Rosenfeld et al., 1991a; Jaffe et al., supra; Berkner, supra). One skilled in the art will recognize that although more than one route can be used for administration, a particular route can provide a more immediate and more effective reaction than another route. Local or systemic delivery can be accomplished by administration comprising application or instillation of the formulation into body cavities, inhalation or insufflation of an aerosol, or by parenteral introduction, comprising intramuscular, intravenous, peritoneal, subcutaneous, intradermal, as well as topical administration.

The active ingredients of the present invention can be provided in unit dosage form wherein each dosage unit, e.g., a teaspoonful, tablet, solution, or suppository, contains a predetermined amount of the composition, alone or in appropriate combination with other active agents. The term "unit dosage form" as used herein refers to physically discrete units suitable as unitary dosages for human and mammal subjects, each unit containing a predetermined quantity of the compositions of the present invention, alone or in combination with other active agents, calculated in an amount sufficient to produce the desired effect, in association with a pharmaceutically acceptable diluent, carrier, or vehicle, where appropriate. The specifications for the unit dosage forms of the present invention depend on the particular effect to be achieved and the particular pharmacodynamics associated with the pharmaceutical composition in the particular host.

These methods described herein are by no means all-inclusive, and further methods to suit the specific application will be apparent to the ordinary skilled artisan. Moreover, the effective amount of the compositions can be further approximated through analogy to compounds known to exert the desired effect.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way the remainder of the disclosure.

Example 1

Prevalent p53 Gain-of-Function Mutants Activate Epigenetic Pathways

The data presented herein demonstrates that p53 GOF mutations result in the activation of various epigenetic pathways. Interestingly and unexpectedly, it is shown that in certain instances, the particular type of epigenetic pathway activated, or extent of activation, is dependent upon the particular type of p53 GOF mutation.

Five cell lines derived from patients with breast cancer were obtained from the ATCC. Four of these cell lines contained a mutated GOF p53, and one cell line was wild-type for the p53 gene. Experiments were conducted to examine the genome-wide binding of the wild-type and mutant p53 proteins using ChIP-seq (chromatin immunoprecipitation-sequencing). ChIP-seq was also conducted on a commonly used laboratory cell line (MCF7) which is another breast cancer line with wild-type p53. The list breast cancer cell types, along with the type of p53 mutation (or wildtype (WT)), is listed below.

MCF7 (WT p53)
MDA-MB-175VII (WT p53)
MDA-MB-468 (R273H)
SK-BR-3 (R175H)
HCC70 (R248Q)
BT549 (R249S)

After performing ChIP-seq experiments and alignment of sequencing reads to the human genome, it was determined where wild-type and the mutant p53 proteins were bound within the genome. p53 peaks specific to the MDA468 cell line were mapped to the nearest downstream TSS (annotation was ENSEMBL transcripts). The resulting gene list was processed using DAVID to find significantly enriched (gene ontology) GO categories. Of the GO terms with at least 5 associated genes, a 5-fold enrichment over genomic background, and satisfying a 1% FDR, the two terms with the highest fold enrichment were for histone methyltransferase genes. This group has five genes: MLL, MLL2, PPP1CC, RBBP5, and OGT (FIG. 1A). This prompted a further look into other epigenetic factors, where additional p53 GOF-targeted genes common among multiple p53 mutants were found: MOZ, SMARCD2, TTK, TCEA, STAT3, CTNNB1, JMJD1B, TAF3, and BAP1. The apparent GOF regulation of MLL and MLL2 prompted the investigation of aberrant H3K4me3 (the product of MLL activity) as a mode of indirect gene activation by p53. Further, MOZ activity and aberrant H3K9ac (the product of MOZ activity) was also investigated.

Figure 1B:
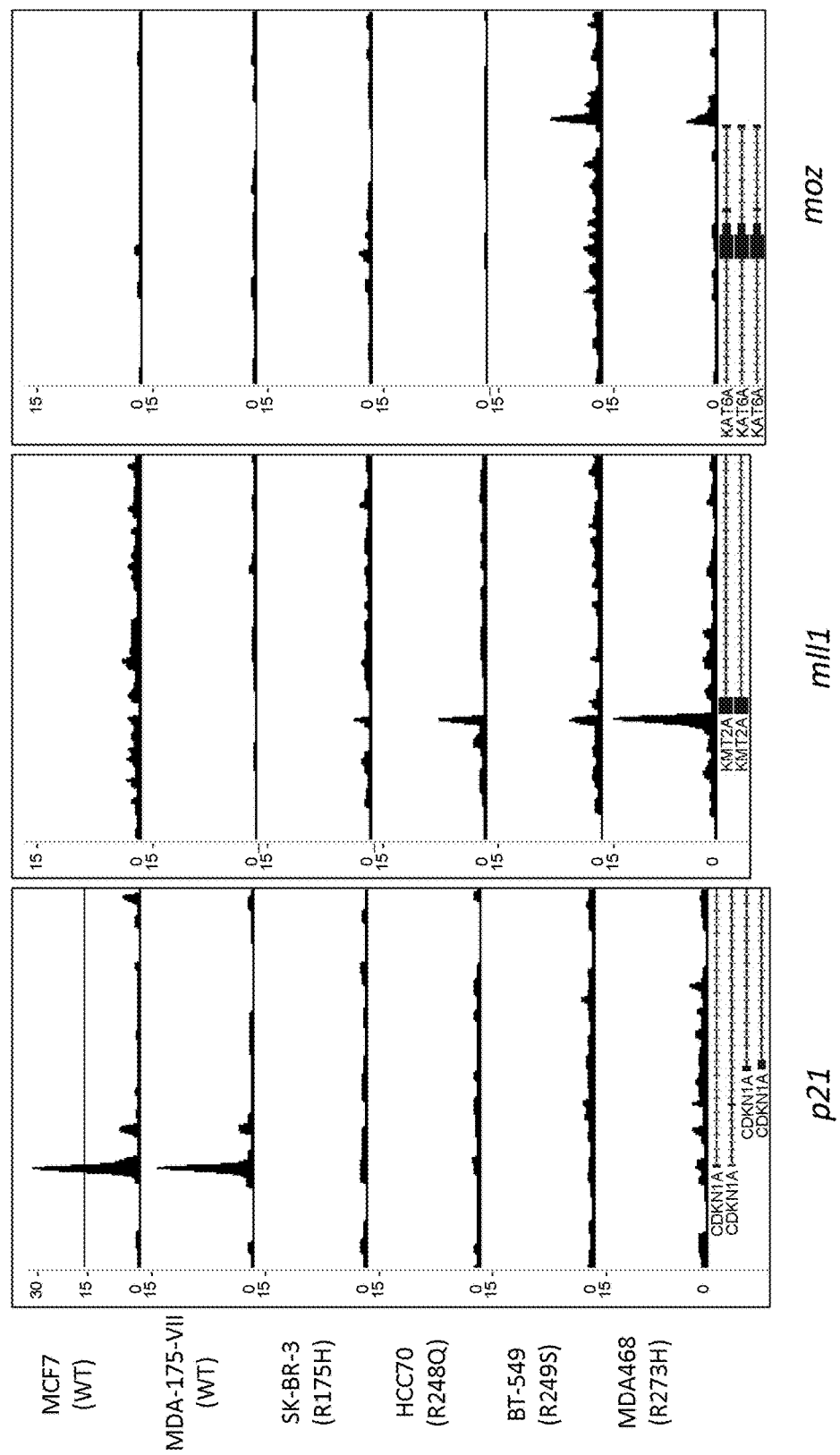

FIG. 1B depicts the UCSC Genome Browser tracks of wild-type and mutant p53 ChIP-seq experiments for 3 genomic locations. The X-axis represents the gene of interest (in this case, the wild-type p53 target p21, and mll1 and moz, two newly discovered mutant p53 GOF targets. The Y-axis represents the enrichment of each p53 binding event.

Figure 5A:
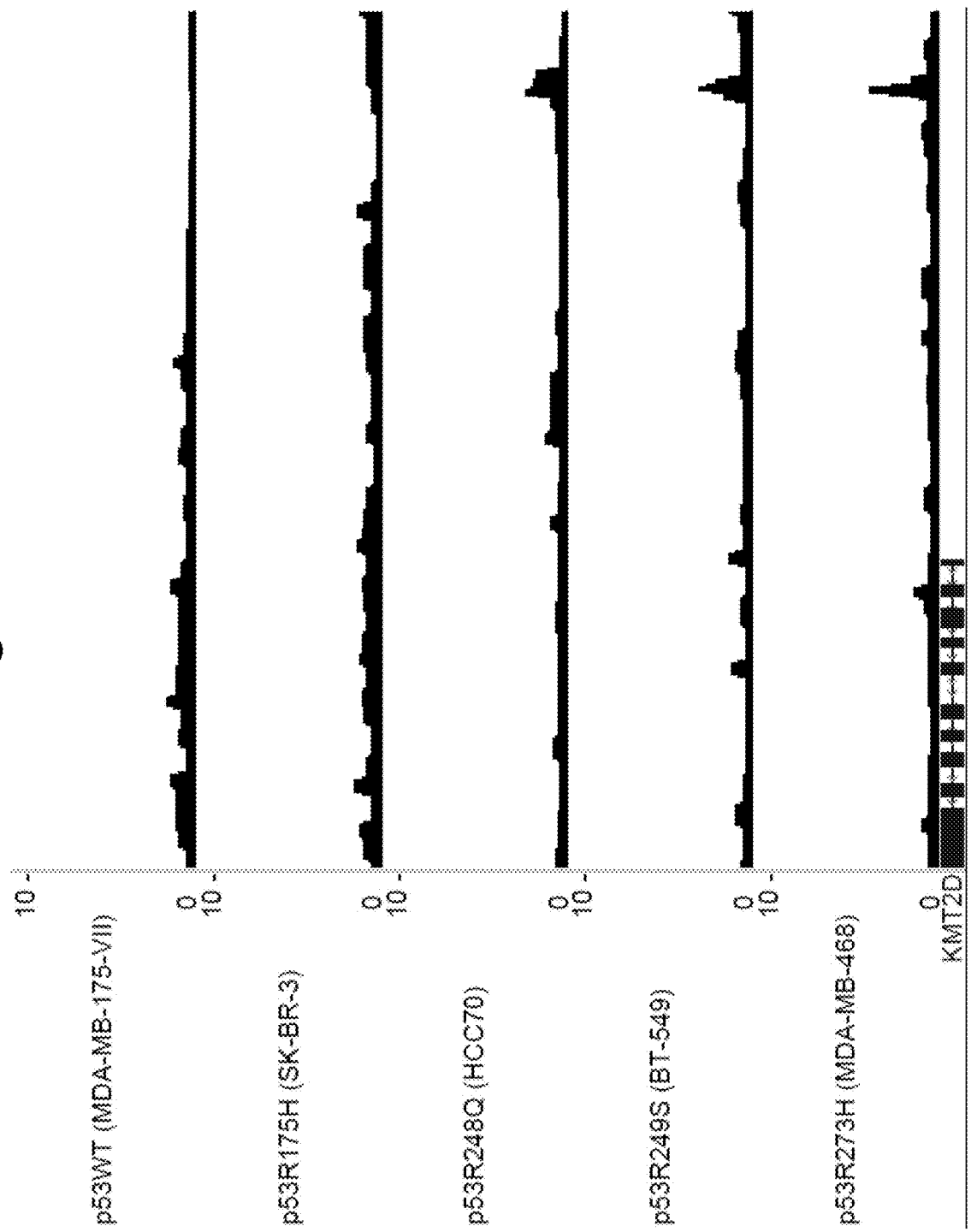
FIG. 5A and FIG. 5B, depict tracks of wildtype and p53 GOF mutant ChIP-seq experiments for mll2 (FIG. 5A) and for p53 R248W mutation for mll1, mll2, and moz.
Figure 5B:
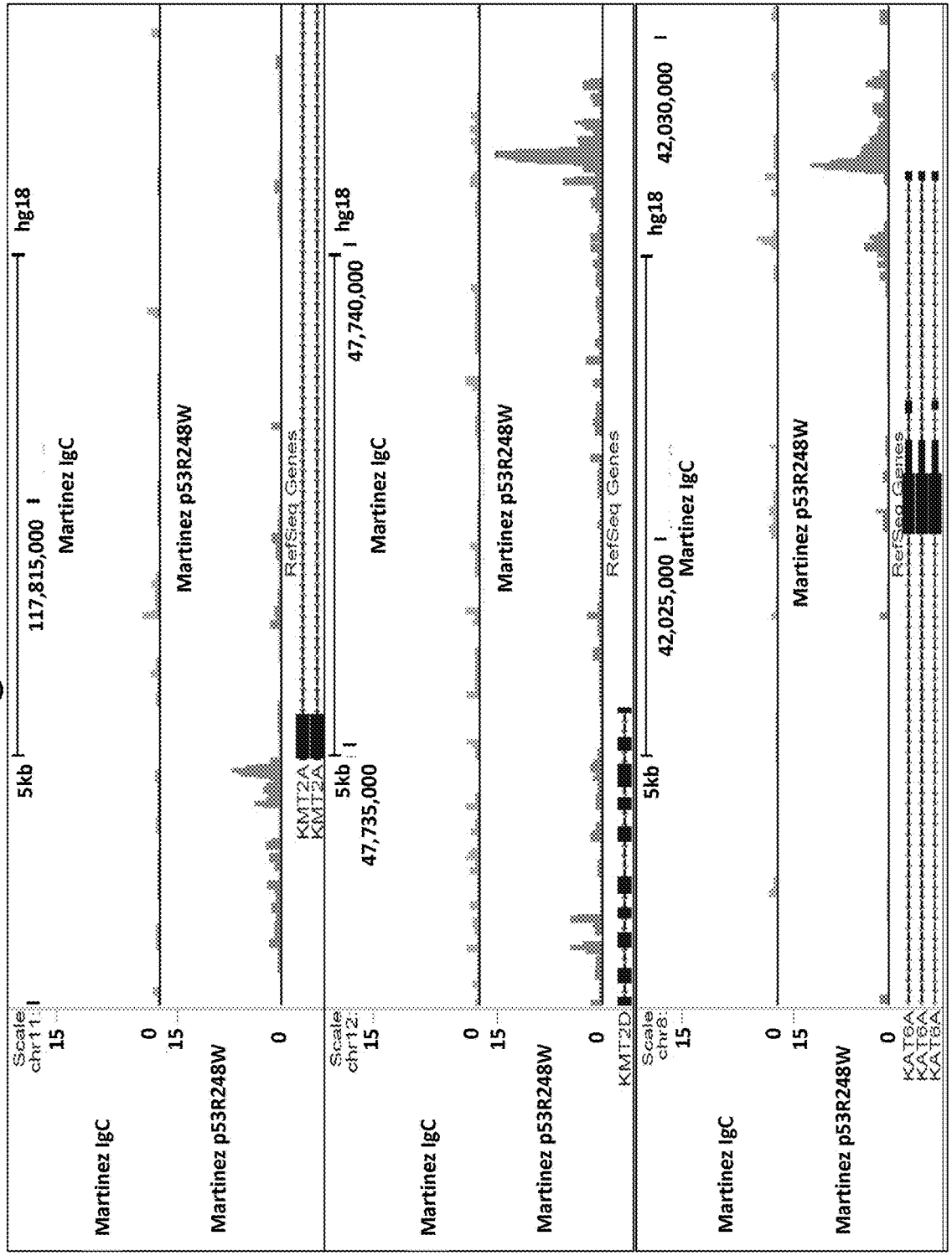

The top two panels (labeled MCF7 (WT) and MDA-175-VII (WT)) represent the activity and binding of the wild-type p53 protein at all 3 genomic locations of interest. The bottom 4 panels represent binding of the mutant p53 GOF protein. Note that the wild-type p53 protein does not bind to mll1 or moz target genes, while 3 of the 4 mutant p53 proteins are present. The tracks of wildtype and mutant p53 to mll2 target genes is shown in FIG. 5A, demonstrating that several of the mutations also result in binding to mll2 (FIG. 5A). FIG. 5B depicts the reanalysis of ChIP-seq data from Li-Frumeni cells with R248W cells (Do et al., 2012, Genes Dev., 26(8):830-45). The mutant p53 from the SK-BR-3 (R175H) cell line does not appear to bind to the epigenetic targets, presumably due to the R175H mutation affecting a different portion of the p53 protein. This data suggests that it may be possible to predict the response of a mutant p53 tumor to MLL or MOZ inhibition based on its mutational status and predicted genome-wide binding.

Figure 1C:
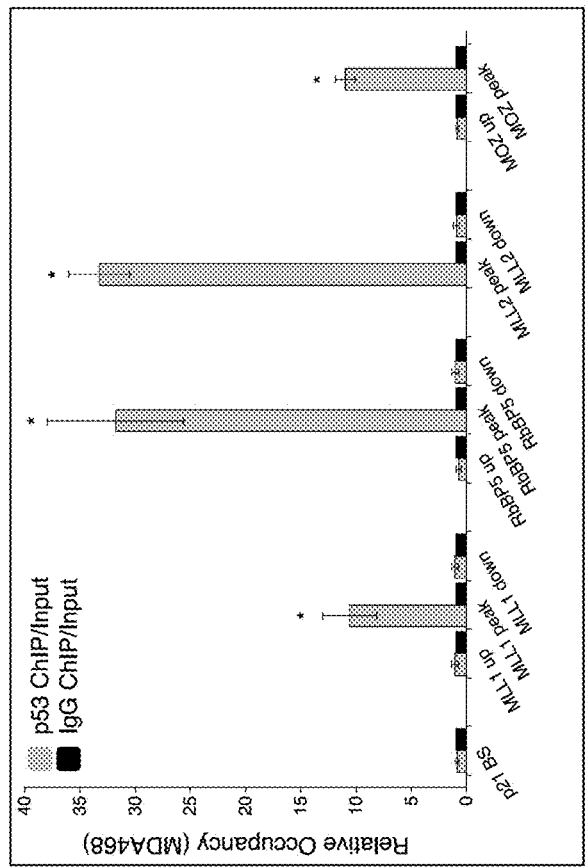

Experiments were conducted to validate the mutant p53 from the MDA468 breast cancer line specifically interacted with the epigenetic targets, but not to regions nearby or to wildtype p53 targets (FIG. 1C). Further, it was observed that wildtype p53 does not bind to the epigenetic targets (FIG. 1C).

Figure 1D:
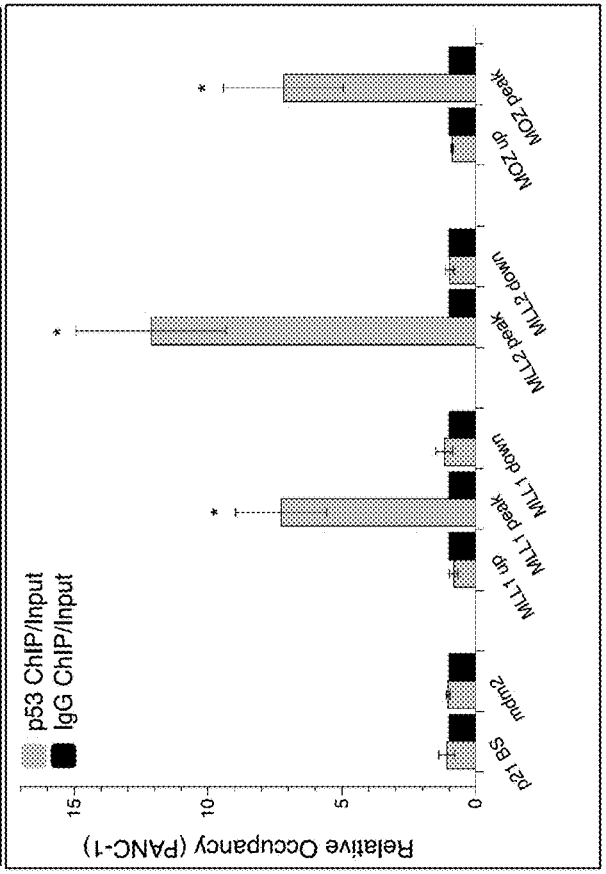
Figure 1E:
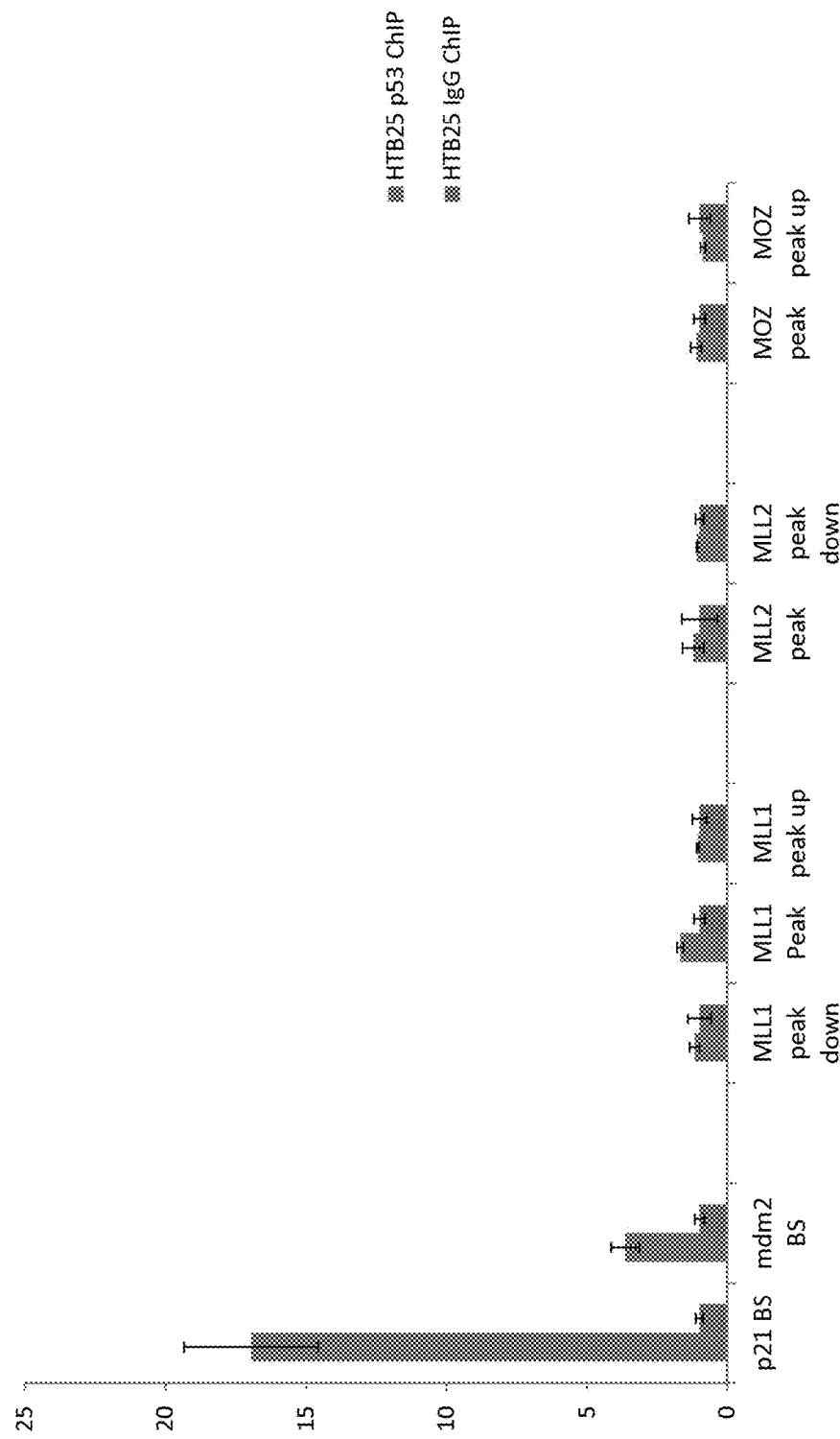

An experiment was conducted with a pancreatic cell line (Panc1) harboring the p53 R273H mutation, showing that p53 GOF in this cell line also specifically targets the epigenetic targets, but not wild-type p53 targets (FIG. 1D). Very interestingly, the same p53 mutation in the PANC1 cell line is seen in the MDA468 breast cancer line (p53 R273H), suggesting a potential common mechanism between cancers of different lineages that contain mutated p53.

Figure 2A:
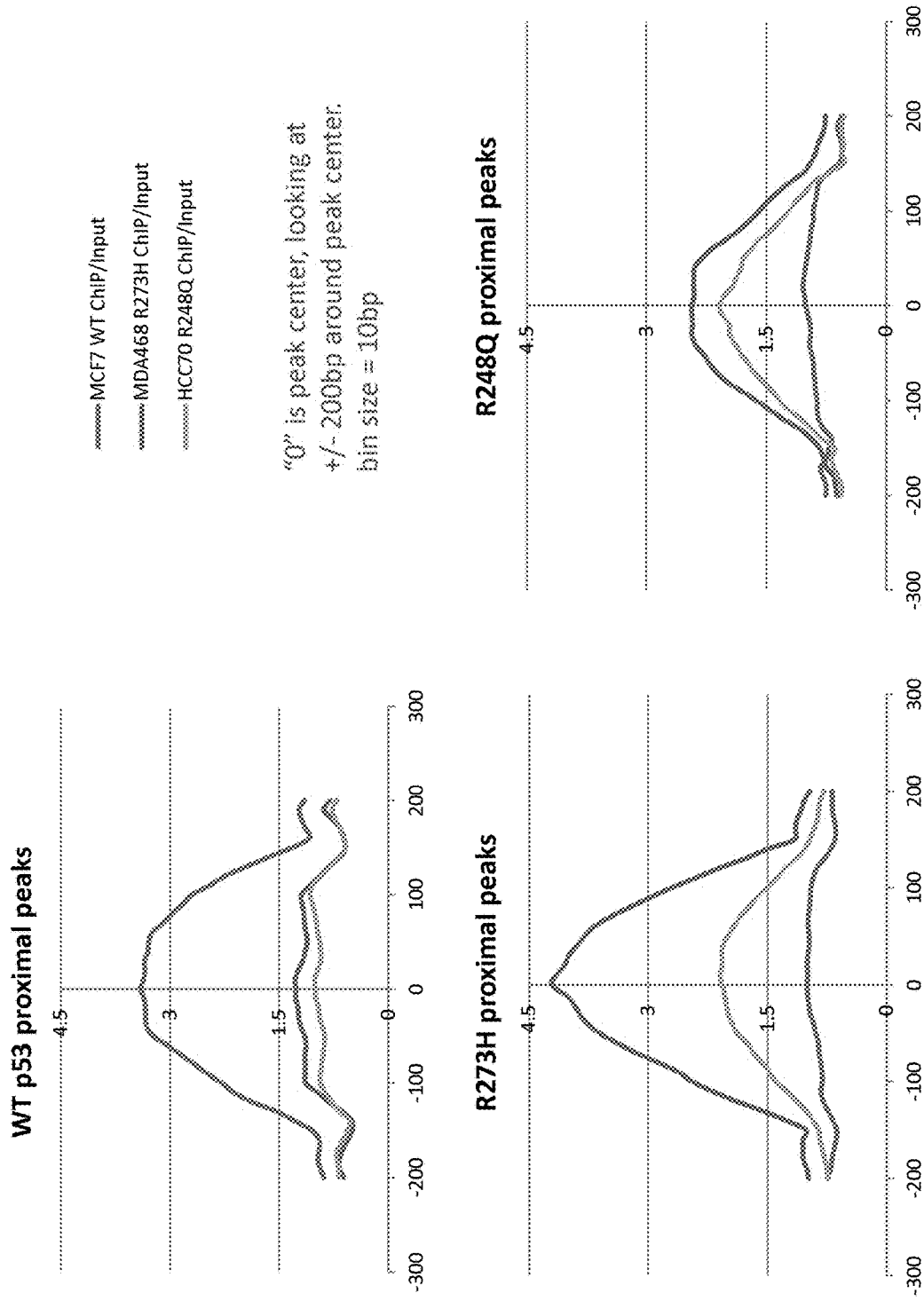
FIG. 2A and FIG. 2B, depicts the results of ChIP-seq statistics and motif analysis.

ChIP-seq statistics and motif analysis was performed to compare the differences between wildtype and GOF mutant p53 (FIG. 2A). The WT-p53 proximal peaks demonstrates that the mutant p53 proteins (bottom two traces) are not enriched (bound) to the same genomic regions as the wild-type protein (top trace). The other panels (labeled R273H proximal peaks and R248Q proximal peaks) demonstrate that the different p53 GOF mutants (top two traces in these panels) bind to the same genomic locations as each other, but that the wild-type protein is absent. These data further support the idea that the wild-type p53 protein does not bind to epigenetic targets, but that the mutants share common target genes and a potential common mechanism.

Figure 2B:
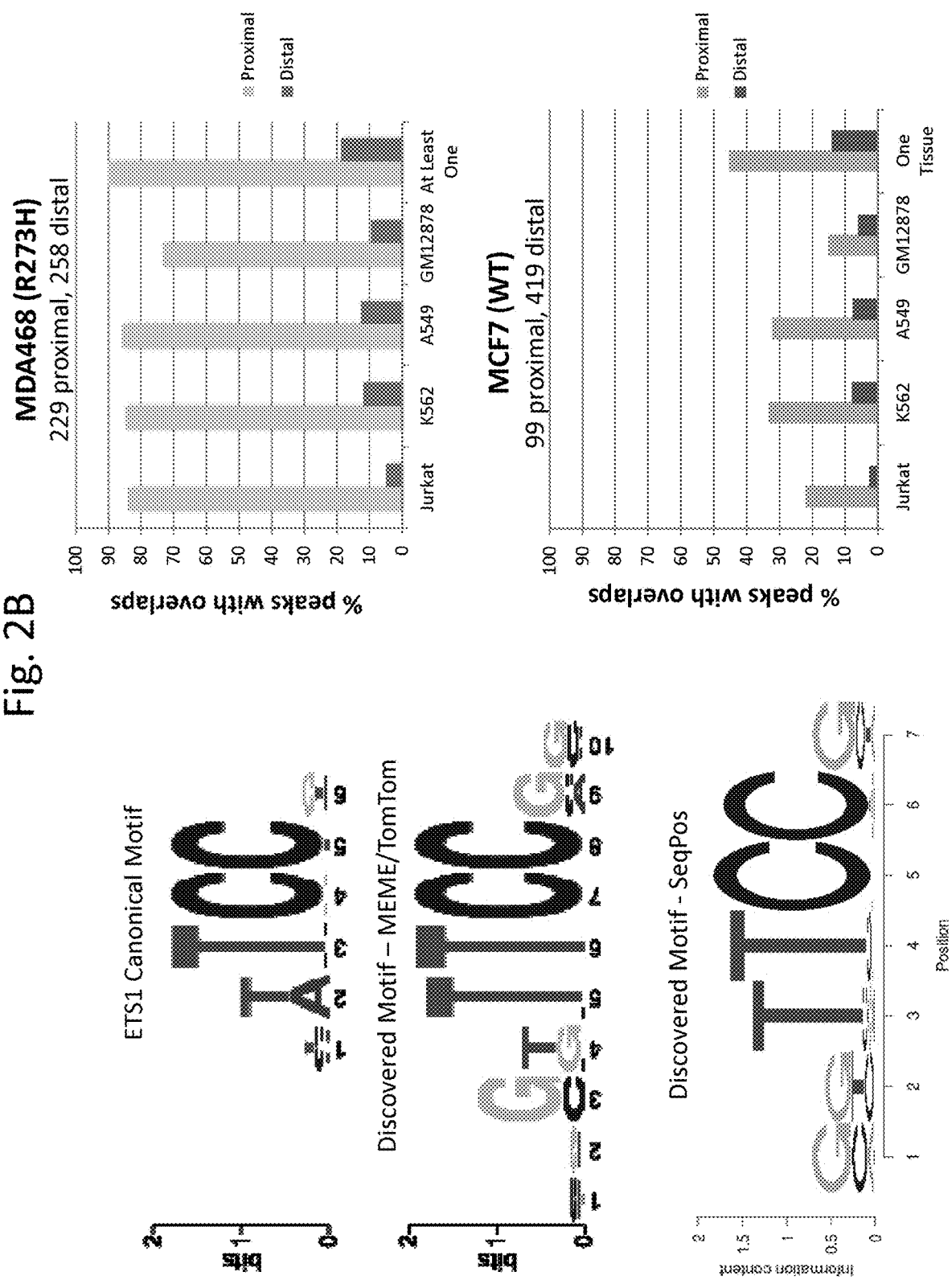

Since the mutant p53 protein appears to bind to new genomic regions (compared to the wild-type protein) it was sought to determine whether the mutant p53 protein had a canonical DNA binding motif that could help explain its target gene binding. It was determined that the mutant GOF p53 proteins appear to bind to regions with a canonical ETS1 (another DNA binding transcription factor) motif (FIG. 2B). This is unlike the wild-type protein, which binds to ETS1 regions with a much lower frequency than the mutant p53 (FIG. 2B; graphs on right). These data suggest that the mutant p53 GOF proteins either A) gain the ability to bind DNA with the ETS1 motif or B) interact with ETS-family DNA binding proteins.

Figure 3:
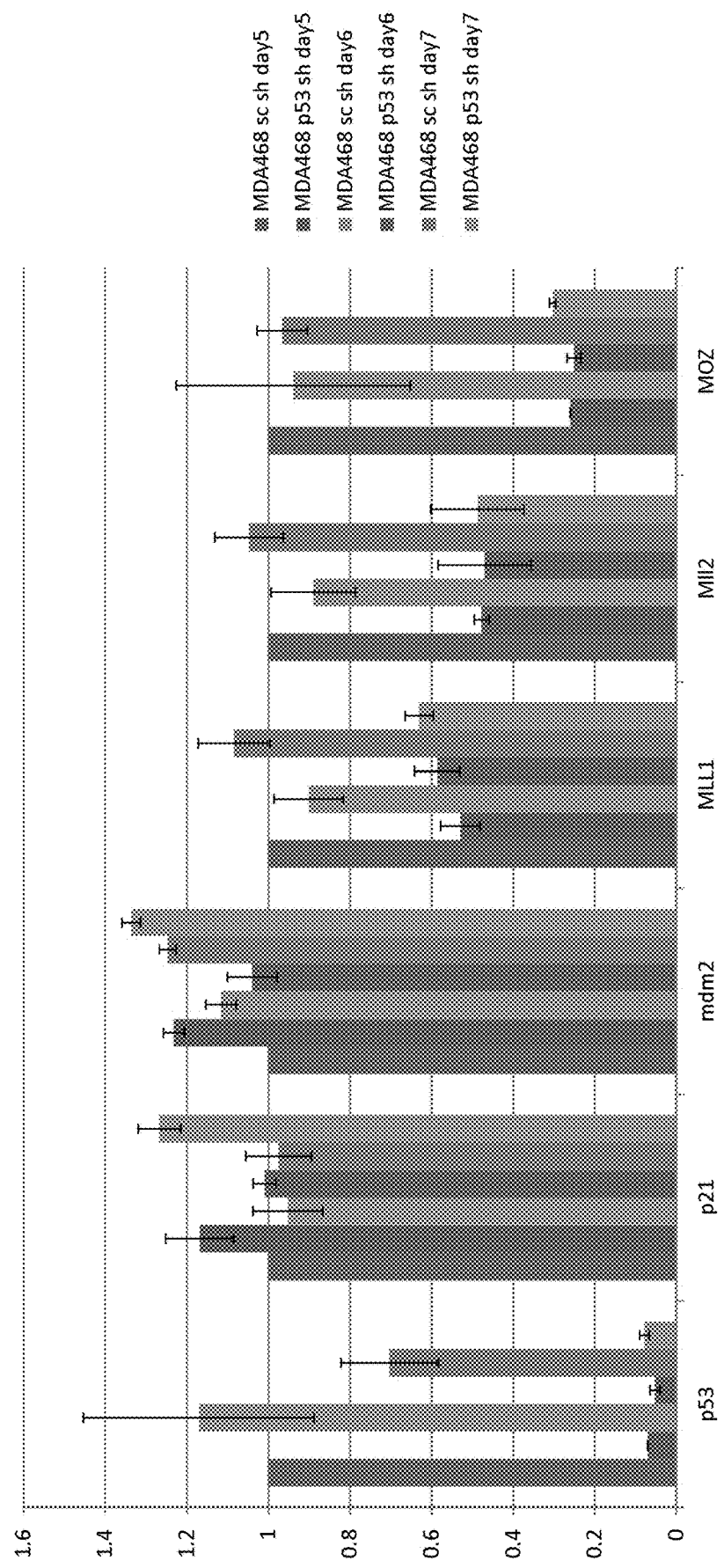
FIG. 3 depicts the results of experiments using knockdown of p53 GOF mutant in MD468 cells demonstrating that mutant p53 regulates expression of MLL1, MLL2, and MOZ genes.

Experiments were then conducted to evaluate the effects of knockdown of mutant p53. All knockdowns were achieved by lenti-viral infection of short hairpin RNA. shRNA (short hairpin interfering RNA)-mediated knockdown of mutant p53 expression demonstrates that the p53 GOF mutants regulate expression of MLL1, MLL2, and MOZ expression, but not p21 and MDM2 (canonical wild-type p53 targets) (FIG. 3). The bar graph depicts 3 different time points for measurement of gene expression and both a control (scrambled, sc sh) and a mutant p53 (p53 sh) knockdown.

Experiments were next conducted to evaluate the functional outcomes of the p53 GOF regulation of histone modification. FIG. 4A (left) depicts a Western blot analysis of the MDA468 cell line in response to control or p53 knockdown. It is shown that H3K9Ac decreases in response to knockdown of mutant p53, but no other histone modifications appear to be affected. Interestingly, H3K4me3 (the product of MLL1 activity) does not appear to be affected, suggesting that H3K4me3 is only locally affected by mutant p53 activity. These results are validated by demonstrating that H3K9ac drops in response to knockdown of mutant p53 expression, and this loss of H3K9ac is not affected by etoposide treatment (a wild-type p53 activating drug) (FIG. 4A; top-right). This suggests that the mutant p53 GOF activity is not regulated in a similar fashion to the wild-type protein. Similar results, demonstrating the loss of H3K9ac in response to p53 knockdown in in PANC1 cells (pancreatic cancer cell line with mutant GOF p53 (R273H)), was also obtained (FIG. 4A; bottom-right).

Figure 4B:
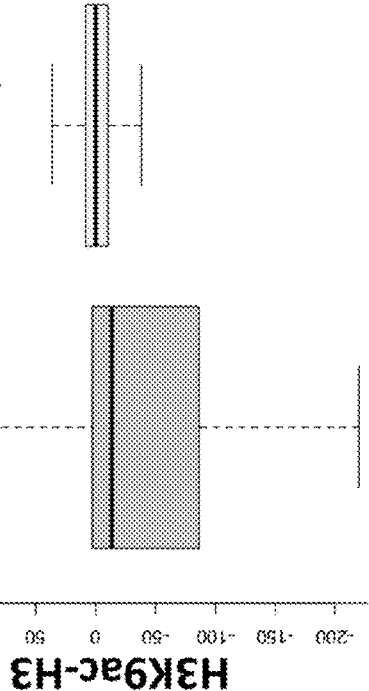
Figure 4B:
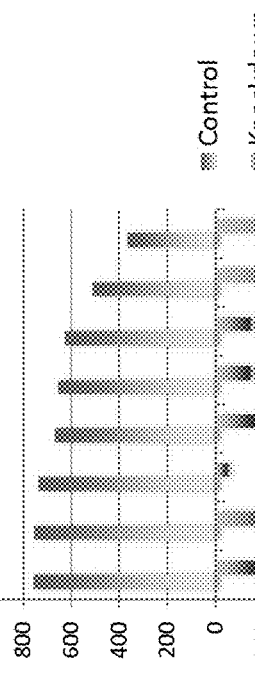
Figure 4B:
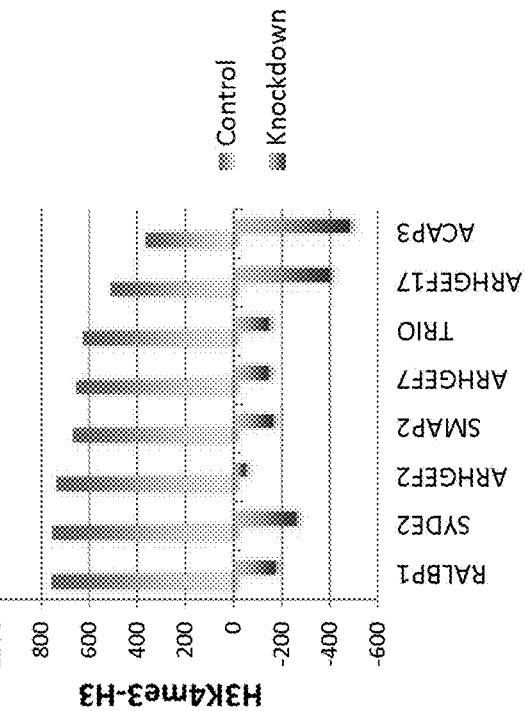
Figure 4B:
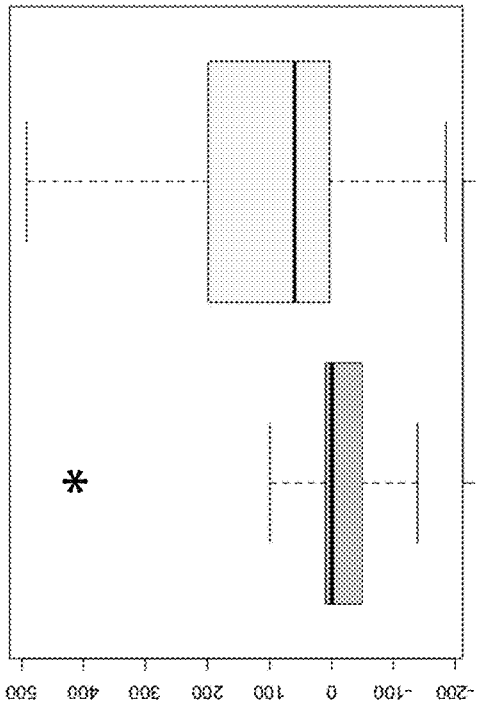
Figure 4B:
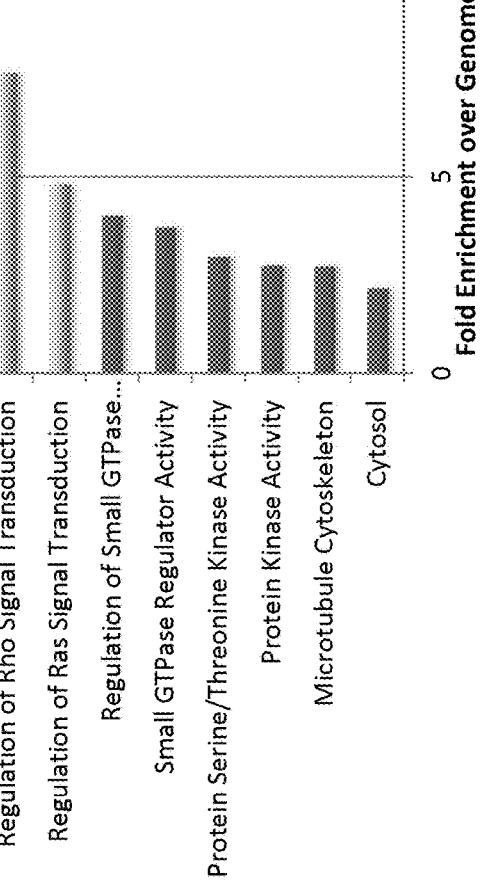

To determine the functional outcome of mutant p53 activity on genome-wide localization and abundance of H3K4me3 and H3K9ac, ChIPseq experiments were performed in MDA468 cells in control and mutant p53 knockdown. It was observed that H3K4me3 and H3K9ac abundance is dramatically decreased at genes in response to knockdown of mutant p53 compared to controls (FIG. 4B; top). Gene Ontology enrichment demonstrates that the RHO and RAS signaling pathways appear to be most affected by the loss of H3K4me3 in response to p53 GOF knockdown (FIG. 4B; bottom left). Rho and RAS signaling are intimately involved in tumorigenesis. The loss of H3K4me3 was observed in response to p53 GOF knockdown (FIG. 4B; bottom right).

Figure 4C:
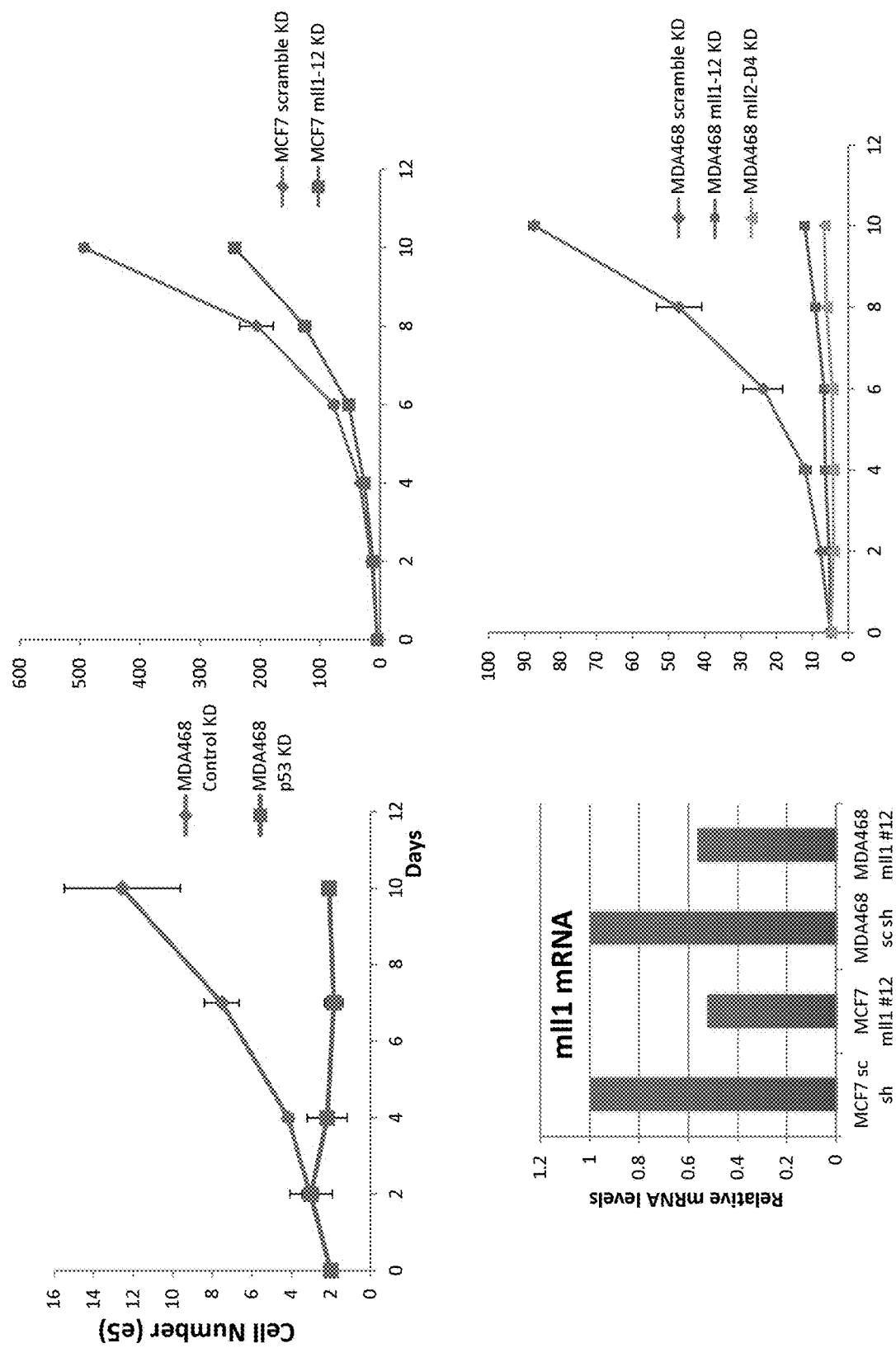

Further, experiments were conducted to evaluate the growth of cells with p53 GOF mutants in response to knockdown of p53, MLL1, or MLL2. The results demonstrate that MDA468 cell lines with mutant GOF p53 are sensitive to knockdown of p53 (FIG. 4C; top left). When mutant p53 expression is reduced by shRNA, MDA468 cells stop proliferating, while control knockdowns show no effect.

MLL1 or MLL2 knockdown in MDA468 (mutant p53) cells causes a dramatic cell proliferation defect. Note the extreme loss of proliferation in the mutant p53 cell line compared to wild-type (MCF7 cells) (FIG. 4C; Bottom right vs Top right). Analysis of MLL1 expression in response to MLL1 or control shRNA knockdowns demonstrates the efficacy of MLL1 knockdown in these experiments (FIG. 4C; bottom left).

Example 2

Prevalent p53 Gain-of-Function Mutants Co-Opt Epigenetic Pathways to Drive Cancer Growth TP53 is the most frequently mutated gene among all human cancers (Lawrence et al., 2014, Nature, 495-501). In most cases, mutant p53 consists of a single nucleotide missense mutation, leading to a single amino acid substitution (Brosh et al. 2009, Nat Rev Cancer, 9: 701-713; Freed-Pastor et al., 2012, Genes Dev, 26: 1268-1286). In addition to the loss of wild-type p53 tumor suppression, accumulating evidence suggests that these substituted forms have gained functions to promote cancer development (Brosh et al. 2009, Nat Rev Cancer, 9: 701-713; Freed-Pastor et al., 2012, Genes Dev, 26: 1268-1286; Muller et al., 2013, Nat Cell Biol: 15, 2-8). In order to better understand the mechanisms of mutant p53 "gain-of-function" (GOF), p53 chromatin immunoprecipitation was performed followed by genome-wide sequencing (ChIP-seq) in multiple human breast tumor derived cell lines with different p53 GOF substitutions. Strikingly, epigenetic pathways emerge as the most enriched genomic targets of these p53 GOF mutants. In particular, the results presented herein indicate that GOF p53 directly target genes encoding key epigenetic enzymes including KMT2A (MLL1), KMT2D (MLL2), and KAT6A (MOZ or MYST3). Genome-wide analyses of histone H3 Lysine 4 tri-methylation (H3K4me3; modification by MLL1) ChIP-seq and RNA sequencing (RNA-seq) in GOF p53 knock in mouse embryonic fibroblasts (MEFs) show specific increases over canonical MLL targets. Importantly, cancer cell growth is dramatically lowered by knockdown of the MLL epigenetic regulators, which phenocopies lowered growth caused by knockdown of GOF p53 mutant itself. Furthermore, pharmacological inhibitors targeting two protein subunits in the MLL histone methyl-transferase complex, that is, menin or WDR5, achieve similar effects in reducing cell growth, comparable to the MLL genetic knockdowns. The present study demonstrates a novel epigenetic mechanism underlying the progression of tumors with GOF p53, and indicates that oncogenic cells are "addicted" to these epigenetic alterations—the GOF p53 is unable to promote growth with reduction of these regulators. The results also suggest new possibilities for designing combinatorial epigenetic therapies for treating individual cancers driven by prevalent GOF p53 mutations.

The materials and methods employed in this example are now described.

Cell Culture

MDA-MB-175VII, HCC70, BT-549, and MDA-MB-468 cell lines were obtained from ATCC, and were cultured at 20% oxygen, in standard tissue culture medium (DMEM with 10% FBS and 1% penicillin/streptomycin) supplied with non-essential amino acids. Li-Fraumeni Syndrome cell lines MDAH087 and MDAH041 were obtained from Dr. Michael A. Tainsky (Wayne State University, Detroit, Mich.) as a kind gift, and were cultured at 3% oxygen, in standard tissue culture medium. AT-1 cells were isolated as previously described (Thiel et al., 2013, Haematologica, 98: 918-927), and cultured in IMDM supplemented with 15% stem cell FBS, 2 mM L-glutamine, 100 Units/mL penicillin, 100 µg/mL streptomycin, and 10 ng/mL IL-3. R172H knockin mice were generated by Dr. Tyler Jacks (Massachusetts Institute of Technology) (Olive et al., 2004, Cell 119, 847-860) and obtained from the NCI Mouse Repository. Primary MEFs from 13.5-day embryos were generated as previously described (Lee et al., 2010, Proc Natl Acad Sci USA, 107: 69-74), and culture in standard tissue culture medium at 3% oxygen condition.

Antibodies p53 mono-clonal antibody DO-1 was obtained from Calbiochem EMD; p53 poly-clonal antibody FL393 was obtained from Santa Cruz Biotechnology Inc. (sc-6243). Other antibodies used are: Flag (Sigma, M2), HA (Rockland, 600-401-384), histone H3 (abcam, ab1791), H3K4me1 (abcam, ab8895), H3K4me2 (Active Motif 39142), H3K4me3 (abcam, ab8580), H3K9ac (Active Motif, 39137), H3K14ac (Active Motif 39616), ETS2 (Santa Cruz Biotechnology Inc., sc-351), MLL1 (Bethyl Laboratories Inc., A300-086A), Menin (Bethyl Laboratories Inc., A300-105A), MOZ (Novus Biologicals, 21620002), mouse p53 for ChIP experiments (Santa Cruz Biotechnology Inc., sc-1312 (M-19)), mouse p53 for western blot experiments (Cell Signaling Technology, #2524).

Co-Immunoprecipitation

Flag tagged ETS2 protein was expressed in HEK293T cells, which was then subjected to immunoprecipitation with Flag antibody conjugated Dynabeads. Then after washes, HA tagged WT or GOF p53 (generated by in vitro translation method (Thermo #88881)) was added to co-immunoprecipitate with Flag-ETS2. Endogenous co-IP experiments were performed in buffer containing: 20 mM Tris, pH 8.0, 137 mM NaCl, 1 mM MgCl2, 1 mM CaCl2, 1% NP-40, 10% glycerol, plus complete protease and phosphatase inhibitor (without EDTA), plus 12.5 U/ml benzonase (Novagen, 70746).

ChIP-qPCR and ChIP-Seq

ChIP was performed as previously described (Shah et al., 2013, Genes Dev, 27, 1787-1799), with a few modifications. Following ChIP, DNA was quantified by qPCR using standard procedures on a 7900HT Fast-Real-Time PCR platform (ABI); or sequencing libraries were prepared using NEBNext Ultra library preparation procedure, and then sequenced on Illumina Hi-Seq platform at the Next-Generation Sequence Core at University of Pennsylvania, or on Illumina Next-Seq platform in the Epigenetics Program at the University of Pennsylvania.

Growth Curve Measurements 200,000 cells were seeded on 950 mm$^2$ surface area (one well of 6-well plate) on Day 0. Cell number was measured every two days with Countess Automated Cell Counter (Life Technologies) following its standard procedure, and then 200,000 cells were plated back for the next counting. For shRNA mediated knockdown experiments, cells were seeded seven days after the initial infection of shRNA-containing lentivirus, during which puromycin selection was completed and cells were already put back to normal growth medium. For small compound inhibitor treatment experiments, inhibitors were added on Day 0 as cells were seeded and refreshed every other day as cells were counted and plated back.

Colony-Formation Assay 2000 cells were seeded per well in 6-well plates. Three weeks later, colonies were stained with 0.1% crystal violet (for 15 minutes). The dye was released into 10% acetic acid and quantified by OD590.

Anchorage-Independent Growth Soft Agar Assay

The base layer of soft agar contains complete DMEM media (10% FBS and 1% penicillin/streptomycin) with 1% agar; the top layer of soft agar containing complete DMEM media with 0.7% agarose was mixed with 5000 cells and then plated on top of the base layer. Colonies were stained with 0.005% crystal violet (for 1 hour), and the number of visible colonies was counted.

Tumor Xenograft Assay

Cells were harvested after shRNA (MLL1 or non-targeting control) mediated knockdowns. 1.5 million cells were injected subcutaneously per mouse (NOD, scid, gamma, immune-deficient). After three weeks, tumor incidence was recorded and tumor size was measured by calipers. Tumor size was measured as two dimensions, and tumor volume was calculated as: $½ \times Length \times Width^2$ ChIP-Seq and RNA-Seq Analysis All human sequencing reads were aligned to human genome hg18 using Bowtie2 (Langmead and Salzberg, 2012, Nat Methods, 9: 357-359). For p53 ChIP-seq, significant regions of enrichment (peaks) were called using HOMER (Salk Institute). For area under the curve analysis, ChIP-seq tags from each cell line were counted at TSS proximal peaks (+/−200 bp around peak centers) of every other cell line (including itself) as indicated. Heat maps of p53 enrichment across a 5kb region (−/+2.5kb from peak center, bin=10) in MCF7, MDA-MB-175VII, MDA-MB-468, HCC70, BT-549 cell lines were generated using HOMER and visualized using JavaTreeView. Sequencing reads from mouse embryonic fibroblasts ChIP-seq experiments were aligned to the mouse reference genome mm9 using Bowtie2. Strand-specific mouse RNA-seq experiments were aligned to the mm9 reference genome and reference transcriptome. FPKM expression values were counted for each exon and merged into a single gene model using HOMER.

Motif Analysis

To determine associated sequence motifs for WT p53 or GOF p53 peaks, all TSS proximal peaks (filtered to remove peaks overlapping with satellite DNA) were pared down to the central 50 bp and used as input to MEME and the SeqPos utility in Cistrome (central 100 bp as required by SeqPos). MEME was instructed to search for the top 10 motifs appearing 0 or more times in each sequence, and SeqPos was run with default parameters.

Gene Ontology Analysis

GO terms associated with WT p53 or GOF p53 binding sites were determined in the following way. ChIP-seq TSS proximal peaks were associated with the nearest ENSEMBL transcript and processed using DAVID. The FDR was controlled at 1% and GO terms with fewer than 5 associated transcripts or a fold-enrichment over the genomic background under 5-fold were discarded.

ETS ChIP-Seq Datasets

Called peaks for publicly available ETS ChIP-seq data were lifted over (for A549 cells, GM12878 cells, and K562 cells) from assembly hg19 of the human genome to hg18 at a minimum remap ratio of 0.95. Peak sets were merged for multiple replicates from the same cell line. Overlap with p53 peaks was inferred if even a signal base-pair of the p53 peak and the ETS peak was in common.

Molecular Docking

The crystal structure of menin complexed with MLL was used as the basis for molecular docking (Huang et al., 2012, Nature, 482: 542-546). The atomic coordinates for the MLL peptide were extracted to permit small molecule docking to this structural pocket on the surface of menin. The site for molecular docking was selected using DMS (UCSF) to generate a molecular surface, and SPHGEN_CPP to define spheres that represent sites of potential ligand atoms. Spheres within 6 Å of MLL peptide residues Phe9 Pro10 were selected as the site for molecular docking. Grid-based scoring implemented in DOCK6.6 was used. This was accomplished using a scoring grid extending 5 Å in 3 dimensions from the selected spheres. DOCK6.6 was used to screen drug-like compounds (that follow the Lipinsky rules of drug likeness) in a repository at the National Cancer Institute Developmental Therapeutics Program (NCI plated 2007, 139,735 compounds). Each compound was docked in 1,000 orientations and scored for hydrophobic (van der Waals score) and electrostatic interactions (electrostatic score) at the UF High Performance Computing Center by parallel processing using 8 cpu. Compounds were ranked based on overall Energy Score (van der Waals score+ electrostatic score). The top 40 scoring compounds (out of 103, 539 drug-like small molecules screened by molecular docking) were obtained from the NCI DTP to measure effects on menin functional activity.

Menin Protein Purification

The His-SUMO-Menin-Δ460-519 construct was obtained from Dr. Ming Lei at the University of Michigan and expressed in Rosetta (DE3-pLysS) E. coli. Following a 16 h induction with 0.1 mM IPTG at 20° C., cells were pelleted by centrifugation and resuspended in lysis buffer (50 mM Tris-HCl pH8.0; 50 mM NaH2PO4; 400 mM NaCl; 10% glycerol, 2 mM β-mercaptoethanol, 10 μg/mL lysozyme, 1 mM PMSF, 1× Sigma bacterial protease inhibitor cocktail). Bacteria were lysed by sonication and debris removed by ultracentrifugation. The supernatant was incubated with Ni-NTA beads (Qiagen) for 2 h at 4° C. prior to elution with 200 mM imidazole. Eluted protein was concentrated using an Ultra YM-10 Centriprep spin filter column (Millipore), and further purified by gel-filtration chromatography on a HiLoad Superdex200 column (GE Healthcare), aliquoted, and stored at −80° C.

MLL Peptide Synthesis

MLL peptides containing the wild type or mutant motif which binds menin were synthesized, dissolved in DMSO, and stored at −80° C. Sequences for each peptide are as follows:

```
                                          (SEQ ID NO: 1)
FITC-MLL: (fluorescein)-RWRFPARPGTGRRG-(amide)

(SEQ ID NO: 2)
WT-MLL:   (biotin)-RWRFPARPGTGRRG-(amide)

(SEQ ID NO: 3)
Mut-MLL:  (biotin)-MAHSCAWAFPGSGSCAWAFP-(amide)
```

Synthesis of ISC-30

ISC-30 was synthesized with Chemzon Scientific Inc., QC, Canada. Quality control was performed by HPLC coupled mass spectrometry with the purity of the compound greater than 99.4%.

Fluorescence Polarization Competition Assay

ISC30 was titrated into the wells of a 384-well plate containing fluorescence polarization buffer (40 mM HEPES pH 7.9, 150 mM NaCl, 0.01% Triton-X-100, 10 mM 2-mercaptoethanol), FITC-MLL peptide (1.5 nM), and His-SUMO-Menin-Δ460-519 (5 nM). In control wells, either 1 μM WT-MLL or 1 μM Mut-MLL peptide was added instead of ISC30 to normalize percent inhibition relative to these positive and negative controls, respectively. Immediately following the addition of ISC30, plates were measured for changes in fluorescence polarization compared to blank wells (containing only buffer) on an Envision Multilabel Reader (Perkin Elmer) with 480 nm excitation and 535 nm emission wavelengths. Blanked millipolarization (mP) values were normalized on a percent scale where 0% is no inhibition (based on Mut-MLLpeptide mP values) and 100% is high inhibition (based on WT-MLL peptide mP values). Inhibition by ISC30 was fit to a non-linear regression curve to calculate a normalized IC50.

OICR-9429

OCIR-9429 was developed using structure-guided medicinal chemistry and peptide displacement assays starting from 'Compound 3' previously reported in Senisterra et al (Senisterra et al., 2013, The Biochemical journal, 449: 151-159), as part of the Chemical Probe Program of the Structural Genomics Consortium. OICR-9429 is highly specific for WDR5 and was shown to have >100-fold selectivity over 300 other chromatin "reader" domains, methyl-transferases, and other non-epigenetic targets. The details of its structure, discovery and characterization can be found in Grebien et al., (Grebien et al., 2015, Nature Chemical Biology, in revision).

The results of the experiments are now described

Prevalent p53 GOF Mutants Induce Expression of Epigenetic Regulators Resulting in Histone Modifications and Tumor Growth Most mutant forms of p53 are caused by single amino acid substitutions mapping to the p53 DNA binding domain. These mutations result in expression of full-length p53 protein, but loss of normal, wild-type (WT) tumor suppressive function (Brosh et al. 2009, Nat Rev Cancer, 9: 701-

713; Freed-Pastor et al., 2012, Genes Dev, 26: 1268-1286; Muller et al., 2013, Nat Cell Biol: 15, 2-8). The high prevalence of missense mutations, particularly certain "hotspot" point mutations, suggests a selective advantage during cancer progression. Indeed, these substitution mutations gain neomorphic oncogenic functions, including altered cancer spectrum (Lang et al., 2004, Cell, 119: 861-872; Olive et al., 2004, Cell, 119: 847-860), deregulated metabolic pathways (Freed-Pastor et al., 2012, Cell, 148: 244-258; Zhang et al., 2013, Nat Commun, 4: 2935), increased metastasis ability (Subramanian et al., 2014, Oncogene, doi:10.1038/onc.2014.46; Weissmueller et al., 2014, Cell, 157: 382-394) and enhanced chemotherapy resistance (Do et al., 2012, Genes Dev, 26: 830-845). Evidence from recent studies points to one potential mechanism of GOF p53, functioning through physical association with other transcription factors, and driving gene transcription in novel oncogenic pathways, such as the mevalonate pathway (Freed-Pastor et al., 2012, Cell, 148: 244-258) and etoposide resistance pathway (Do et al., 2012, Genes Dev, 26: 830-845). A transcription mechanism is further supported by the importance of retaining an intact transactivation domain for oncogenic GOF p53 function (Freed-Pastor et al., 2012, Cell, 148: 244-258; Scian et al., 2004, Cancer Res, 64: 7447-7454). Nonetheless, how GOF p53 contributes to massive changes of the cancer genome and transcriptome remains to be elucidated (Scian et al., 2004, Cancer Res, 64: 7447-7454; Garritano et al., 2013, Oncogenesis, 2: e54). Altered epigenetic pathways have been implicated in various aspects of cancer (Dawson et al; 2012, Cell, 150: 12-27; Tam et al., 2013, Nat Med, 19: 143-1449), which might be reasonable mechanisms, given their regulation of genome-wide transcription programs (Kouzarides, 2007, Cell, 128: 693-705; Li et al., 2007, Cell, 128: 707-719). However, to date there has not been evidence of direct crosstalk between GOF p53 and epigenetic regulation.

Figures 6A, 6B, 6C:
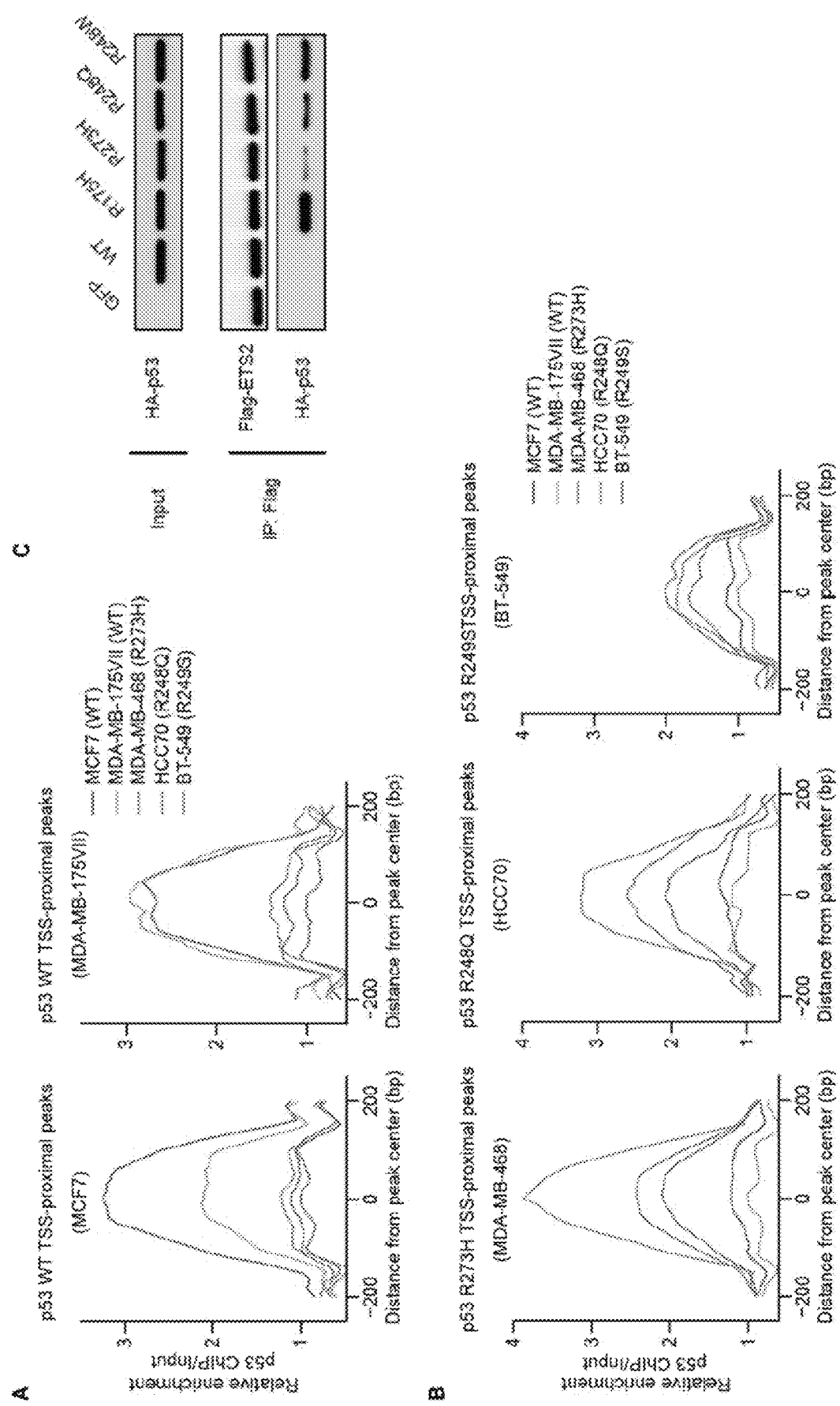
FIG. 6A through FIG. 6E, depicts the results of experiments demonstrating that distinct GOF p53 mutants showed similar binding pattern over the genome, but were dissimilar from that of WT p53.
Figure 11A:
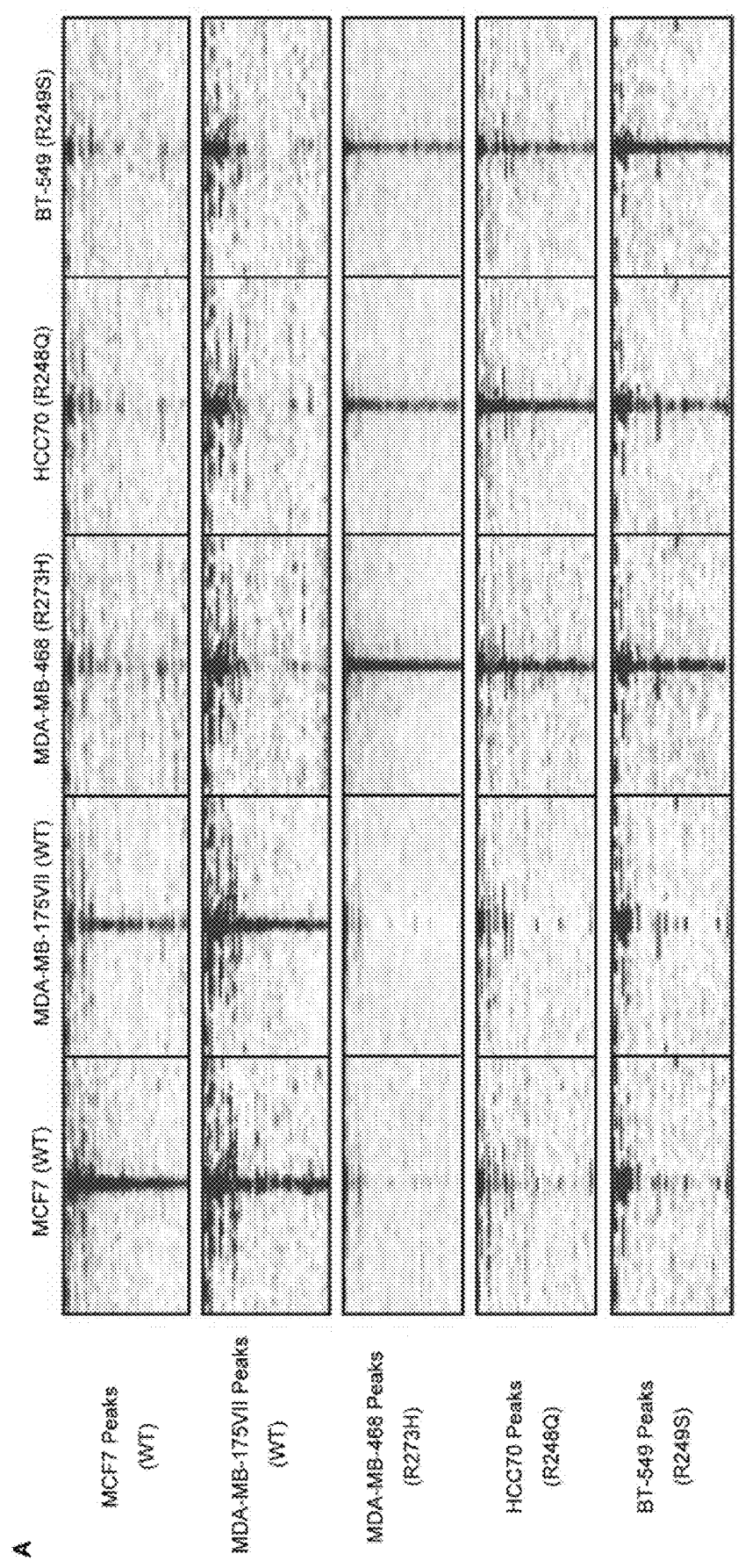
FIG. 11A through FIG. 11M, depicts the results of example experiments.
Figures 11B, 11C, 11D, 11E, 11F, 11G:
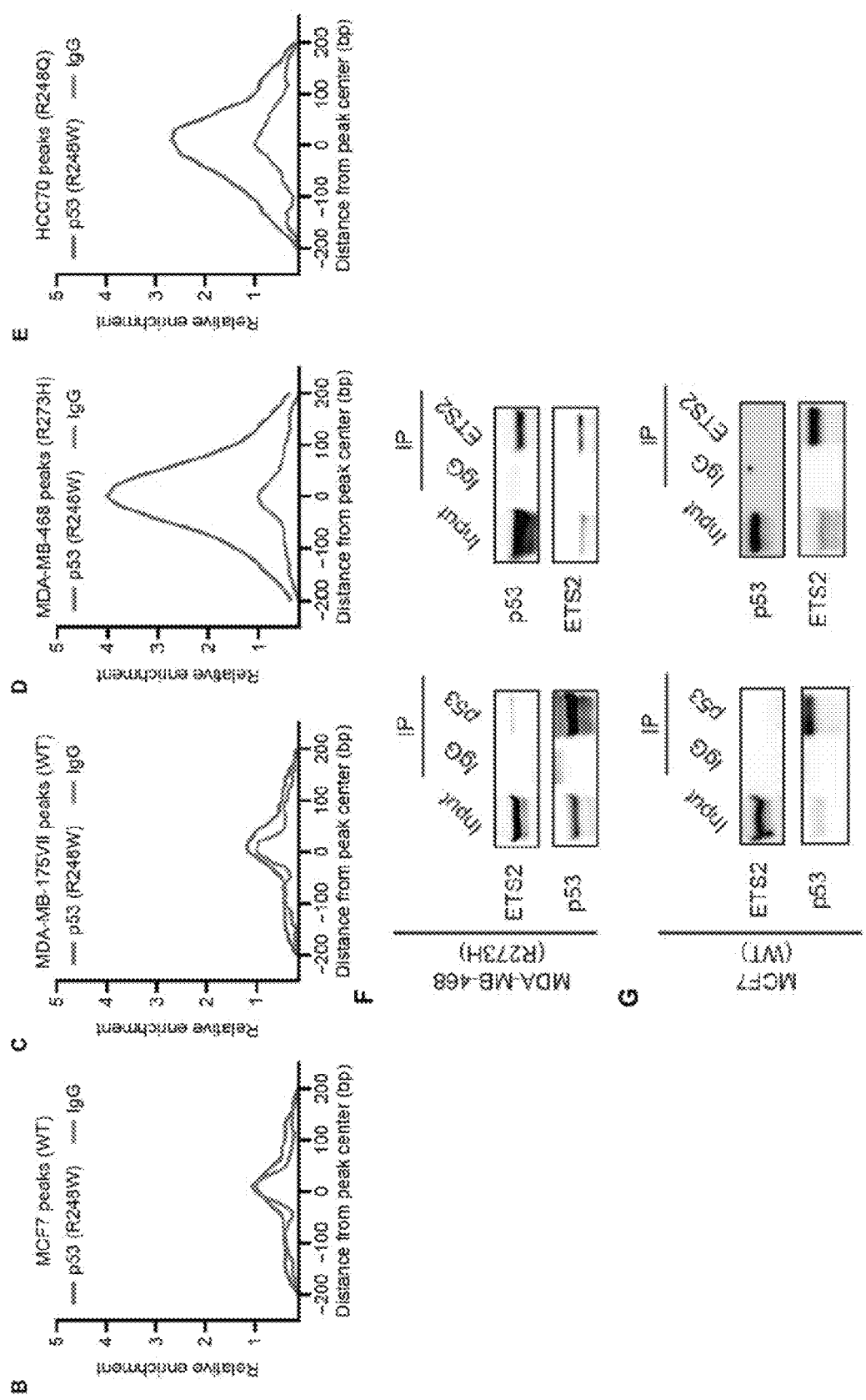

In order to investigate shared pathways and unique pathways among various GOF p53 substitution mutations, ChIP-seq was carried out to determine genome-wide binding locations of p53 in a panel of breast cancer cell lines— MCF7 (p53 WT), MDAMB-175VII (p53 WT), HCC70 (p53 R248Q), BT-549 (p53 R249S) and MDA-MB-468 (p53 R273H). It was found that the binding of p53 to gene-proximal regions (less than 10kb) of transcription start sites (TSS) in the two cell lines with WT p53 strongly resembled each other. However, these common peaks in the WT p53 cell lines were highly dissimilar from the peaks in any of the GOF p53 mutants (FIG. 6A and FIG. 11A, top two rows). Strikingly, the p53 binding patterns in the three GOF p53 cell lines were similar among themselves at TSS proximal regions (FIG. 6B and FIG. 11A, bottom three rows). In addition, published p53 R248W ChIP-seq data from Li-Fraumeni Syndrome (LFS) MDAH087 cells (Do et al., 2012, Genes Dev, 26: 830-845) was re-aligned, and again, TSS proximal peaks of LFS p53 R248W mutant resembled those of breast cancer cell p53 R273H and p53 R248Q (FIG. 11D and FIG. 11E), but were dissimilar from the WT p53 peaks (FIG. 11B and FIG. 11C).

Figures 11H, 11I, 11J, 11K, 11L, 11M:
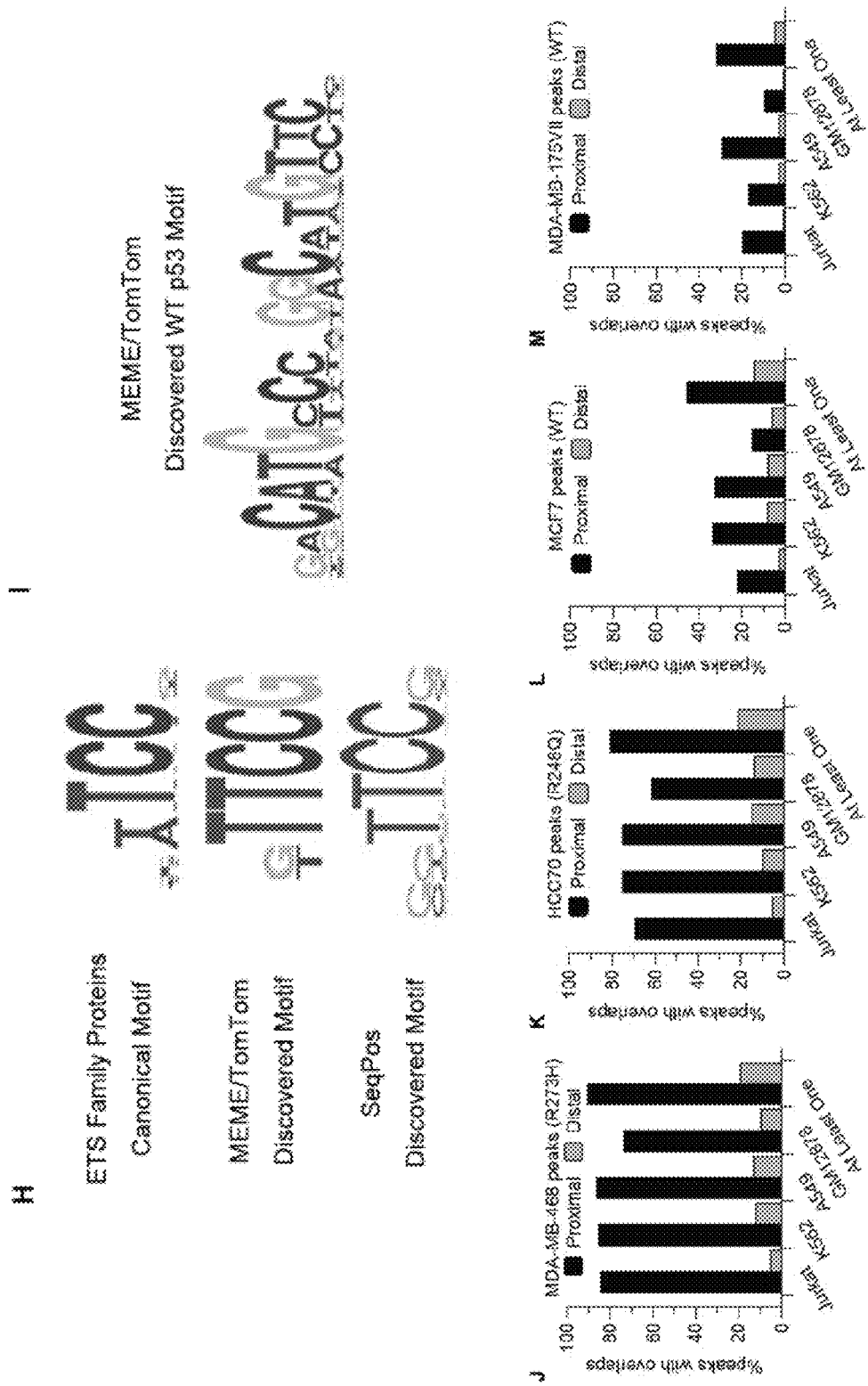

Motif analysis was performed for all TSS proximal peaks of the p53 R273H mutant. Two independent algorithms predict the E26 Transformation-Specific (ETS) motif as the most enriched (FIG. 11H), and notably, the consensus sequence of ETS is distinct from the WT p53 motif (FIG. 11I). Consistent with the motif prediction, one ETS family member, ETS2, has been shown to interact with mutant p53 10. It was confirmed that ETS2 indeed interacts with various GOF p53 mutants, but interacts to a much lesser extent with WT p53 (FIG. 6C), as previously noted (Do et al., 2012, Genes Dev, 26: 830-845). Co-immunoprecipitation (co-IP) was also performed at endogenous levels of the proteins, and it was demonstrated that ETS2 interacts with GOF mutant p53 (FIG. 11F), but not with WT p53 (FIG. 11G). GOF p53 peaks was compared with published ETS peaks (Bernstein et al., 2012, Nature, 489: 57-74; Gertz et al., 2013, Mol Cell, 52: 25-36) and it was found that more than 80% of the discovered GOF p53 TSS proximal peaks overlap with known ETS peaks (FIG. 11J and FIG. 11K), whereas the percentage of overlap between p53 WT peaks and ETS peaks is much lower (FIG. 11L and FIG. 11M). Thus, as previously seen (Do et al., 2012, Genes Dev, 26: 830-845), it is demonstrated herein that p53 GOF genome-wide binding is in association with ETS binding motifs and, while not wishing to be bound by any particular theory, likely via direct interaction with ETS proteins.

Figure 6D:
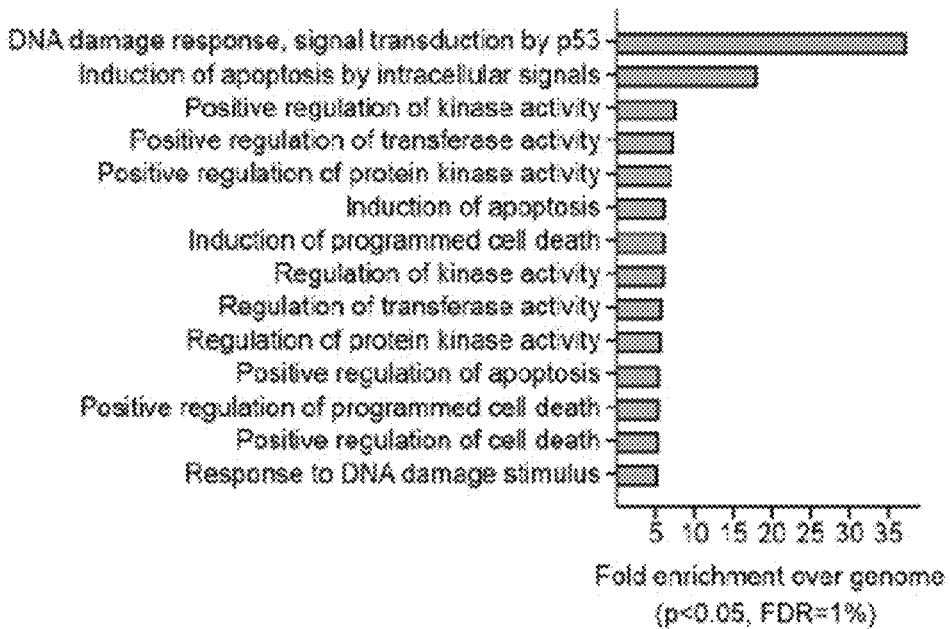
Figure 6E:
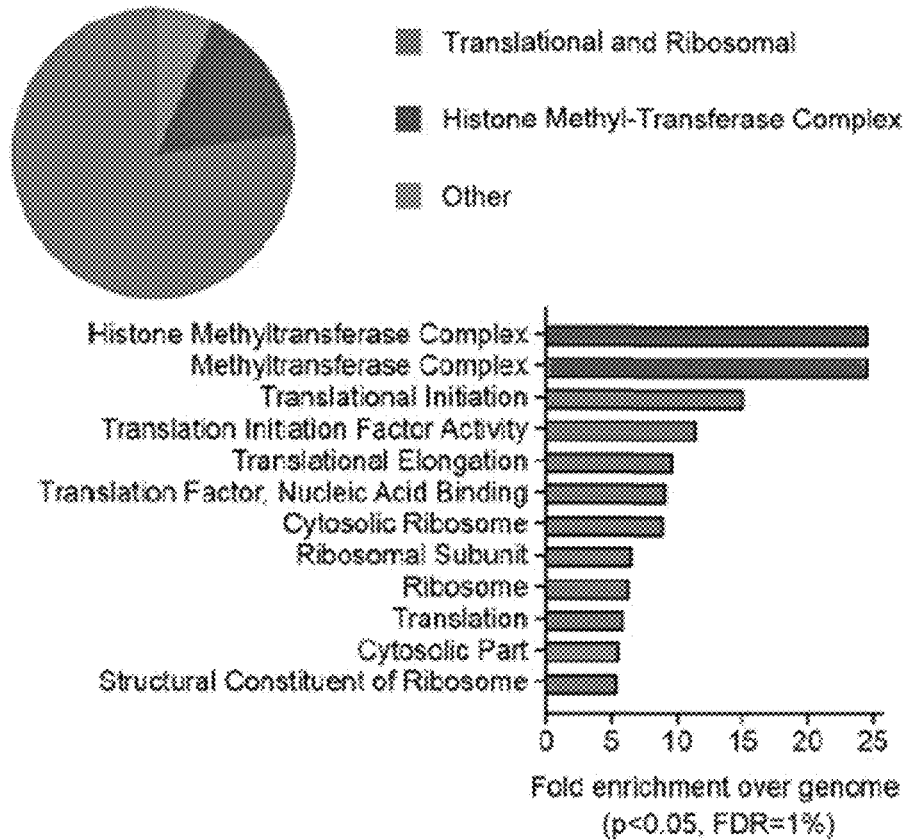
Figures 7A, 7B, 7C, 7D, 7E, 7F, 7G:
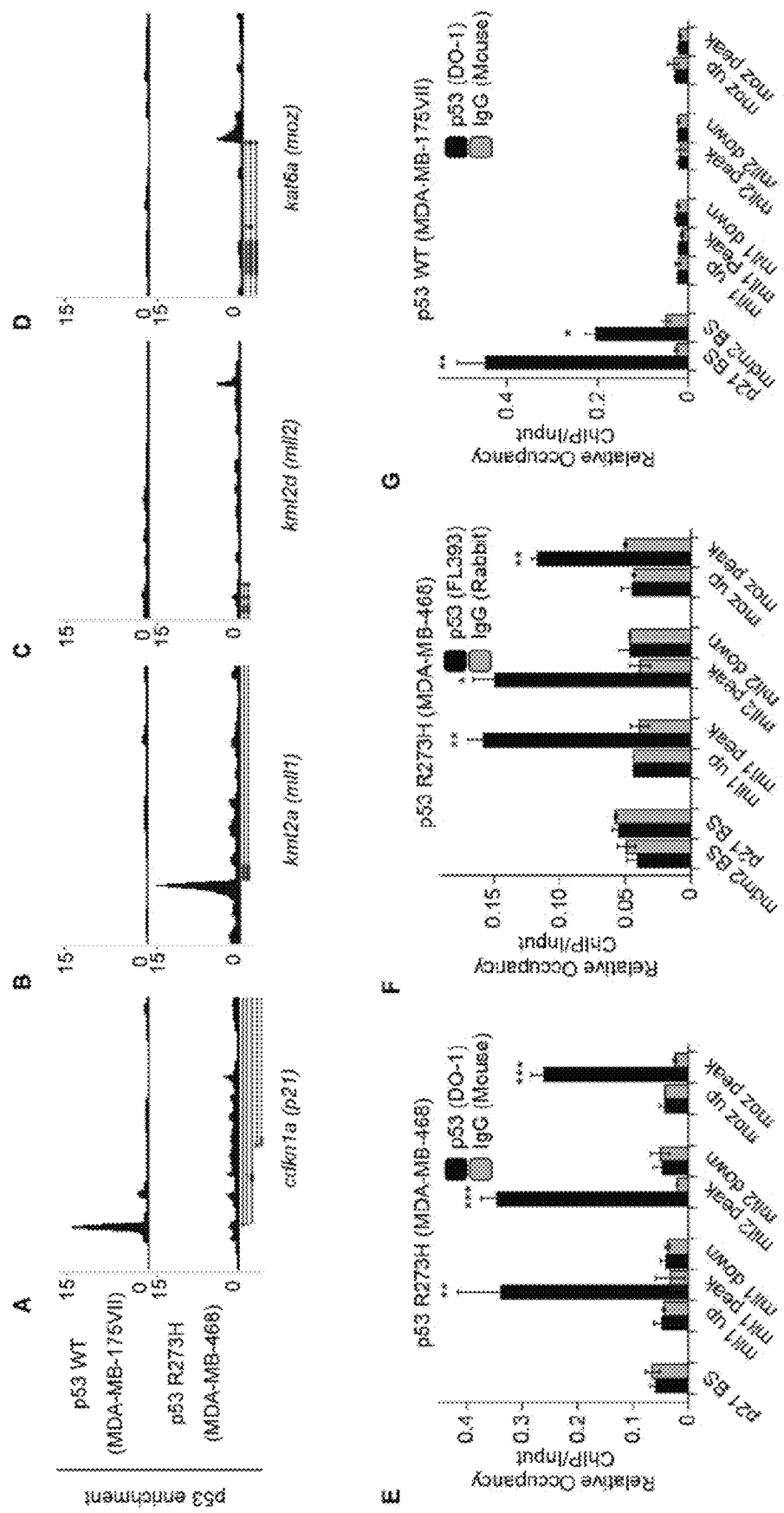
FIG. 7A through FIG. 7L, depicts the results of experiments demonstrating that GOF p53 bound to a group of epigenetic regulators. Track views showing p53 occupancy in MDA-MB-175VII and MDA-MB-468 cells at promoter regions of (FIG. 7A) p21, (FIG. 7B) mll1, (FIG. 7C) mll2, and (FIG. 7D) moz.
Figures 12A, 12B, 12C, 12D, 12E, 12F, 12G:
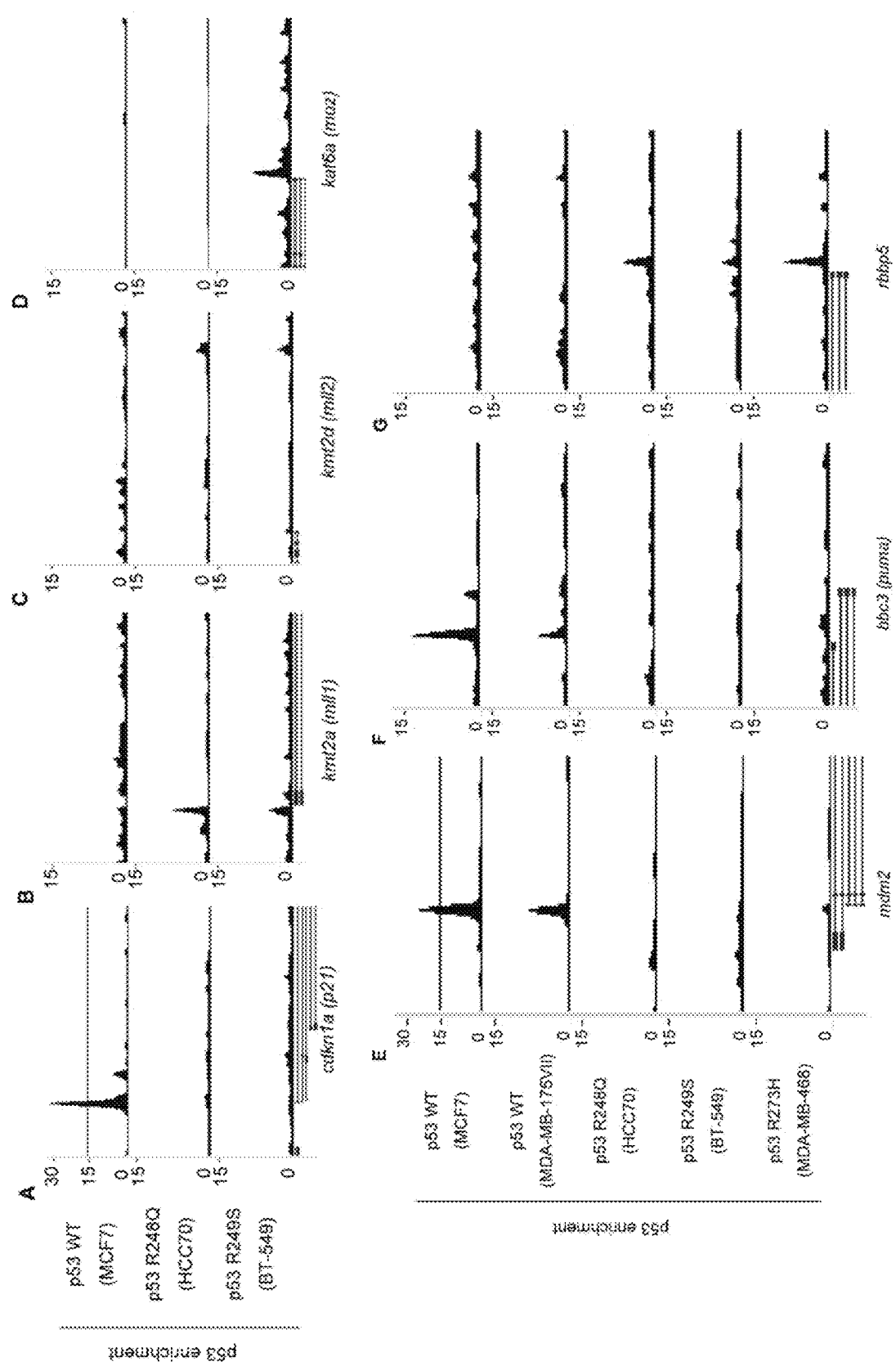
FIG. 12A through FIG. 12M, depicts the results of experiments. Track views showing p53 occupancy in MCF7, HCC70 and BT-549 cells, at promoter regions of (FIG. 12A) p21, (FIG. 12B) mll1 (FIG. 12C) mll2, and (FIG. 12D) moz. Track views showing p53 occupancy in MCF7, MDA-MB-175VII, HCC70, BT-549 and MDA-MB-468 cells, at promoter regions of (FIG. 12E) mdm2, (FIG. 12F) puma, and (FIG. 12G) rbbp5.
Figures 12H, 12I, 12J, 12K, 12L, 12M:
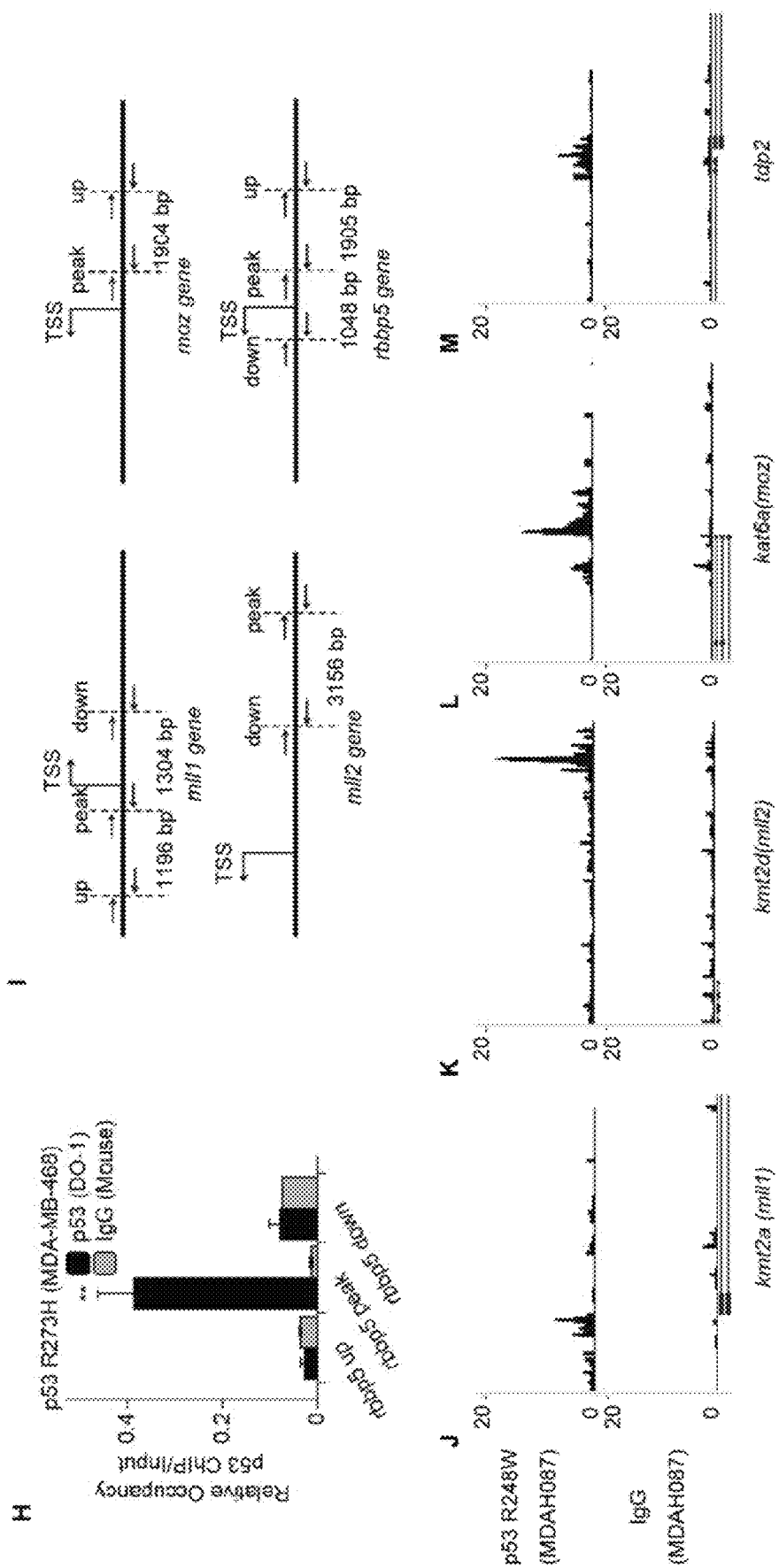

To determine specific functional categories among genes bound by GOF p53, Gene Ontology (GO) analysis was performed on all TSS proximal peaks. As expected, DNA damage response and apoptosis pathways were most enriched in WT p53 targets (FIG. 6D). In contrast, p53 R273H bound to genes driving translation, ribosomal RNA synthesis, and ribosomal protein genes (FIG. 6E), which was reasonable given the rapid growth rate of these cells compared to non-oncogenic cells. It was observed that GO categories enriched by GOF p53 binding are not enriched by WT p53. Furthermore, it was particularly intriguing that GOF p53 bound to a group of genes functionally related to histone methylation (FIG. 6E). Indeed, the binding was seen in track views of kmt2a (mll1) and kmt2d (mll2), genes encoding two histone H3 Lysine 4 methyl-transferases (FIG. 7B and FIG. 7C). The other two GOF p53 mutants that were examined, as well as the published p53 R248W ChIP-seq data from LFS MDAH087 cell, all showed similar binding at kmt2a (mll) and kmt2d (mll2) (FIGS. S2B, S2C, S2J and S2K). Track views also confirmed binding of GOF p53 to a gene encoding a common subunit of the COMPASS (complex proteins associated with Set1) histone methyl-transferase complexes, rbbp5 (FIG. 12G). In contrast, WT p53 did not appear to bind any of these GOF p53 targets, although as expected, WT p53 bound promoter regions of its canonical target genes, including cdkn1a (p21) (FIG. 7A and FIG. 12A), mdm2 and bbc3 (puma) (FIG. 12E and FIG. 12F). a large set of 600 epigenetic regulators was then analyzed and an additional group of epigenetic regulatory genes that showed GOF p53 peak enrichment was found. Among these was kat6a (moz), a histone acetyl-transferase, and track views confirmed the presence of GOF p53 but not WT p53 (FIG. 7D, FIG. 12D and FIG. 12L). Thus, this analysis points to DNA binding of GOF p53 to a cluster of genes encoding epigenetic regulators.

Figures 7H, 7I, 7J, 7K, 7L:
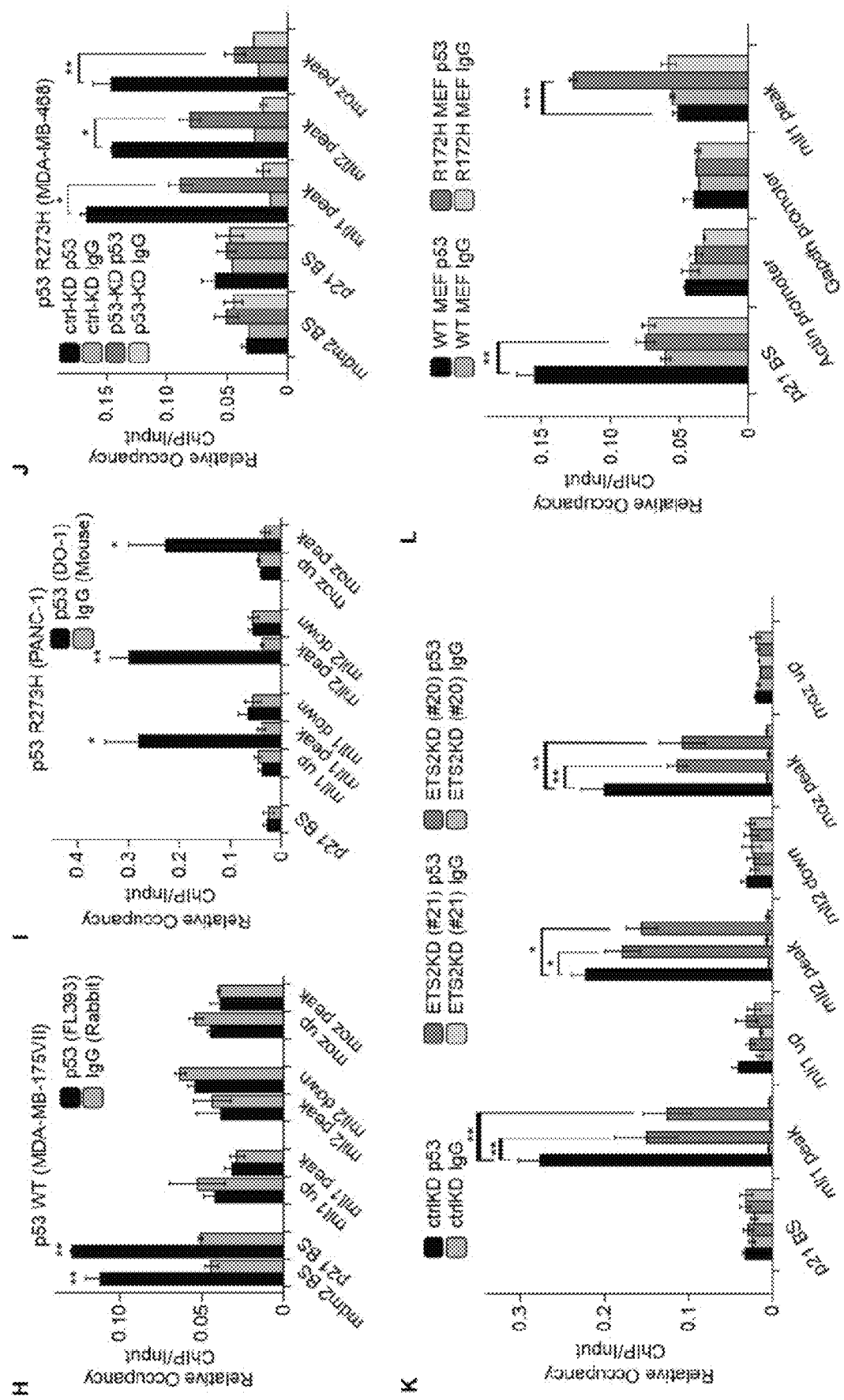

Using ChIP-quantitative PCR (ChIP-qPCR), the binding of GOF p53 R273H to the ChIP-seq peak regions near mll1, mll2, rbbp5 and moz was validated, whereas no binding was detected in regions nearby, that is, approximately 1kb upstream or downstream of the peaks (FIG. 7E, FIG. 12H and FIG. 12I). In addition, the ChIP-qPCR results were verified with a second p53, polyclonal antibody, FL393 (FIG. 7F), similar to the binding seen with the p53 monoclonal antibody DO-1 (compare FIG. 7E). Notably, in parallel experiments, WT p53 showed binding to the p21 and mdm2 canonical binding sites of p53, but not to any of the GOF p53 targets (FIG. 7G and FIG. 7H). An unrelated pancreatic cancer cell line, PANC-1, bearing the same p53 R273H substitution mutation was also examined, and a similar binding pattern to mll1, mll2 and moz, but not to p21, was observed (FIG. 7I), suggesting that the binding of GOF p53 to genes encoding these epigenetic regulators may be a general phenomenon in various cancer types. It was also found that the ChIP-qPCR signal of GOF p53 R273H was attenuated in shRNA-mediated p53 knockdown condition compared with scrambled non-targeting shRNA knockdown (FIG. 7J). To investigate the importance of ETS2 to the binding of GOF p53, ets2 RNA was knocked down by shRNA, leading to decreased binding of GOF p53 over the mll1 and moz peak regions, and to a lesser extent, over the mll2 peak region (FIG. 7K). To test the association of GOF p53 near mll1 in a non-tumor background, mice with homozygous knock-in GOF p53 (R172H, equivalent to human R175H) (Lee et al., 2010, Proc Natl Acad Sci USA, 107: 69-74) were generated, and ChIP-qPCR in primary MEFs bearing GOF p53 or WT p53 was performed. Consistent with the human results, mouse GOF p53 showed significant enrichment over the mll1 region, when compared with WT p53 or IgG controls (FIG. 7L). In clear contrast, WT p53 showed expected binding over its canonical target gene p21 in MEFs (FIG. 7L).

Figures 8A, 8B, 8C, 8D, 8E, 8F, 8G:
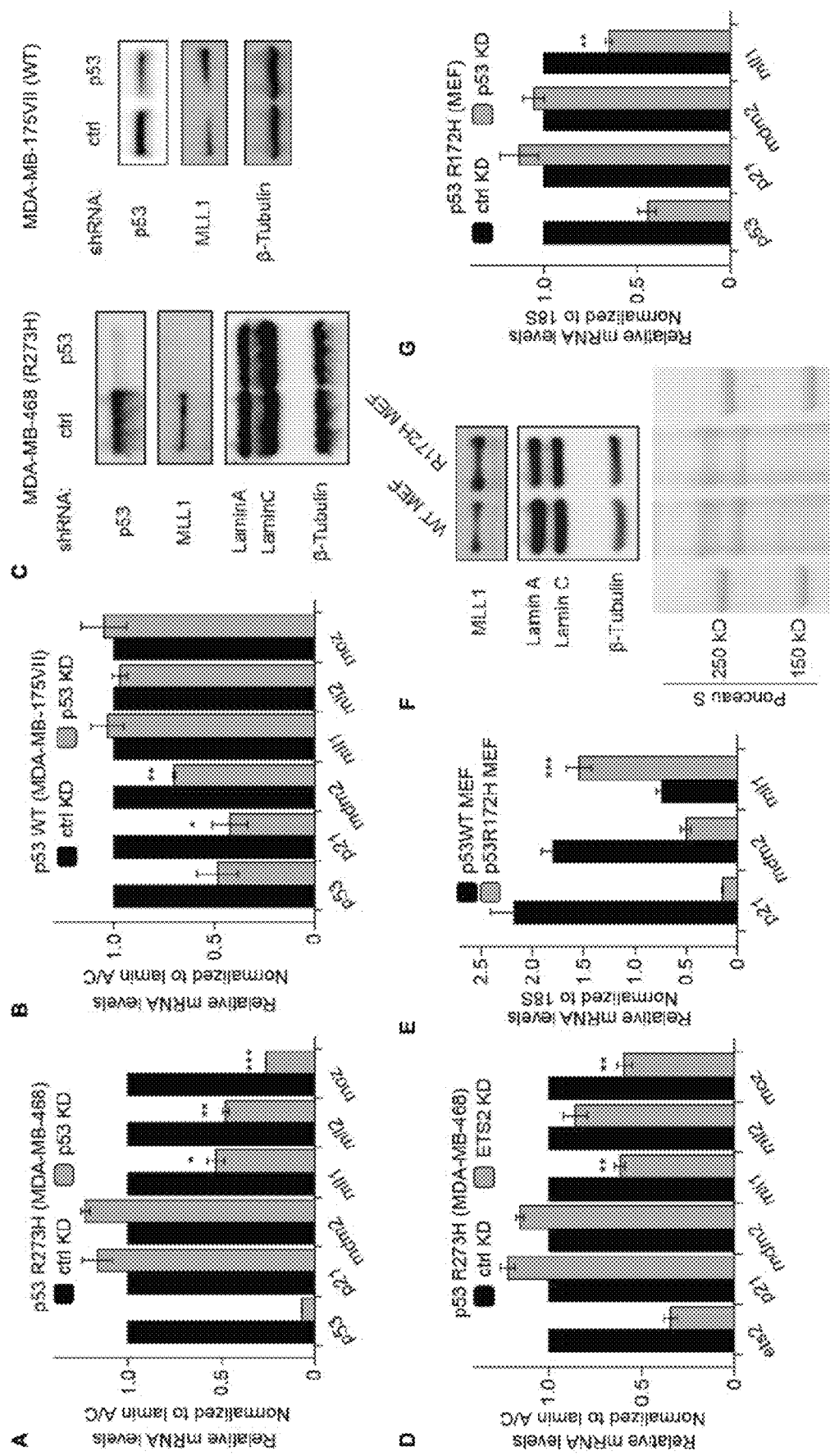
FIG. 8A through FIG. 8M, depicts the results of experiments demonstrating that GOF p53 regulates expression of MLL1, MLL2 and MOZ, and thereby histone post-translational modifications.
Figures 13A, 13B, 13C, 13D, 13E, 13F, 13G, 13H:
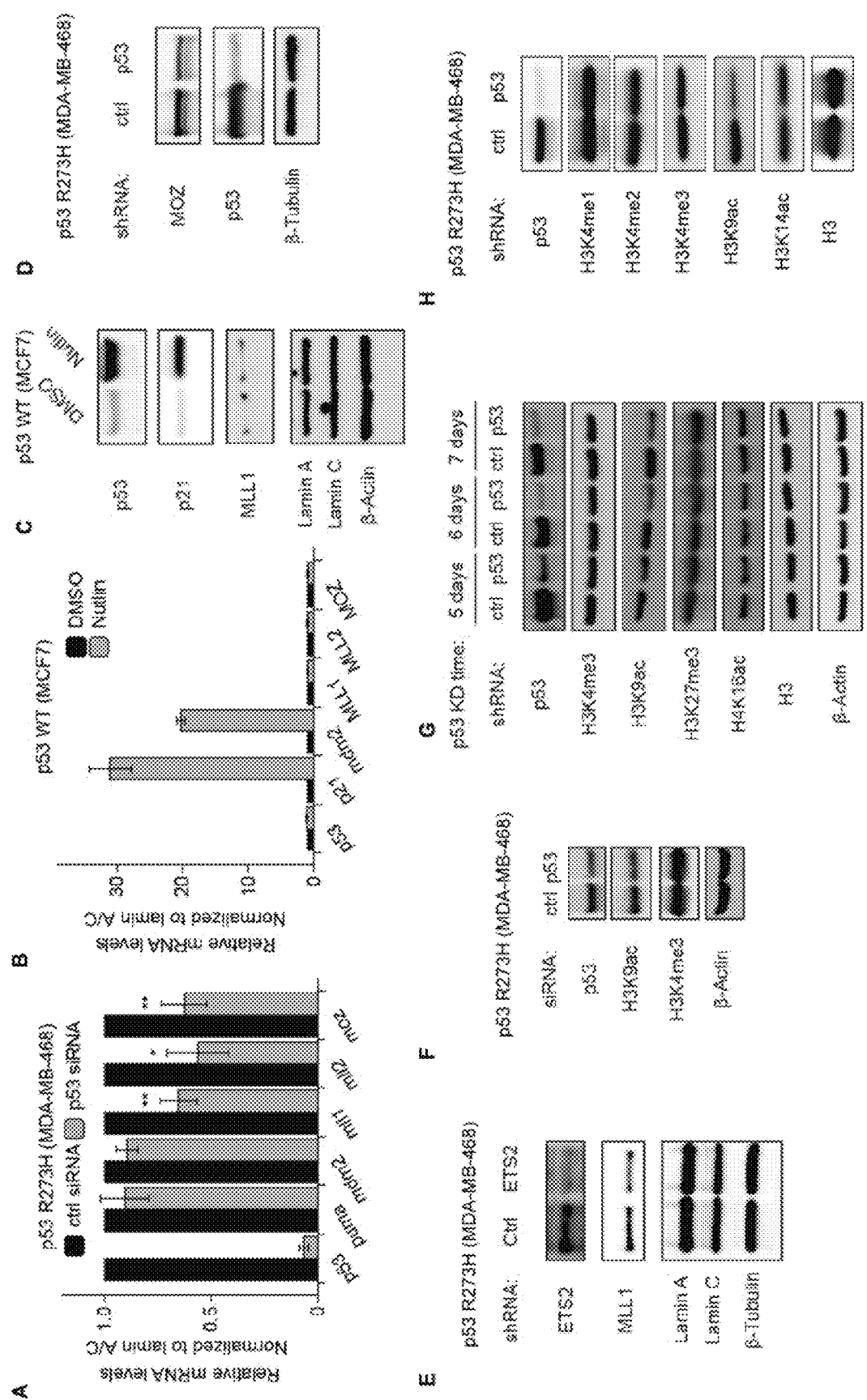
FIG. 13A through FIG. 13M, depicts the results of experiments.

To examine whether GOF p53 is required to drive expression of the epigenetic regulators, expression of p53 was reduced by either siRNA or shRNA knockdown approaches. It was found that the mRNA levels of mll1, mll2 and moz were also decreased when GOF p53 was reduced (FIG. 8A and FIG. 13A). No change in mll1, mll2, and moz was detected when WT p53 level was reduced, whereas expression levels of p21 and mdm2 were decreased as expected (FIG. 8B). As a control, mll1 was not upregulated via Nutlin-mediated stabilization and elevation of WT p53 levels (FIG. 13B and FIG. 13C), showing that simply increasing p53 protein levels does not recapitulate activation of the epigenetic regulators. In addition, MLL1 protein levels were decreased in the GOF p53 knockdown (FIG. 8C, left), but not by WT p53 knockdown (FIG. 8C, right), as was also observed for reduction of MOZ protein level upon GOF p53 knockdown (FIG. 13D). Furthermore, when ets2 level was knocked down, decreased expression of mll1 and moz, and to a lesser extent, mll2 was observed (FIG. 8D and FIG. 13E), which is in accordance with the ChIP-qPCR result (FIG. 7K).

Figures 13I, 13J, 13K, 13L, 13M:
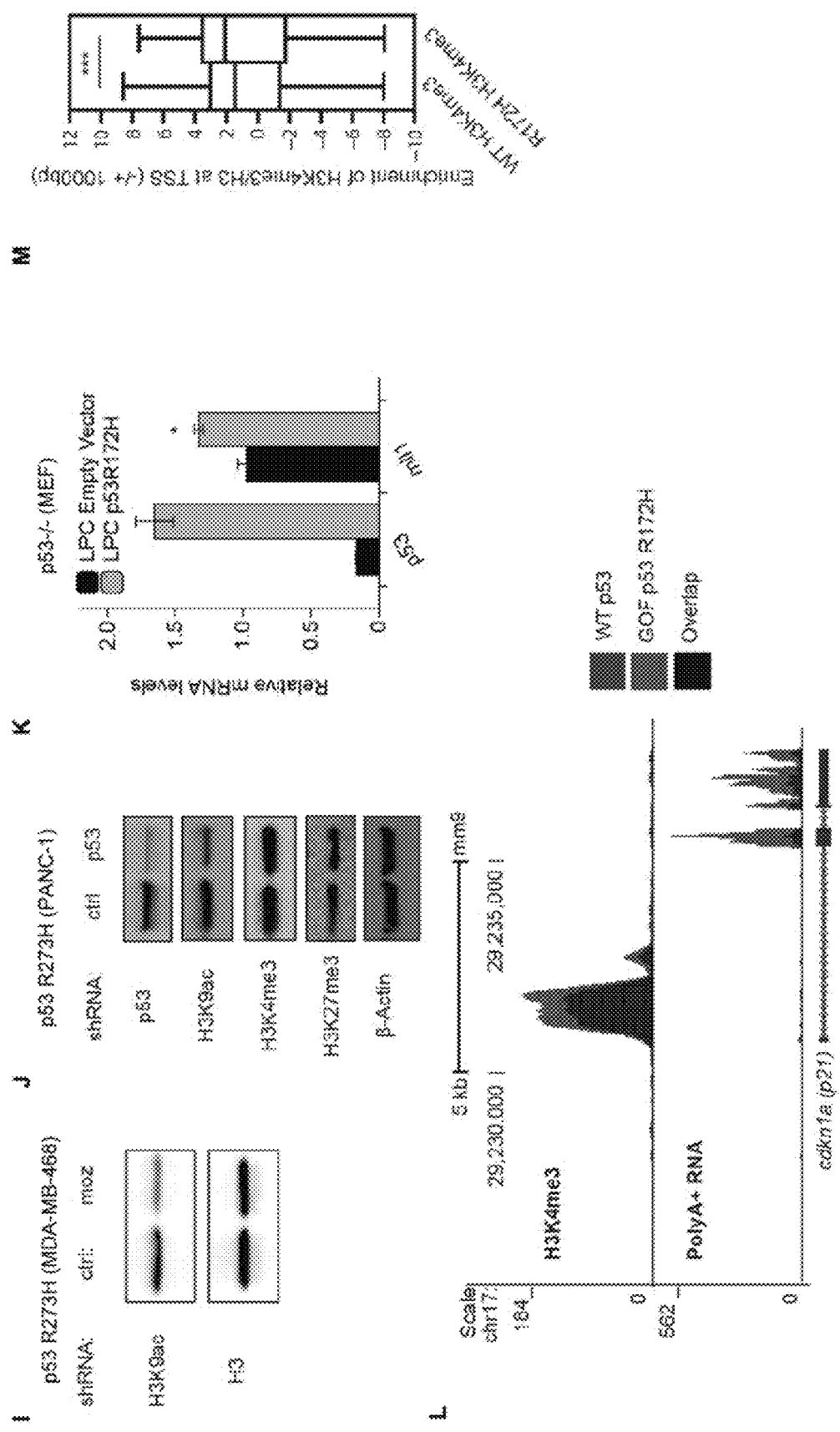

The regulation of histone modifying enzymes by GOF p53 led to investigation of the levels of the cognate histone post-translational modifications. Indeed, by western analysis, a modest global decrease in histone H3 Lysine 9 acetylation (H3K9ac, catalyzed by MOZ (Voss et al., 2009, Dev Cell, 17: 674-686)) was observed in response to knockdown of GOF p53 by either siRNA (FIG. 13F) or shRNA (FIG. 13G), whereas other histone acetylation marks did not show significant changes (FIG. 13G and FIG. 13H). The reduction in H3K9ac level was also observed when moz level itself was decreased by shRNA (FIG. 13I). Similarly, in PANC-1 cells, H3K9ac was decreased when GOF p53 level was lowered (FIG. 13J). On the other hand, H3 Lysine 4 tri-methylation and H3 Lysine 4 mono-methylation (H3K4me3 and H3K4me1, catalyzed by MLL1 and MLL2, respectively 21) showed only very slight global changes upon GOF p53 knockdown (FIG. 13F, FIG. 13G, FIG. 13H and FIG. 13J). This is reasonable, however, given that H3K4 is methylated by six members of the COMPASS complexes (Shilatifard, 2012, Annu Rev Biochem, 81: 65-95), and indeed, previous data showed that inhibiting or knocking out one of them did not substantially change global levels of H3K4 methylation (Cao et al., 2014, Mol Cell, 53: 247-261; Wang et al., 2009, Mol Cell Biol, 29: 6074-6085).

Figures 8H, 8I, 8J, 8K, 8L, 8M:
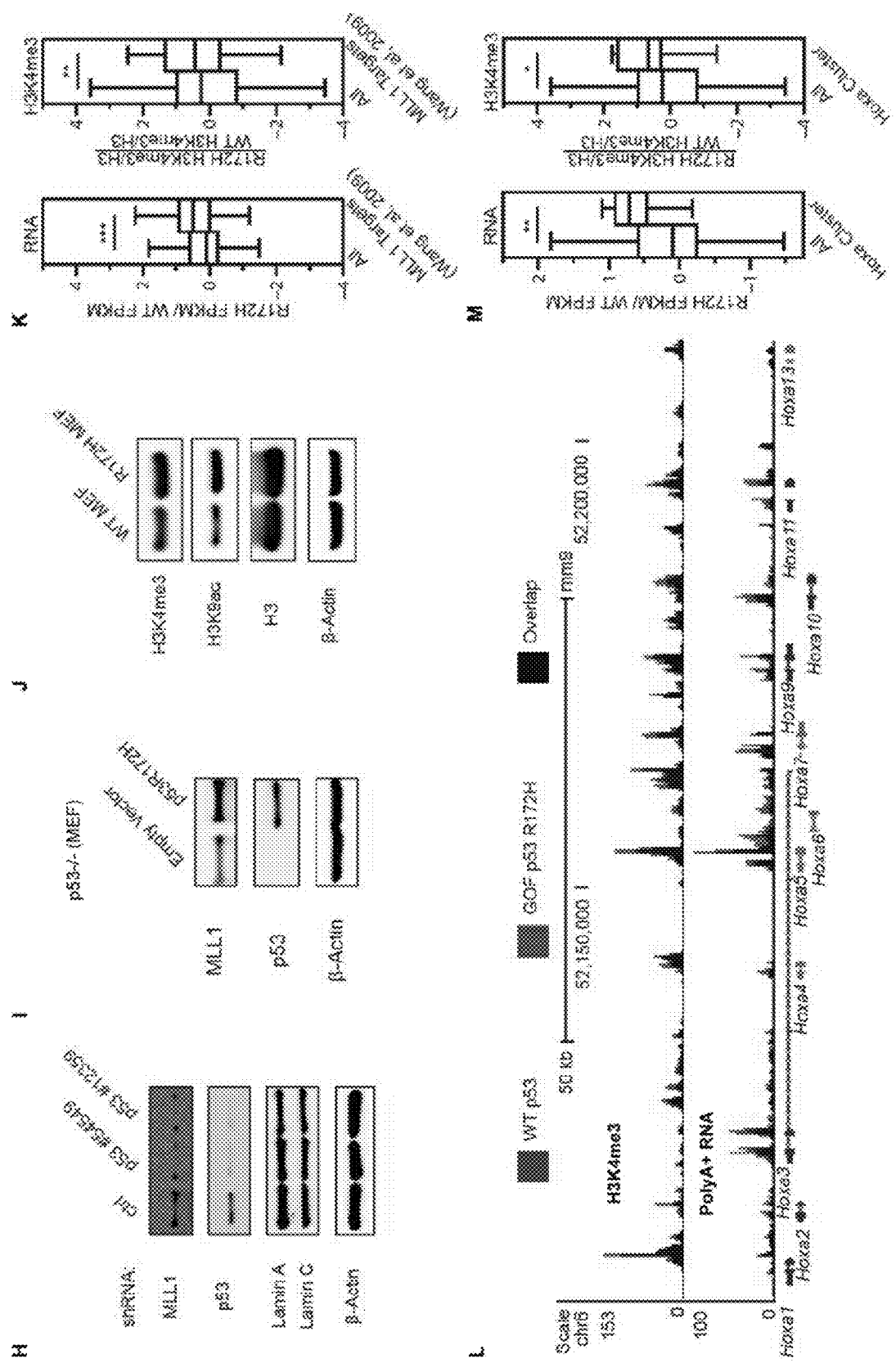

To further investigate the pathway in a more genetically controlled system, the regulation of mll1 by GOF p53 was validated in the knock in MEFs described above. Consistently, modestly higher expression of mll1 in GOF p53 MEFs was found, compared to in WT p53 MEFs, at both mRNA (FIG. 8E) and protein levels (FIG. 8F). When GOF p53 was reduced, mll1 expression was also lowered (FIG. 8G and FIG. 8H). Moreover, ectopically expressing GOF p53 in MEFs derived from p53 knockout mice (Trp53−/−) enhanced mll1 expression (FIG. 8I and FIG. 13K). Furthermore, similar to the results obtained from cancer cells, GOF p53 MEFs showed higher global levels of H3K9ac compared with WT p53 MEFs (FIG. 8J). Global H3K4me3 was also slightly elevated in GOF p53 MEFs, but not to the extent of H3K9ac (FIG. 8J), again presumably due to redundancy of other members of COMPASS complexes.

Thus, GOF p53 may lead to local changes in H3K4 methylation levels. Genome wide gene-specific expression and H3K4 methylation changes was then investigated using RNA-seq and ChIP-seq for H3K4me3 in MEFs with endogenous WT p53 or GOF p53. Importantly, compared with the genome wide average, known MLL1 target genes (Wang et al., 2009, Mol Cell Biol, 29: 6074-6085) were more highly expressed and displayed higher H3K4me3 enrichment (normalized to total histone H3) in GOF p53 MEFs than in WT p53 MEFs (FIG. 8K). For example, increased H3K4me3 levels and RNA expression was observed within the Hoxa gene cluster (FIG. 8L and FIG. 8M), a well-studied target of MLL1 and commonly misregulated in leukemia (Milne et al., 2002, Mol Cell, 10: 1107-1117; Nakamura et al., 2002, Mol Cell, 10: 1119-1128). Conversely, canonical p53 target genes, such as p21, showed decreased RNA expression and TSS-associated H3K4me3 in GOF p53 MEFs (FIG. 13L), suggesting a loss of WT p53 function. Notably, H3K4me3 enrichment at the TSS of genes in GOF p53 R172H MEFs was slightly, but significantly higher at a genome wide level than in WT p53 MEFs (FIG. 13M), consistent with the global level of H3K4me3 measured by western blot (FIG. 8J), further suggesting increased MLL activity downstream of GOF p53.

Figures 16A, 16B, 16C, 16D:
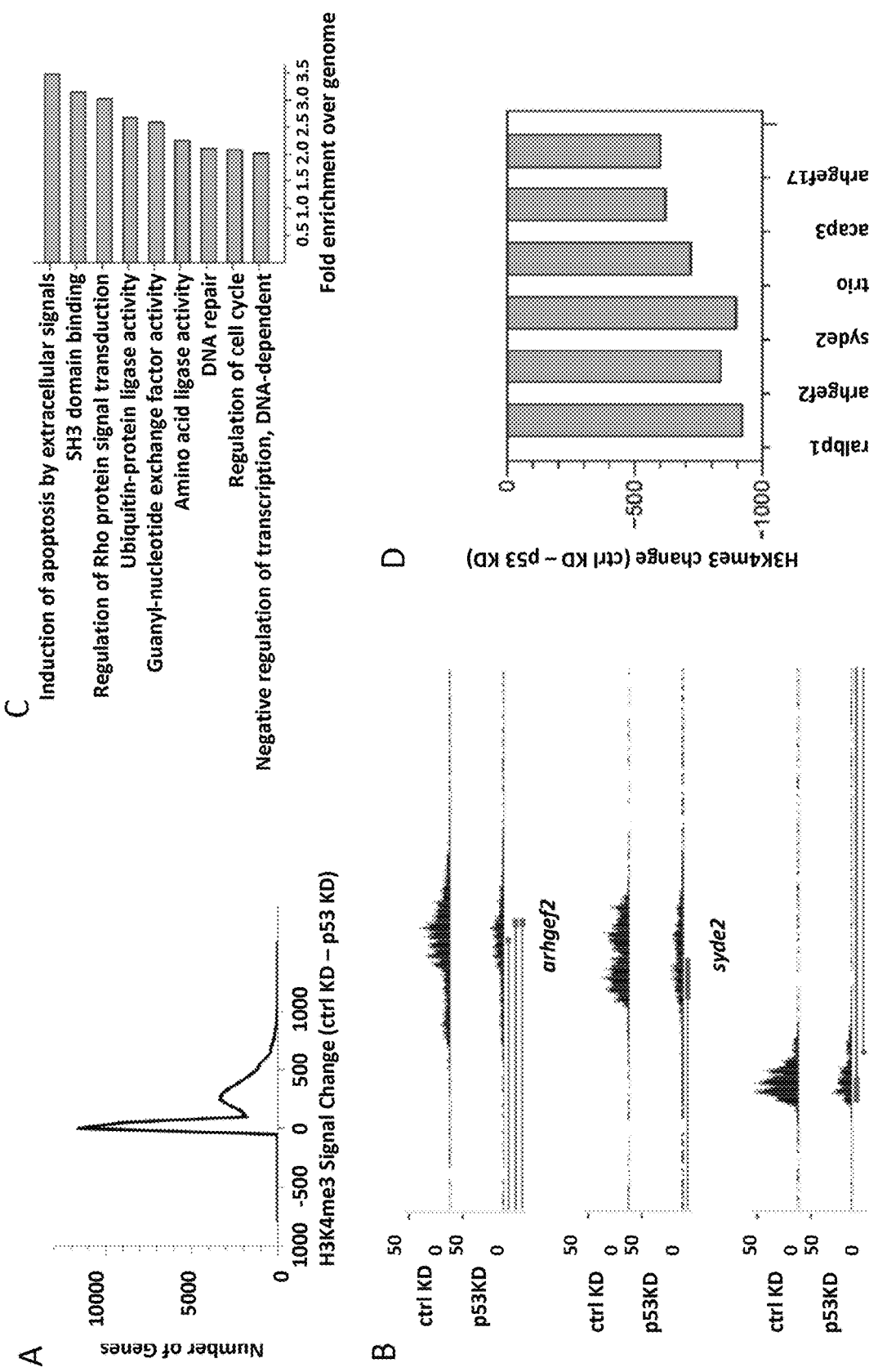

Experiments were designed to investigate gene-specific H3K4 methylation changes using H3K4me3 ChIP-seq, comparing GOF p53 knockdown with scrambled control knockdown. While H3K4me3 remained unchanged at the TSS region of most genes (FIG. 16A), as expected from the global H3K4me3 level result, H3K4me3 signal decreased at a portion of gene TSS regions (FIG. 16A) upon GOF p53 knockdown. GO analysis was performed for genes with top 5% decrease of H3K4me3 signal at their TSS regions. Of the top five categories, three came up as terms related to rho and ras GTPase signaling pathways that are growth promoting (White et al. 2013 Genes Dev 27, 2065-2071; Karlsson et al., 2009 Biochim Biophys Acta 1796, 91-98) (FIG. 16C). Track views of genes in these pathways confirmed the GO analysis (FIG. 16C).

Figures 9A, 9B, 9C, 9D, 9E, 9F:
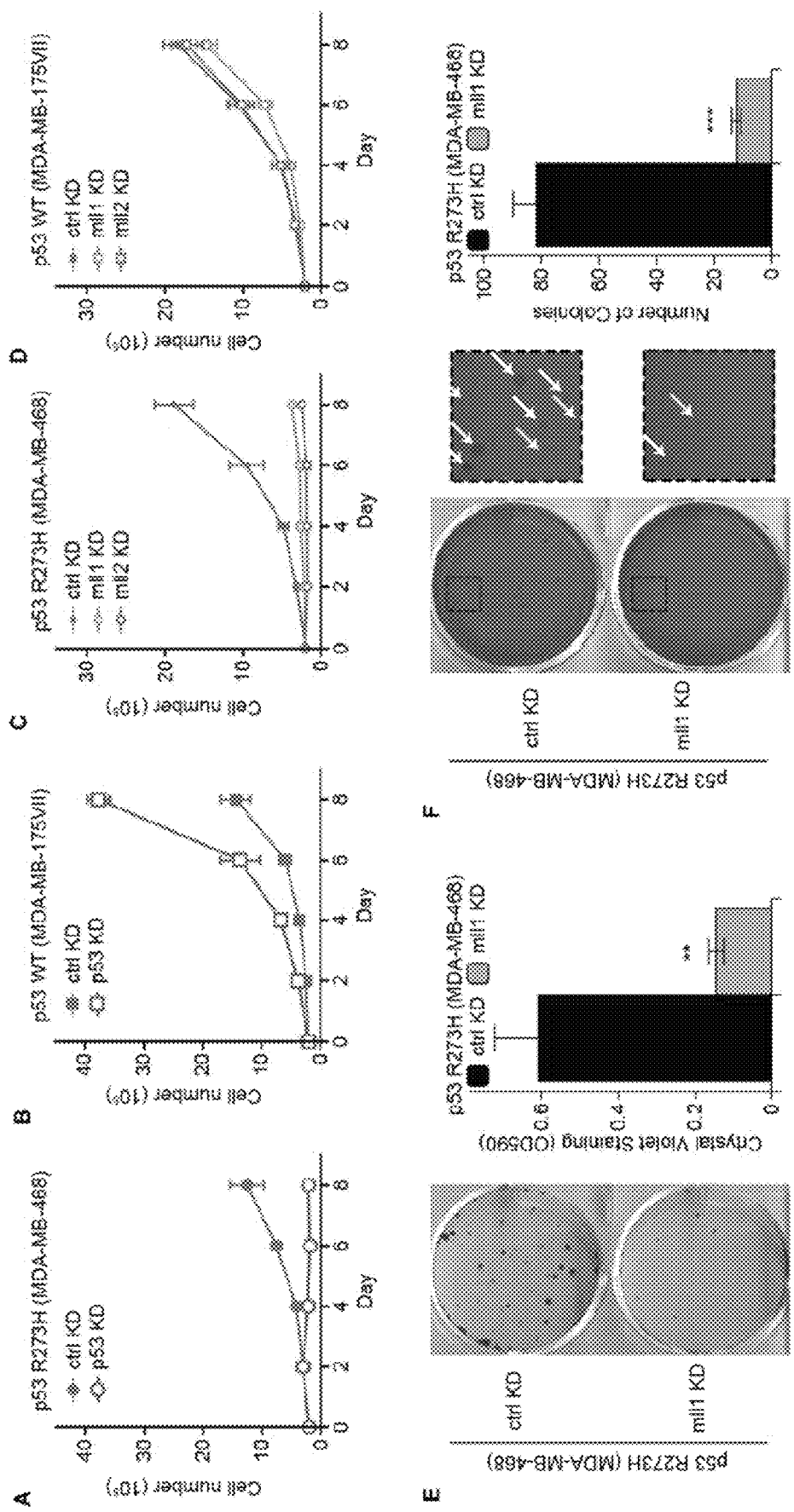
FIG. 9A through FIG. 9L, depicts the results of experiments demonstrating that MLL1/2 knockdown phenocopies p53 knockdown in reducing cell growth rate of GOF p53 cells, but not WT p53 or p53 null cells.
Figures 14A, 14B, 14C, 14D, 14E, 14F:
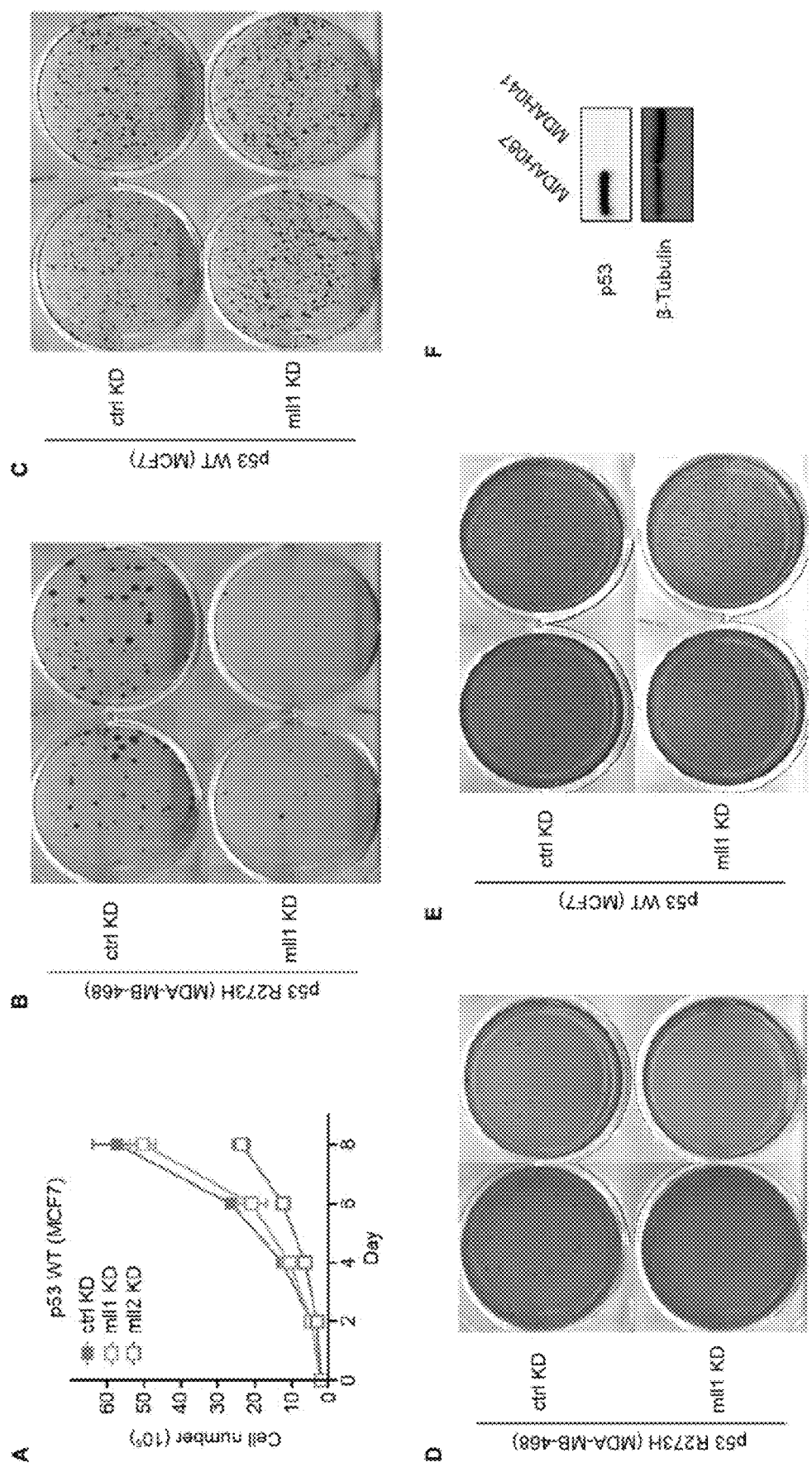
FIG. 14A through FIG. 14M, depicts the results of experiments.

Previous studies have revealed that cells with GOF p53 rely on p53 for cell growth and survival (Lim et al., 2009, Br J Cancer, 101: 1606-1612). Consistently, it is shown that GOF p53 knockdown in MDA-MB-468 cancer cells leads to strong decrease in cell growth compared with control knockdown cells (FIG. 9A). In contrast, when WT p53 level was lowered, the growth rate was increased (FIG. 9B), likely due to p53's normal role in cell cycle arrest. In order to investigate the functional significance of GOF p53 driving the epigenetic regulators, the same time course was carried out for shRNA-mediated knockdown of mll1 or mll2. Strikingly, the reduction of MLL1 or MLL2 in GOF p53 cancer cells led to dramatic loss of cell growth (FIG. 9C), phenocopying the knockdown of GOF p53 itself. In contrast, knockdown of mll1 or mll2 had minimal effect on growth of WT p53 cancer cells (FIG. 9D and FIG. 14A).

Figures 9G, 9H, 9I, 9J, 9K, 9L:
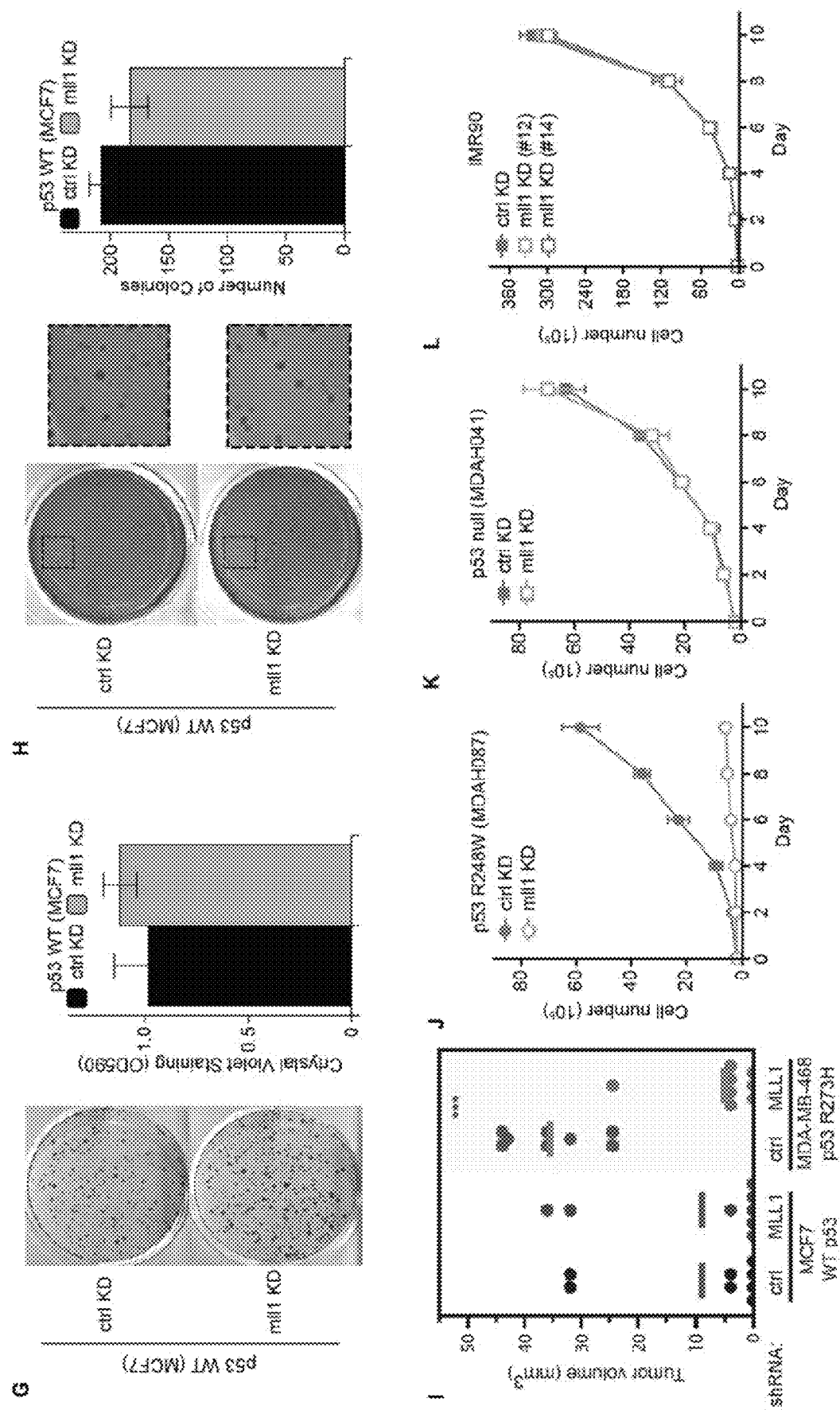

The importance of this pathway to tumor relevant phenotypes was addressed first by examining the ability of the cells to form colonies. While the GOF p53 breast cancer cells efficiently grew into colonies, reduction of MLL1 decreased colony formation (FIG. 9E and FIG. 14B), but had little effect on the efficiency of colony formation by WT p53 cancer cells (FIG. 9G and FIG. 14C). The tumor formation phenotype was further confirmed in a three-dimensional anchorage-independent growth assay in soft agar. Once again, decreasing MLL1 specifically reduced the growth and colony size of GOF p53 cancer cells (FIG. 9F, note colonies at arrows, and FIG. 14D), but not WT p53 cancer cells (FIG. 9H and FIG. 14E).

Figures 14G, 14H, 14I, 14J, 14K, 14L, 14M:
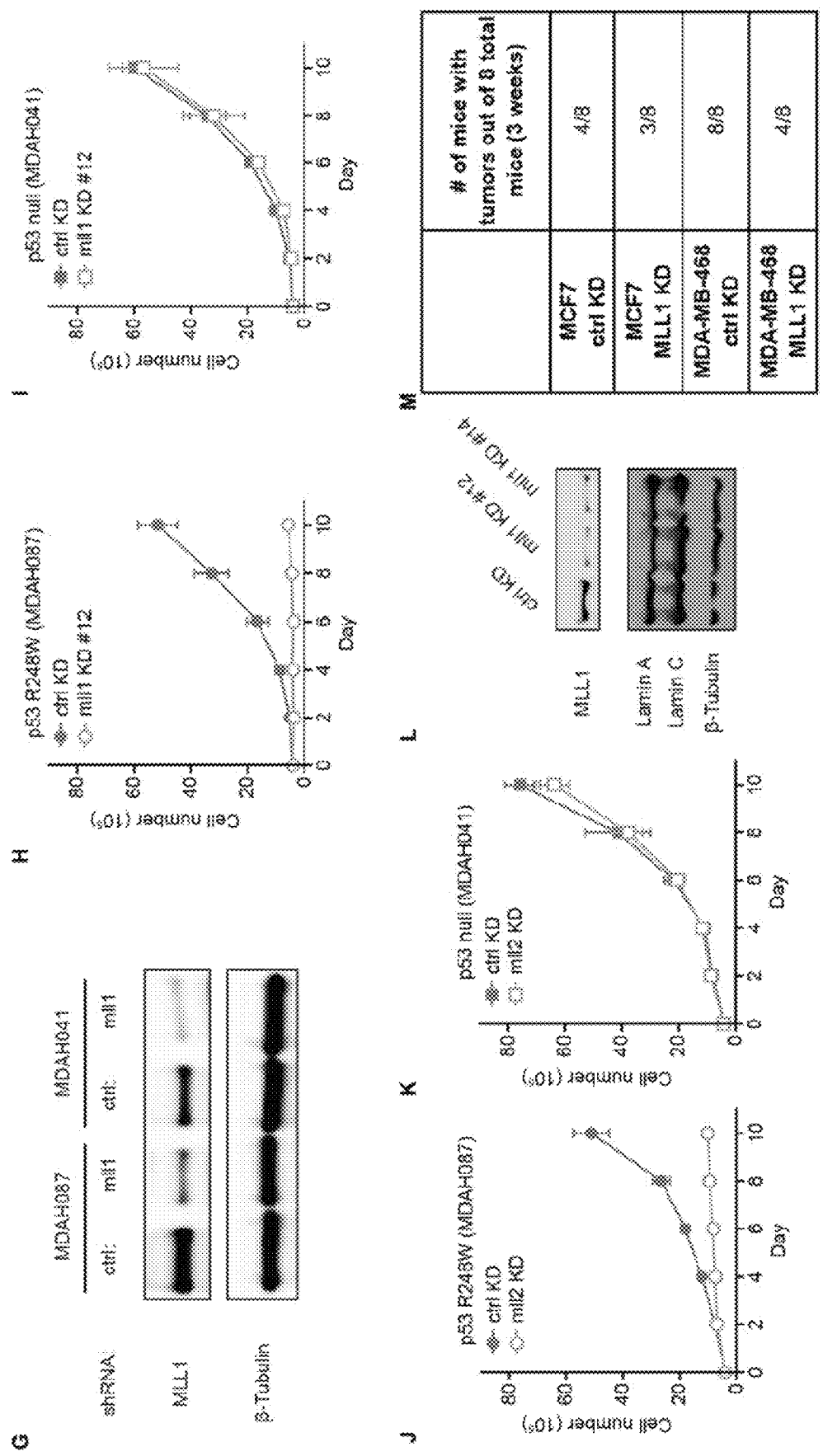

Moreover, the tumor formation phenotype was investigated by examining tumor growth on NOD-scid-gamma (NSG) immune-deficient mice. Three weeks after subcutaneous injection, with MLL1 knockdown, largely reduced tumor formation ability, as well as decreased tumor incidence in GOF p53, was observed as compared to GOF p53 cells with non-targeting scrambled control knockdown (FIG. 9I and FIG. 14M). This in vivo tumor growth result is consistent with observations in the two-dimensional and three-dimensional colony formation experiments (FIG. 9E and FIG. 9F). On the other hand, MLL1 knockdown in cancer cells with WT p53 did not change tumor incidence (FIG. 14M) or tumor volume (FIG. 9I) compared with non-targeting control knockdown, again, suggesting a specific role of MLL1 in cancers with GOF p53, but not WT p53.

To further explore a critical role that these epigenetic regulators may play in supporting growth of GOF p53 cells, and to rule out possible confounding factors in established cancer cell lines, mll1 knockdowns were performed in non-cancer Li-Fraumeni Syndrome (LFS) cells (FIG. 14G)—MDAH087 (p53 R248W) and MDAH041 (the latter cell line bears p53 homozygous truncation, and is considered to be null for p53 activity (Zhu et al., 2001, Cancer Res, 61: 64-70); FIG. 14F). Similar to the results in the breast cancer cell lines, mll1 knockdown, with two independent shRNAs, reduced the growth rate of GOF p53 LFS cells (FIG. 9J and FIG. 14H), but did not reduce the growth of either p53 null LFS cells (FIG. 9K and FIG. 14I), nor primary non-cancer cells with WT p53 (IMR90 lung fibroblasts, FIG. 9L and FIG. 14L). In addition, mll2 knockdown also decreased GOF p53 LFS cell growth (FIG. 14J), but not p53 null LFS cells (FIG. 14K).

Figures 15A, 15B, 15C, 15D, 15E, 15F:
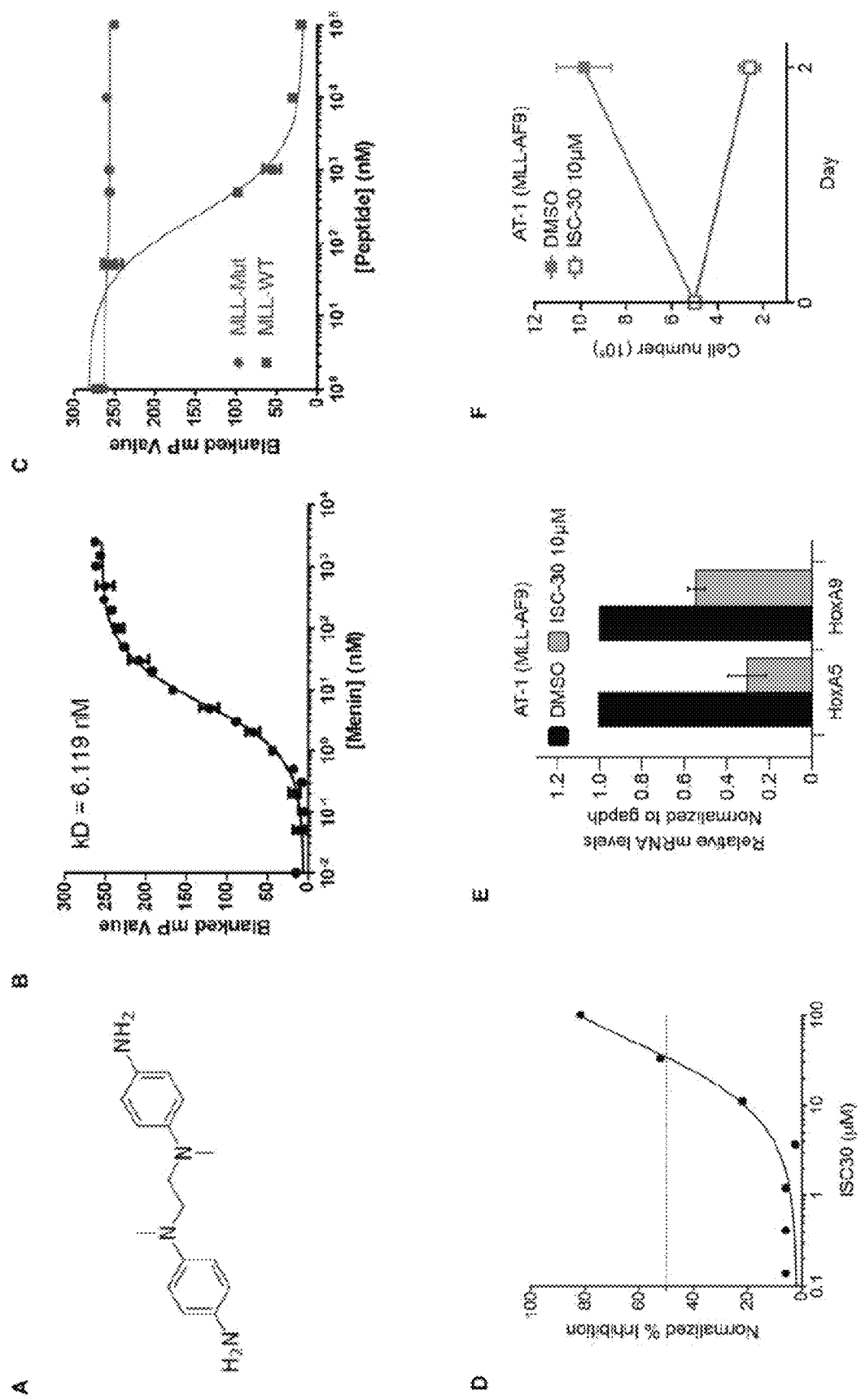
FIG. 15A through FIG. 15G, depicts the results of example experiments.

Epigenetic regulators have become promising targets of small molecule compounds in various human diseases including cancer (Dawson et al; 2012, Cell, 150: 12-27; Dawson et al., 2012, N Engl J Med, 367: 647-657). The MLL enzymes are components of several multi-subunit protein complexes, called COMPASS21. Menin is a scaffold protein of the COMPASS complex, directly interacting with the N-terminal part of MLL1 with a deep pocket (Huang et al., 2012, Nature, 482: 542-546; Matkar et al., 2013, Trends Biochem Sci, 38: 394-402; Yokoyama et al, 2004, Mol Cell Biol, 24: 5639-5649; Caslini et al., 2007, Cancer Res, 67: 7275-7283). This interaction has been shown to be crucial for upregulation of Hox genes and maintenance of a subtype of leukemia (Thiel et al., 2012, Bioessays, 34: 771-780; Yokoyama et al., 2005, Cell, 123: 207-218). A virtual screening of approximately 140,000 NCI small molecule compounds was performed based on the structure of menin that mediates the direct binding to the MLL1 peptide, and an effective compound referred to as "ISC-30" (Kiss et al., 2008, Journal of Medicinal Chemistry, 51: 3145-3153) was identified (FIG. 15A). A fluorescence polarization assay testing FITC-MLL1 peptide binding with the menin protein was optimized (FIG. 14B and FIG. 14C), and it was found that ISC-30 started to inhibit menin-MLL1 interaction at approximately 2 µM, and had an IC50 of 32 µM (FIG. 15D). As expected, ISC-30 treatment decreased expression of Hoxa cluster genes, the known and direct targets of the menin/MLL axis, in a mouse leukemia cell line, AT-1, which was transformed by the oncogenic MLL-AF9 fusion protein (Thiel et al., 2010, Cancer Cell, 17: 148-159) (FIG. 14E). Furthermore, the growth of AT-1 cells was reduced by treatment of ISC-30 (FIG. 15F).

Figures 10A, 10B, 10C, 10D, 10E, 10F, 10G:
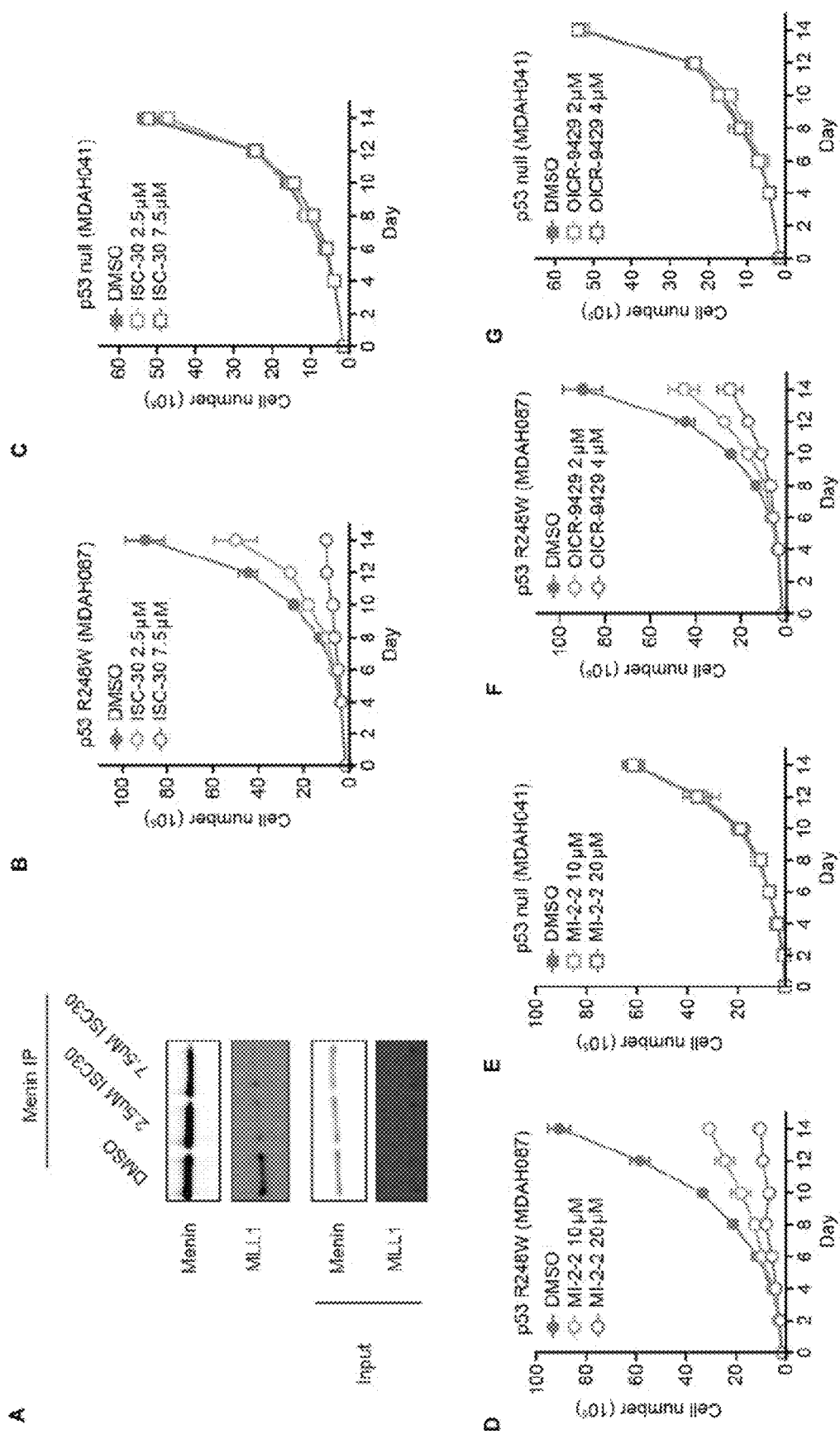
FIG. 10A through FIG. 10G, depicts the results of experiments demonstrating that pharmacological inhibition with menin inhibitor or WDR5 inhibitor reduces growth of GOF p53, but not p53 null cells.
Figure 15G:
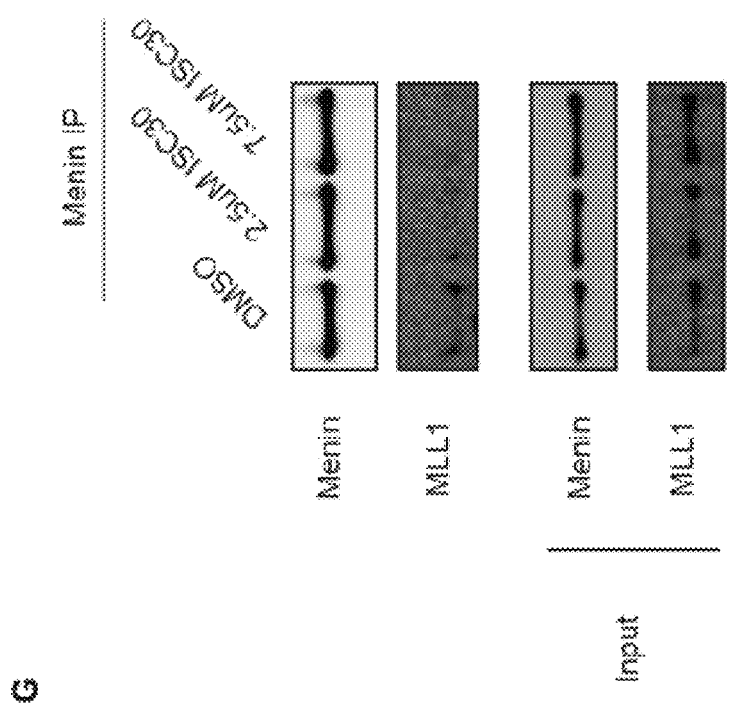

Both LFS p53 GOF cells and LFS p53 null cells were treated with ISC-30 menin antagonist. Consistent with the in vitro results, ISC-30 blocked menin-MLL1 interaction at endogenous levels in a dose-dependent manner, in both p53 GOF (FIG. 10A) and p53 null cells (FIG. 15G). Strikingly, in agreement with the mll genetic knockdown experiments in GOF p53 cells, ISC-30 showed a dose-dependent inhibition of GOF p53 cell growth (FIG. 10B), but had very little effect on p53 null cells (FIG. 10C). In addition, the same time course was carried out with a second, established menin inhibitor, MI-2-2 (Grembecka et al., 2012, Nat Chem Biol, 8: 277-284; Shi et al., 2012, Blood, 120: 4461-4469). Similarly, MI-2-2 showed a dose-dependent inhibition of GOF p53 cell growth (FIG. 10D), but not p53 null cells (FIG. 10E).

Recently, inhibition of MLL function has also been demonstrated by targeting its interaction with the essential WDR5 subunit of the COMPASS complex with either peptide mimetics (Karatas et al., 2013, Journal of American Chemical Society, 135: 669-682) or small molecules. Thus, as a second approach to pharmacological inhibition of MLL activity, OICR-9429, a newly characterized potent and selective antagonist of the interaction of WDR5 with MLL was used. This non-peptide, drug-like molecule binds to WDR5 in the MLL binding site of WDR5 (KD=93±28 nM), and disrupts the assembly of the WDR5/MLL1/RbBP5 complex in cells with IC50 values below 1 µM (Grebien et. al., 2015, Nature Chemical Biology, in revision). In striking similarity to ISC-30 and MI-2-2 targeting menin-MLL, a dose-dependent inhibition by OICR-9429 of GOF p53 cell growth (FIG. 10F) was found, and, again, little effect on p53 null cell growth (FIG. 10G).

The results presented herein indicate that distinct prevalent GOF p53 mutants bind to a common group of new gene promoter elements genome-wide, to drive expression of genes comprising an epigenetic signature. The GOF p53 mapping occurs immediately adjacent to ETS binding motifs, and GOF p53 binds directly to ETS2 in vitro and in vivo, strongly indicating that the substitutions in the DNA binding domain of p53 unleash a latent interaction with the ETS family of transcription factors, as previously suggested (Do et al., 2012, Genes Dev, 26: 830-845). Within the epigenetic signature of genes targeted by p53 GOF, the MLL COMPASS pathway appears to be particularly represented, as mll1, mll2 and rbbp5 genes are all bound by the mutant p53, but the new binding includes other epigenetic regulators, such as the acetyltransferase, moz. It was found that expression of these key epigenetic regulators is dependent on GOF p53, which in turn elevates activating histone modifications, including H3K4 methylation and H3K9 acetylation. In certain instances, histone modification occurs particularly at genes that may contribute to GOF p53 oncogenic phenotype and therefore cancer progression, including the genes of the rho/ras pathways.

The data presented herein points to MLL downstream pathways as key targets of GOF p53. This was revealed in mouse embryo fibroblasts isolated from mice bearing knock-in of GOF p53. In this system the key H3K4me3 modification is elevated at known MLL target genes 23, including Hox gene clusters, resulting in their increased expression. Thus, as is the case in leukemia bearing translocations of MLL, MLL pathways may contribute to GOF p53 oncogenic phenotypes and therefore cancer progression.

Importantly, the present findings in both human breast cancer-derived cell lines and Li-Fraumeni Syndrome-derived cells show that GOF p53 cells lose growth and tumor formation potential with similar kinetics upon knockdown of mll1 or mll2 as they do with knockdown of GOF p53. A key comparison to breast cancer and Li-Fraumeni Syndrome cells that express WT p53 or are null for p53, shows very little effect of mll knockdown on cell growth. Hence, p53 GOF cells are exquisitely growth dependent on the MLL pathway.

Further evidence of GOF p53 cell growth dependence on the COMPASS protein complex, which leads to H3K4 methylation, was provided by way of cell sensitivity to three different pharmacological small compound inhibitors. These compounds target menin or WDR5 interaction with MLL, and all show specific inhibition of cell growth of GOF p53, but not null p53, in the Li-Fraumeni Syndrome cell lines, The effects of the inhibitors are thus analogous to direct knockdown of mll. Hence, it is concluded that a large cohort of p53 GOF-driven cancers, not previously known to be growth dependent on chromatin pathways, may be amenable to epigenetic therapeutics.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of treating cancer caused by a p53 gain of function (GOF) mutation selected from the group consisting of R248Q, R248W, R249S, and R273H in a subject comprising administering to the subject an effective amount of a composition comprising at least one compound selected from the group consisting of MI-2-2 or a derivative or analogue thereof, OICR-9429 or a derivative or analogue thereof, or —N,N'-bis(4-aminophenyl)-N,N'-dimethylethylenediamine (ISC-30) or a derivative or analogue thereof:

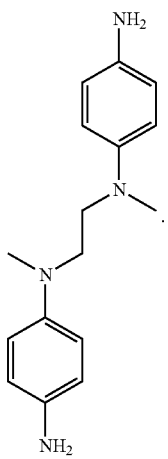 [SMILES: CN(CCN(C)c1ccc(N)cc1)c1ccc(N)cc1]

2. The method of claim 1, wherein the compound inhibits the interaction between an MLL and menin.

3. The method of claim 2, wherein the compound is N,N'-bis(4-aminophenyl)-N,N'-dimethylethylenediamine (ISC-30)

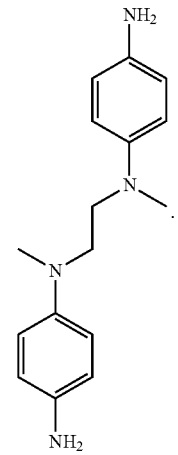 [SMILES: CN(CCN(C)c1ccc(N)cc1)c1ccc(N)cc1]

4. The method of claim 2, wherein the compound is MI-2-2, or an analog or derivative thereof.

5. The method of claim 1, wherein the compound inhibits the interaction between an MLL and WDR5.

6. The method of claim 5, wherein the compound is OICR-9429, or a derivative or analogue thereof.

7. The method of claim 1, wherein the cancer is selected from the group consisting of carcinomas, sarcomas, lymphomas, leukemia, blastomas, germ cell cancers, breast cancer, lung cancer, pancreatic cancer, stomach cancer, bone cancer, ovarian cancer, prostate cancer, bladder cancer, cervical cancer, colon cancer, skin cancer, gliomas, esophageal cancer, oral cancer, gallbladder cancer, liver cancer, testicular cancer, uterine cancer, thyroid cancer, throat cancer, Li-Fraumeni Syndrome and a combination thereof.

8. A personalized method of treating cancer in a subject comprising detecting a p53 gain of function (GOF) mutation selected from the group consisting of R248Q, R248W, R249S, and R273H, in a tumor cell of the subject, and administering to the subject an effective amount of a composition comprising at least one compound selected from the group consisting of MI-2-2 or a derivative or analogue thereof, OICR-9429 or a derivative or analogue thereof, or —N,N'-bis(4-aminophenyl)-N,N'-dimethylethylenediamine (ISC-30) or a derivative or analogue thereof:

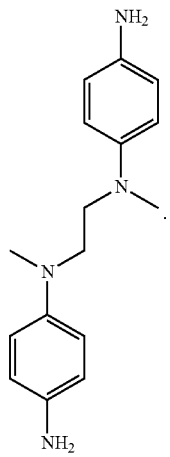 [SMILES: CN(CCN(C)c1ccc(N)cc1)c1ccc(N)cc1]

9. The method of claim 8, wherein the compound inhibits the interaction between an MLL and menin.

10. The method of claim 9, wherein the compound is N,N'-bis(4-aminophenyl)-N,N'-dimethylethylenediamine (ISC-30)

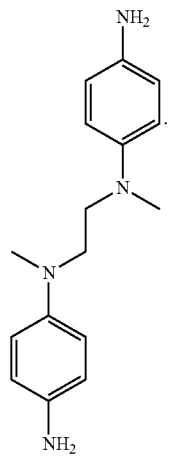 [SMILES: CN(CCN(C)c1ccc(N)cc1)c1ccc(N)cc1]

11. The method of claim 9, wherein the compound is MI-2-2 or a derivative or analogue thereof.

12. The method of claim 8, wherein the compound inhibits the interaction between an MLL and WDR5.

13. The method of claim 12, wherein the compound is OICR-9429, or a derivative or analogue thereof.

14. The method of claim 8, wherein the cancer is selected from the group consisting of carcinomas, sarcomas, lymphomas, leukemia, blastomas, germ cell cancers, breast cancer, lung cancer, pancreatic cancer, stomach cancer, bone cancer, ovarian cancer, prostate cancer, bladder cancer, cervical cancer, colon cancer, skin cancer, gliomas, esophageal cancer, oral cancer, gallbladder cancer, liver cancer, testicular cancer, uterine cancer, thyroid cancer, throat cancer, Li-Fraumeni Syndrome and combinations thereof.

* * * * *